(12) United States Patent
Tsuboyama et al.

(10) Patent No.: US 7,808,175 B2
(45) Date of Patent: Oct. 5, 2010

(54) LIGHT EMITTING MATERIAL AND LIGHT EMITTING DEVICE

(75) Inventors: Akira Tsuboyama, Tokyo (JP); Koichi Suzuki, Yokohama (JP); Taiki Watanabe, Akishima (JP); Kazunori Ueno, Ebina (JP)

(73) Assignee: Canon Kabushiki Kaisha, Tokyo (JP)

( * ) Notice: Subject to any disclaimer, the term of this patent is extended or adjusted under 35 U.S.C. 154(b) by 685 days.

(21) Appl. No.: 11/764,436

(22) Filed: Jun. 18, 2007

(65) Prior Publication Data

US 2008/0009627 A1   Jan. 10, 2008

(30) Foreign Application Priority Data

Jul. 7, 2006   (JP) .............................. 2006-187811

(51) Int. Cl.
*H01L 51/50* (2006.01)
*C09K 11/06* (2006.01)
*C07F 15/00* (2006.01)

(52) U.S. Cl. ........................... 313/504; 428/690; 546/10
(58) Field of Classification Search ................. 428/690; 313/504; 546/10
See application file for complete search history.

(56) References Cited

U.S. PATENT DOCUMENTS

| 7,108,924 B2 | 9/2006 | Kamatani et al. | ........... 428/690 |
| 7,166,958 B2 | 1/2007 | Furugori et al. | ............. 313/504 |
| 7,189,466 B2 | 3/2007 | Moriyama et al. | ........... 428/690 |
| 2003/0141809 A1 | 7/2003 | Furugori et al. | ............. 313/504 |
| 2006/0280968 A1 | 12/2006 | Kamatani et al. | ........... 428/690 |

FOREIGN PATENT DOCUMENTS

| WO | WO 02/44189 | 6/2002 |
| WO | WO 03/091355 | 11/2003 |
| WO | WO 2006/062226 A1 * | 6/2006 |

OTHER PUBLICATIONS

Chen et al., "Recent Developments in Molecular Organic Electroluminescent Materials," *Macromol. Symp.*, vol. 125, 1-48 (1997).

Lamansky et al., "Synthesis and Characterization of Phosphorescent Cyclometalated Iridium Complexes," *Inorg. Chem.*, vol. 40, 1704-1711 (2001).

Lamansky et al., "Highly Phosphorescent Bis-Cyclometalated Iridium Complexes: Synthesis, Phtophysical Characterization, and Use in Organic Light Emitting Diodes," *J. Am. Chem. Soc.*, vol. 123, 4304-4312 (2001).

Zhu et al., "Highly Efficient Electrophosphorescent Devices Based on Conjugated Polymers Doped with Iridium Complexes," *Appl. Phys. Letts.*, vol. 80, No. 12, 2045-2047 (2002).

Chen et al., "Energy Transfer and Triplet Exciton Confinement in Polymeric Electrophosphorescent Devices," *J. Polymer Science: Part B: Polymer Phys.*, vol. 41, 2681-2690 (2003).

Sandee et al., "Solution-Processible Conjugated Electrophosphorescent Polymers," *J. Am. Chem. Soc.*, vol. 126, 7041-7048 (2004).

* cited by examiner

*Primary Examiner*—Charanjit S Aulakh
(74) *Attorney, Agent, or Firm*—Fitzpatrick, Cella, Harper & Scinto

(57) ABSTRACT

Provided is a light emitting material of which a light emitting device having high luminous efficiency and high stability and capable of being provided at a low cost can be formed. A light emitting material includes the following partial structural formula (1):

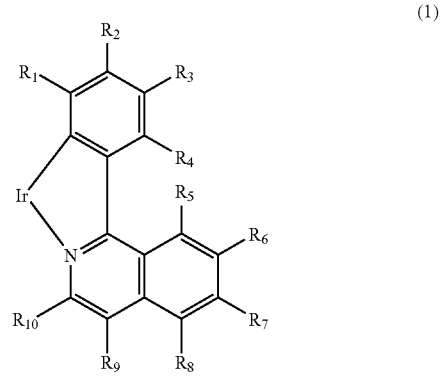

(1)

wherein at least one of $R_1$ to $R_{10}$ represents a substituent except a hydrogen atom, a total number of benzene ring structures in $R_1$ to $R_{10}$ is 3 or more, and $R_1$ to $R_{10}$ include a trifluoromethyl group, or a linear, branched, or cyclic alkyl or alkoxyl group having 2 or more carbon atoms a hydrogen atom of which may be substituted by a halogen atom.

5 Claims, 1 Drawing Sheet

LIGHT EMITTING MATERIAL AND LIGHT EMITTING DEVICE

BACKGROUND OF THE INVENTION

1. Field of the Invention

The present invention relates to a light emitting material and a light emitting device using an organic compound, and more specifically, to a light emitting device using a metal coordination compound as a light emitting material.

2. Description of the Related Art

Applied researches have been vigorously conducted on an organic electroluminescence (EL) device because of the potential of the device to function as a light emitting device having high-speed responsiveness and high luminous efficiency (Macromol. Symp., 1997, 125, 1-48). Among the research, a wide range of researches on an iridium metal coordination compound has been carried out because the compound can function as a light emitting material having high luminous efficiency and high stability when used in an organic EL device (Inorganic. Chemistry. 2001, 40, 1704-1711, Journal. American. Chemical. Society. 2001, 123, 4304-4312, International Publication No. 02/44189, and International Publication No. 03/91355).

Organic EL devices each using an iridium coordination compound as a phosphorescent dopant are roughly classified into two kinds: a device to be produced by a vacuum vapor deposition method (Inorganic. Chemistry. 2001, 40, 1704-1711, and Journal. American. Chemical. Society. 2001, 123, 4304-4312) and a device to be produced by applying a solution prepared by dissolving a predetermined amount of the compound in a solvent to an electrode substrate by, for example, a spin coating method, a printing method, or an ink-jet method (Applied Physics Letters 80, 2045-2047 (2002), and Journal of Polymer Science: Part B: Polymer Physics 41, 2681-2690 (2003)).

A research and development of a device to be produced by the vacuum vapor deposition method have progressed, and the device has a relatively high level of performance because the device has high luminous efficiency and high stability at the time of driving. On the other hand, as pointed out in Journal of Polymer Science: Part B: Polymer Physics 41, 2681-2690 (2003), a device to be produced by an application method cannot provide sufficient performance when the light emitting layer of the device is formed of two kinds of materials, that is, an iridium coordination compound and a host material. In other words, owing to, for example, a problem of compatibility between both materials and a difference in solubility in a solvent between the materials, a phenomenon such as the inhibition of light emission by the agglomeration of the iridium coordination compound in the device occurs, so the device is problematic in terms of luminous efficiency and stability at the time of driving, and hence cannot provide sufficient performance.

In addition, Journal. American. Chemical. Society. 2004, 126, 7041-7048 proposes a compound using an oligofluorenyl group, in which a fluorene group continues to $Ir(ppy)_2$(acac) that emits green light or $Ir(btp)_2$(acac) that emits red light in a linear fashion, as a substituent. However, the external quantum efficiency of a device using such compound is as low as 1.5% at best. In addition, an iridium coordination compound $Ir(btp)_2$(acac) that is intrinsically unsubstituted has a luminous wavelength of 2 eV (620 nm), but providing the compound with an oligofluorenyl group shifts the luminous wavelength to about 1.8 eV or more to 1.9 eV or less (650 nm or more to 690 nm or less). An influence of the substituent increases the number of deactivation paths to reduce the luminous efficiency of the device. Moreover, the fact that the luminous wavelength shifts to the range of 1.8 eV or more to 1.9 eV or less (650 nm or more to 690 nm or less) where a human being shows weak red visual sensitivity is also a large factor for reducing the luminous efficiency.

Therefore, no phosphorescent dopant suitable for an application method has been heretofore found in red light emitting materials, and the development of such dopant has been an object.

SUMMARY OF THE INVENTION

An object of the present invention is to provide a light emitting material of which a light emitting device having high luminous efficiency and high stability and capable of being provided at a low cost can be formed, and a light emitting device using the light emitting material.

That is, according to the present invention, there is provided a light emitting material including the following partial structural formula (1) is provided:

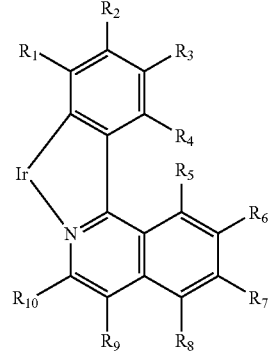

(1)

wherein at least one of $R_1$ to $R_{10}$ represents a substituent except a hydrogen atom, a total number of benzene ring structures in $R_1$ to $R_{10}$ is 3 or more, and $R_1$ to $R_{10}$ include a trifluoromethyl group, or a linear, branched, or cyclic alkyl or alkoxyl group having 2 or more carbon atoms a hydrogen atom of which may be substituted by a halogen atom.

According to the present invention, there is provided a light emitting device including at least two electrodes, and a light emitting layer interposed between the electrodes, in which the light emitting layer contains the light emitting material.

A light emitting device using the light emitting material of the present invention has high luminous efficiency, stably emits light, and is provided at a low cost.

Further features of the present invention will become apparent from the following description of exemplary embodiments with reference to the attached drawings.

DESCRIPTION OF THE EMBODIMENTS

Figure 1A:
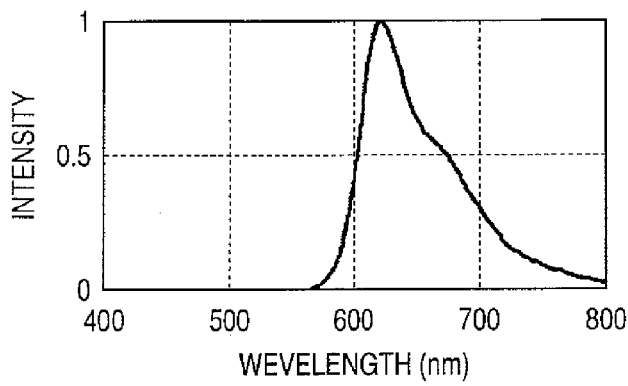
FIGS. 1A, 1B, and 1C are views showing the emission spectra of solutions of Exemplified Compounds 1014 to 1016 in toluene.

Hereinafter, the present invention will be described in detail.

First, the structure of an iridium coordination compound as a light emitting material of the present invention will be described.

Examples of the light emitting material of the present invention are shown below.

Exemplified Compound 1001
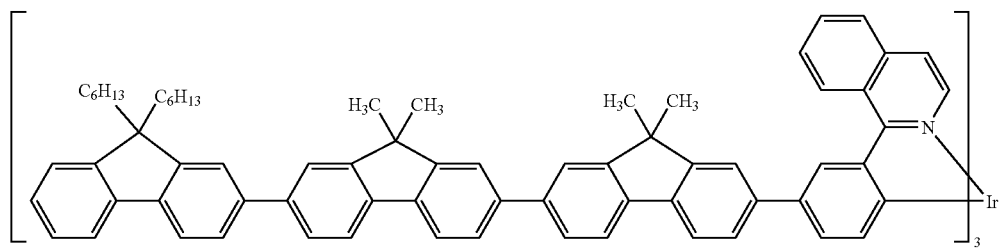
Exemplified Compound 1002
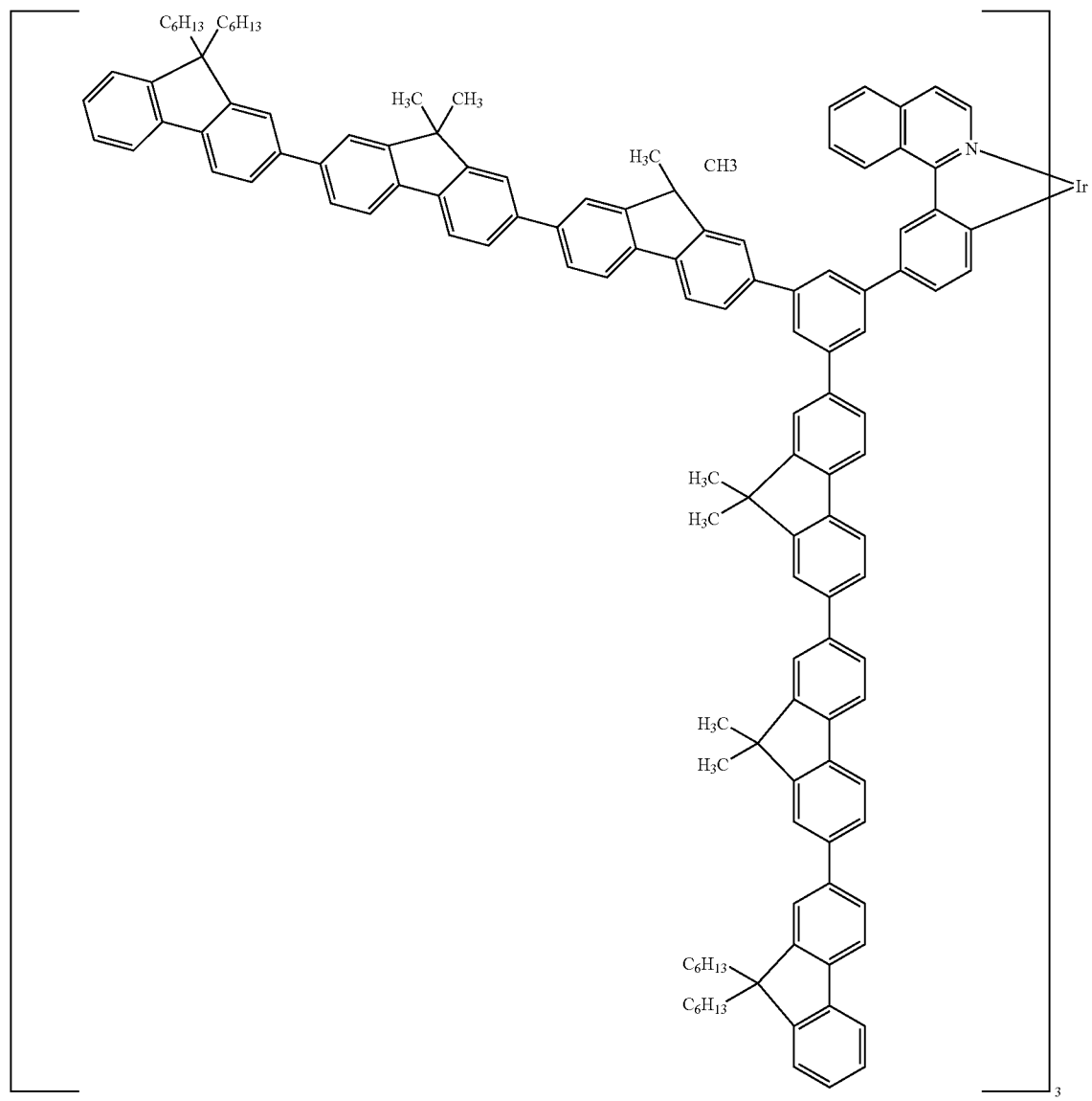

-continued
Exemplified Compound 1003
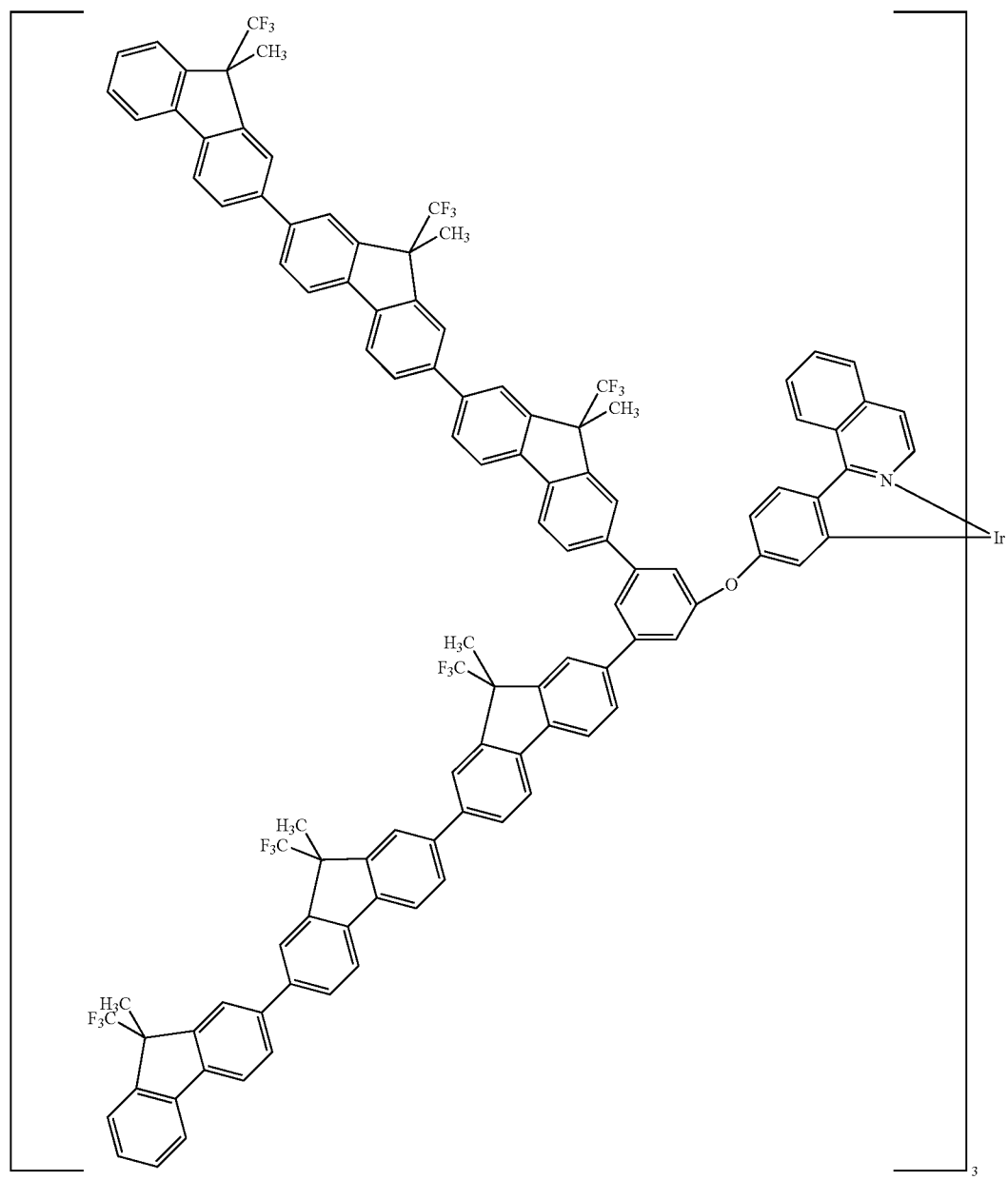
Exemplified Compound 1004
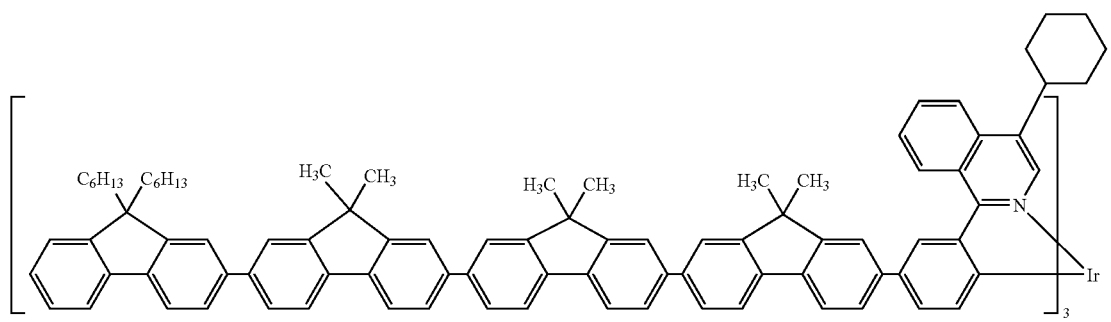

-continued
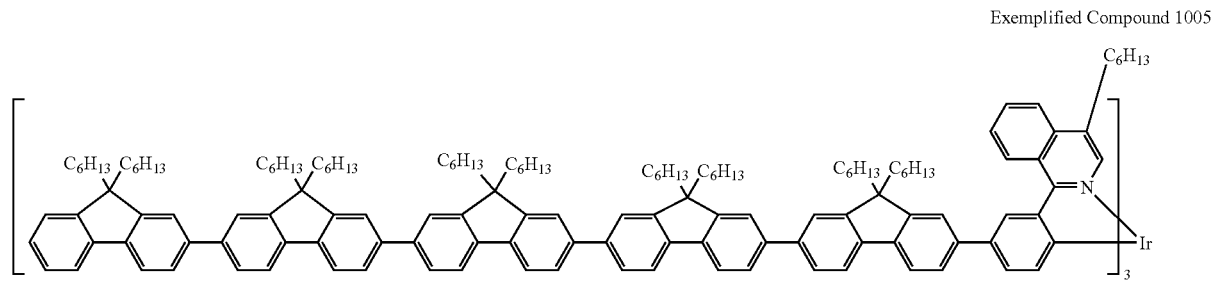
Exemplified Compound 1005
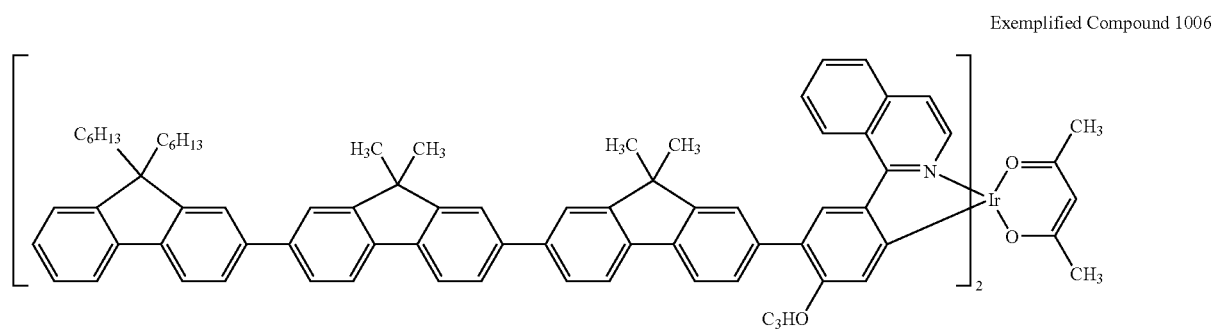
Exemplified Compound 1006
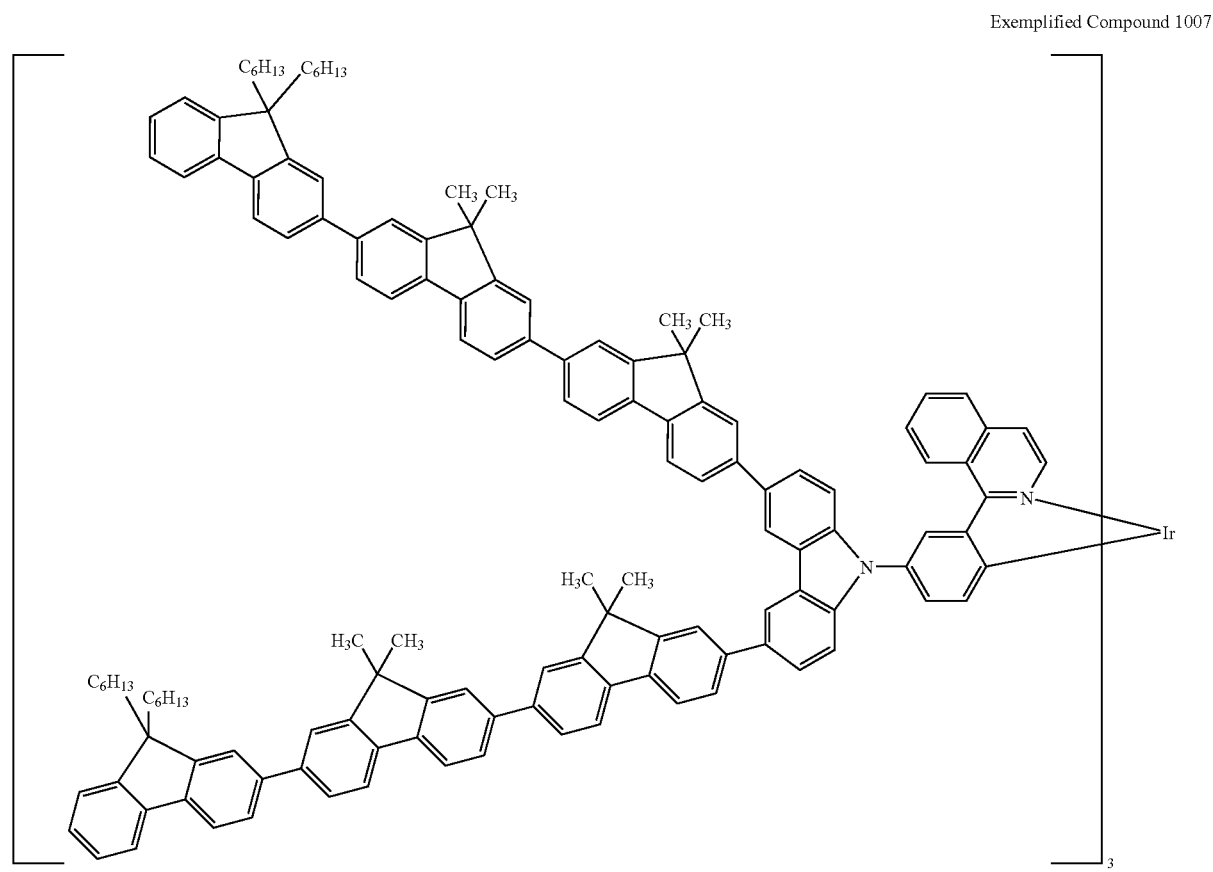
Exemplified Compound 1007

-continued

Exemplified Compound 1008

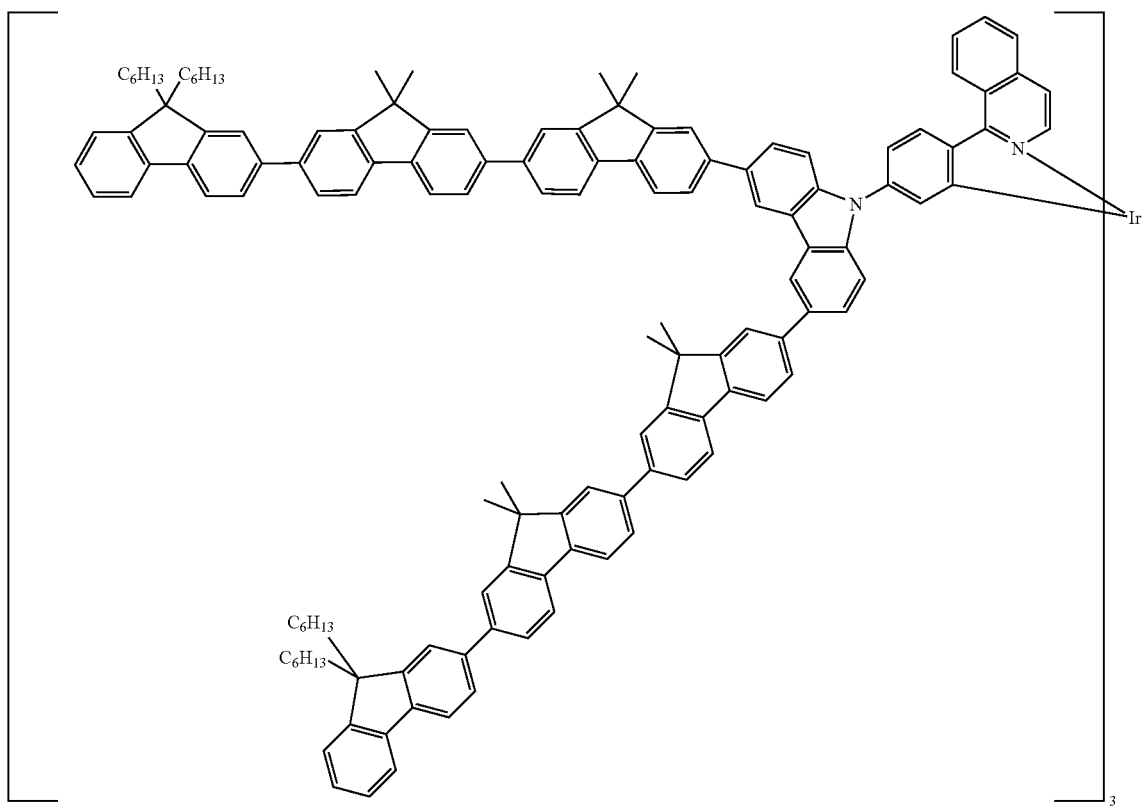

As shown in the above exemplified compounds, the light emitting material of the present invention is roughly formed of two parts: an iridium(phenylisoquinoline) part represented by the above partial structural formula (1) and a part formed of $R_1$ to $R_{10}$ placed around the iridium(phenylisoquinoline) part. The light emitting material of the present invention has such a molecular structure that substituents $R_1$ to $R_{10}$ including plural aromatic rings and an alkyl group are placed around an iridium(phenylisoquinoline) skeleton. The importance of the molecular structure as a light emitting material will be described below.

(1) The solubility of the light emitting material in a general organic solvent improves when $R_1$ to $R_{10}$ include a trifluoromethyl group, or a linear, branched, or cyclic alkyl or alkoxyl group having 2 or more carbon atoms. The production of a light emitting material having high solubility is indispensable to the production of an organic EL device by an application method. In a case where an EL device is produced by doping a carrier transportable host with the light emitting material of the present invention, when the host and the light emitting material largely differ from each other in solubility, there is a high possibility that the same kind of molecules agglomerate upon drying of a solution containing the host and the light emitting material after the application of the solution, so the quality of a film formed of the solution may deteriorate, or the performance of the device may reduce. It is important to impart sufficient solubility to each of the host and the light emitting material in order to avoid the foregoing phenomenon. Investigation conducted by the inventors of the present invention has revealed that sufficient solubility can be obtained when "$R_1$ to $R_{10}$ include a trifluoromethyl group, or a linear, branched, or cyclic alkyl or alkoxyl group having 2 or more carbon atoms."

(2) A substituent is introduced in such a manner that "the total number of benzene ring structures in $R_1$ to $R_{10}$ is 3 or more." The introduction of "a substituent including 3 or more benzene ring structures into any one of $R_1$ to $R_{10}$" is desirable. As a result, the iridium(phenylisoquinoline) part as a light emitting center is protected from its surroundings, whereby the production of a quenching path due to an intermolecular interaction is suppressed. In particular, a light emitting site density substantially reduces, so the concentration quenching of the light emitting material can be dissolved, and high luminous efficiency can be realized even when the concentration of the light emitting material is high. In general, a light emitting layer is formed of two components, that is, a host and a light emitting material in order that the concentration quenching of the light emitting material may be suppressed; in the case of the light emitting material (iridium coordination compound) of the present invention, a light emitting layer can be formed only of the light emitting material.

(3) Substituent sites including 3 or more benzene ring structures in $R_1$ to $R_{10}$ each have high carrier transporting property. In such case, the iridium coordination compound of the present invention is a multifunctional light emitting material bringing together carrier transporting property and strong light emitting characteristics.

(4) Iridium(phenylisoquinoline) as a light emitting center is a red phosphorescence emitting center. Unsubstituted $Ir(piq)_3$ is a red light emitting material having a luminous wavelength of 620 nm; the light emission peak wavelength of the material fluctuates depending on a substituent, and the material emits red phosphorescence having a peak at a wavelength of 600 nm or more to 650 nm or less with high efficiency. When a substituent including 3 or more benzene ring structures is introduced into the iridium coordination compound of the present invention, it is important for the substituent not to inhibit the emission of red phosphorescence. The case where the substituent receives the light emission energy of the iridium(phenylisoquinoline) site by energy transfer is not preferable because light emitted from the iridium(phenylisoquinoline) site is quenched. It is desirable that a substituent of the present invention neither absorb the light emission energy of the iridium(phenylisoquinoline) site nor inhibit the emission of red phosphorescence.

(5) When an aromatic ring group is directly bonded to the iridium(phenylisoquinoline) site, the π-electron conjugated system of the entire ligands expands, so light emission energy may reduce (the luminous wavelength of the light emitting material may lengthen). When the luminous wavelength becomes excessively long (650 nm or more), the material cannot be a preferable red light emitting material because the visual sensitivity of a human being to the wavelength reduces. In this case, the luminous wavelength must be shortened. Investigation conducted by the inventors of the present invention has revealed that the luminous wavelength can be shortened by introducing an electron-withdrawing substituent into any one of the substituents $R_1$ to $R_4$ on the phenyl group side of the iridium(phenylisoquinoline) site. An F atom, a trifluoromethyl group, a trifluoromethoxy group, or the like is effective in shortening the luminous wavelength, and any such substituent can be appropriately introduced according to the luminous wavelength.

Desirable examples of the light emitting material of the present invention include compounds each represented by the following structural formula (2) or (3).

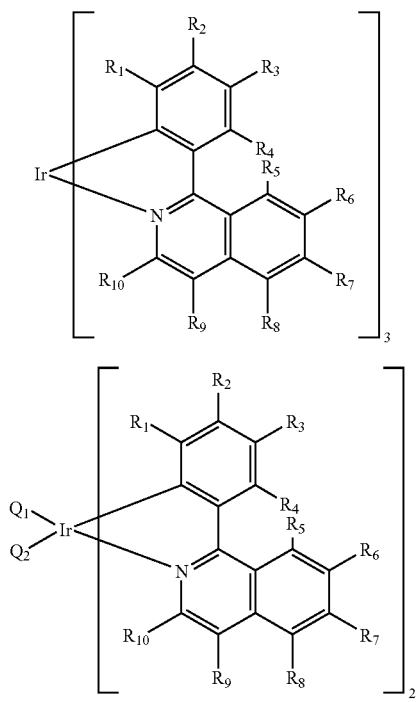

Q1 and Q2 may be bonded to each other, and are each selected form the following structural formulae (4):

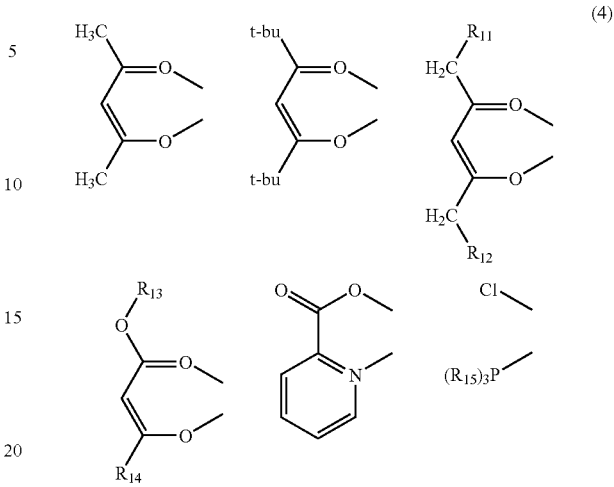

wherein $R_{11}$ to $R_{14}$ each represent a hydrogen atom, an alkyl group, or a substituent having 3 or more benzene ring structures, and $R_{15}$ represents an alkyl or alkoxyl group having 1 or more to 5 or less carbon atoms, or a phenyl group which may be substituted by an alkyl or alkoxyl group that has 1 or more to 5 or less carbon atoms and that may be substituted by a halogen atom.

A compound in which at least one of $R_1$ to $R_{10}$ includes a structure represented by any one of the following partial structural formulae (5) to (7) can also be given as a desirable example.

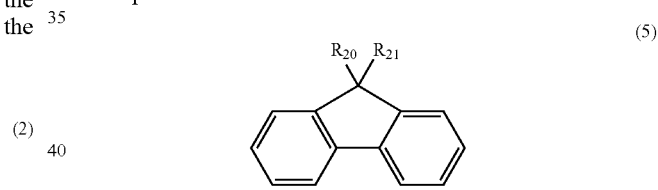

$R_{20}$ and $R_{21}$ are each independently selected from a trifluoromethyl group, or a linear, branched, or cyclic alkyl group having 2 or more carbon atoms a hydrogen atom of which may be substituted by a halogen atom.

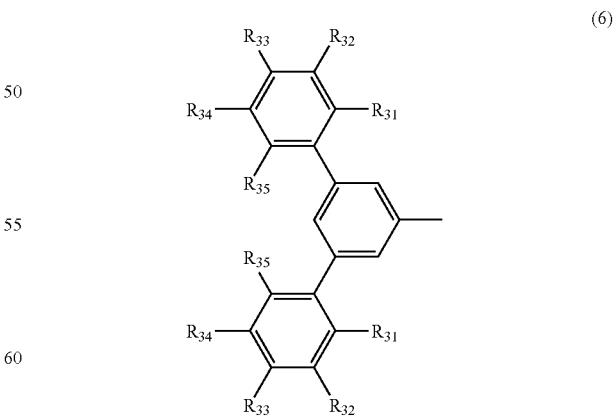

At least one of $R_{31}$ to $R_{35}$ is a trifluoromethyl group, or a linear, branched, or cyclic alkyl group having 2 or more carbon atoms a hydrogen atom of which may be substituted by a halogen atom.

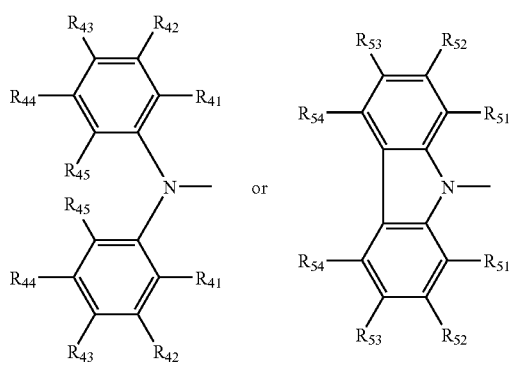

(7)

At least one of $R_{41}$ to $R_{45}$ or $R_{51}$ to $R_{54}$ is a trifluoromethyl group, or a linear, branched, or cyclic alkyl group having 2 or more carbon atoms a hydrogen atom of which may be substituted by a halogen atom.

Also, a compound which includes a fluorine atom, a trifluoromethyl group, or a trifluoromethoxy group in $R_1$ to $R_4$ can be a desirable example.

It is desirable that the light emitting material emit red light having a light emission peak at a wavelength of 600 nm or more to 650 nm or less. Further, the light emitting material has another light emission peak at a wavelength of 400 nm or more to 600 nm or less.

Further examples of the light emitting material of the present invention are shown below.

Exemplified Compound 1010

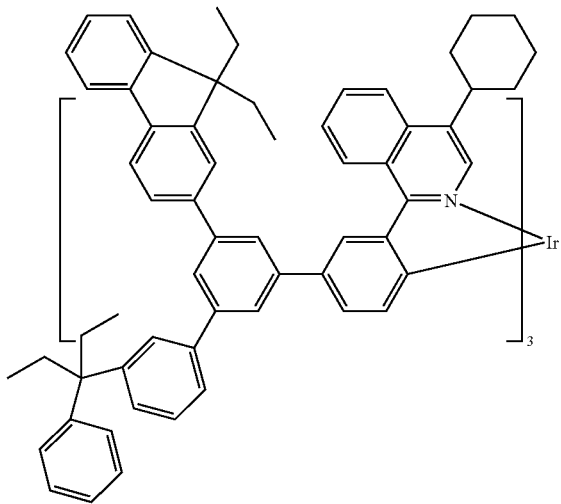

Exemplified Compound 1011

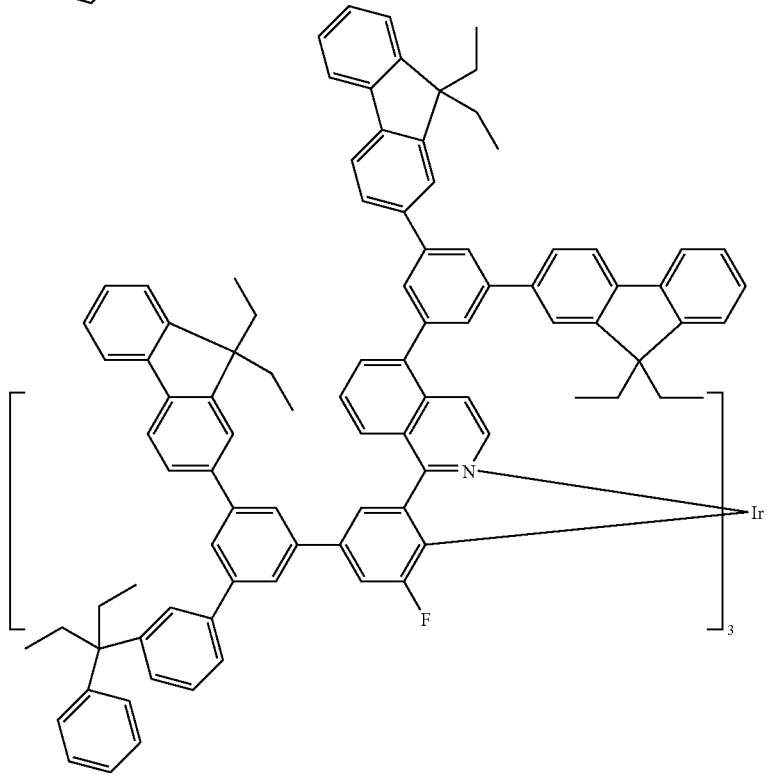

-continued
Exemplified Compound 1012
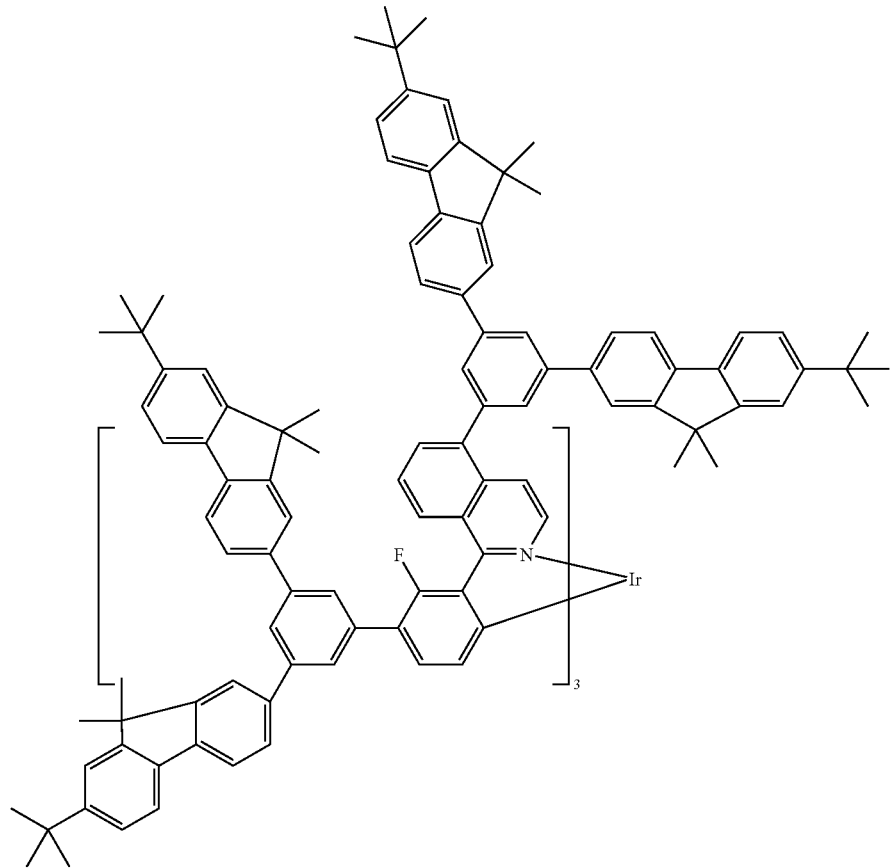
Exemplified Compound 1013
Exemplified Compound 1013-1
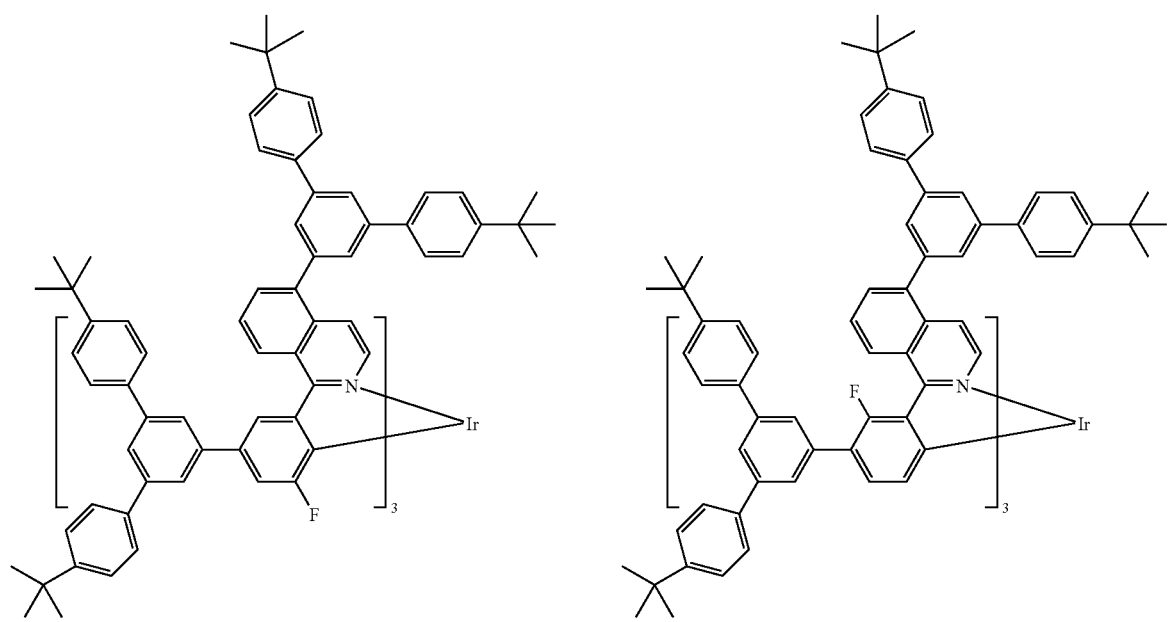

-continued
Exemplified Compound 1014
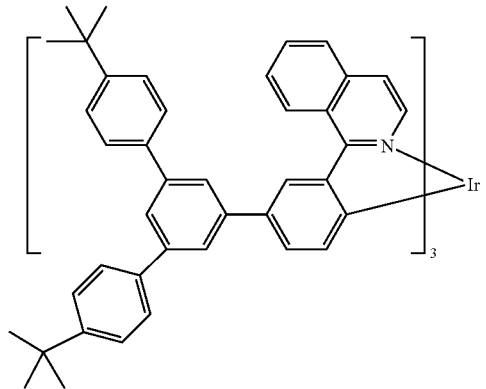
Exemplified Compound 1014
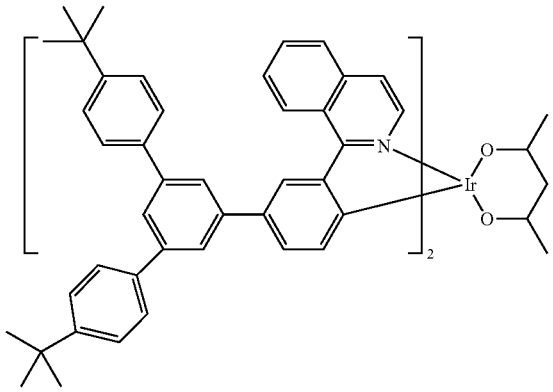
Exemplified Compound 1016
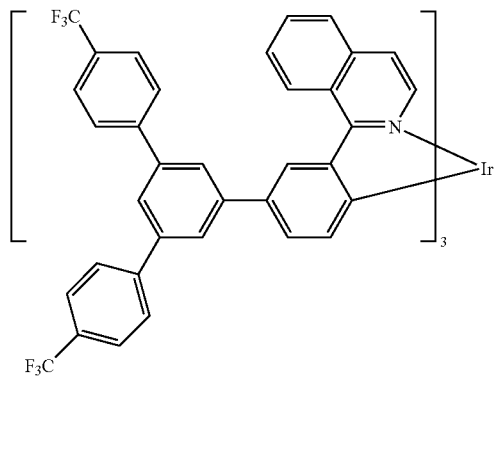
Exemplified Compound 1017
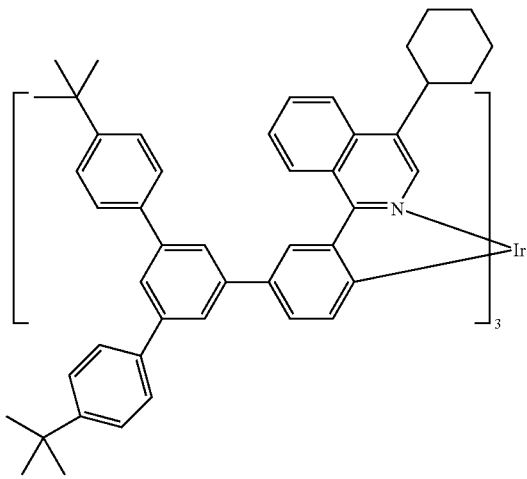
Exemplified Compound 1018
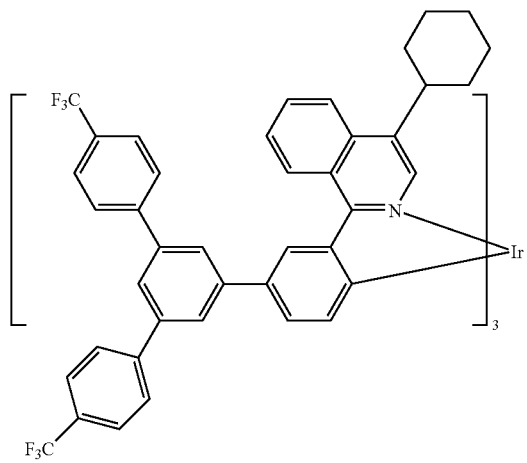
Exemplified Compound 1019
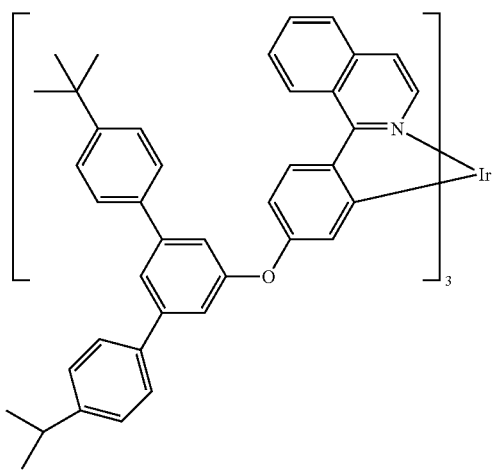

-continued
Exemplified Composition 1020
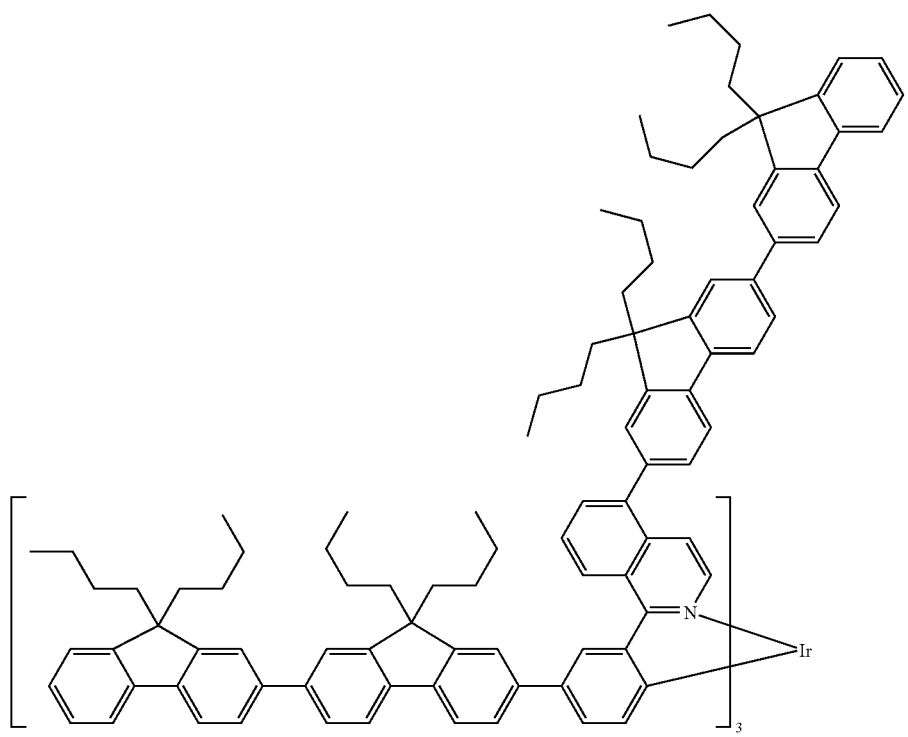
Exemplified Compositiion 1021
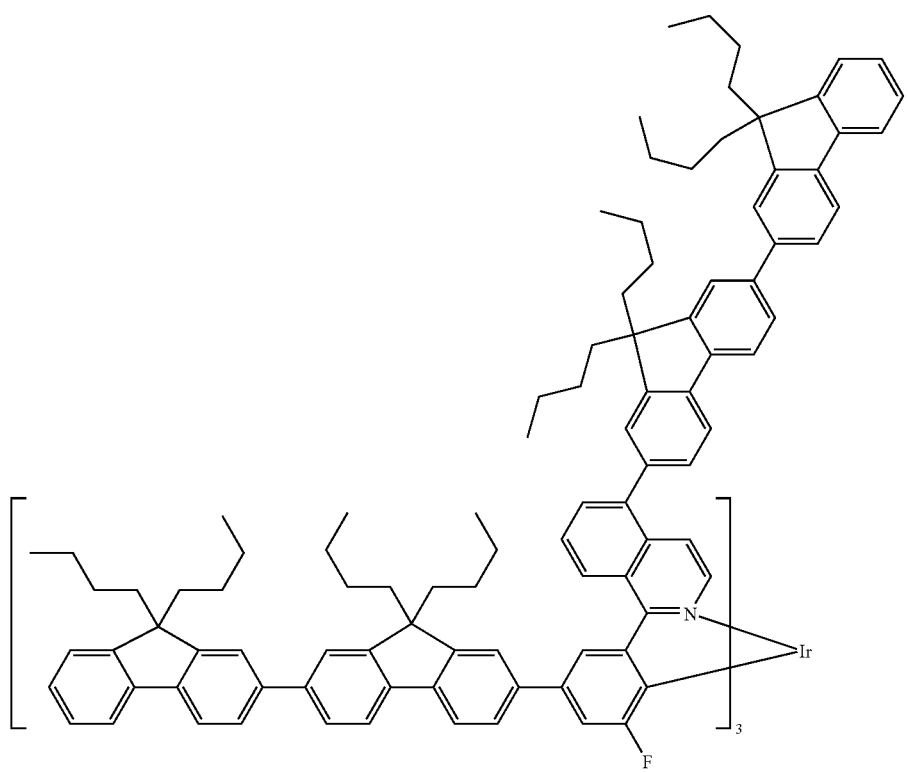

-continued
Exemplified Compound 1022
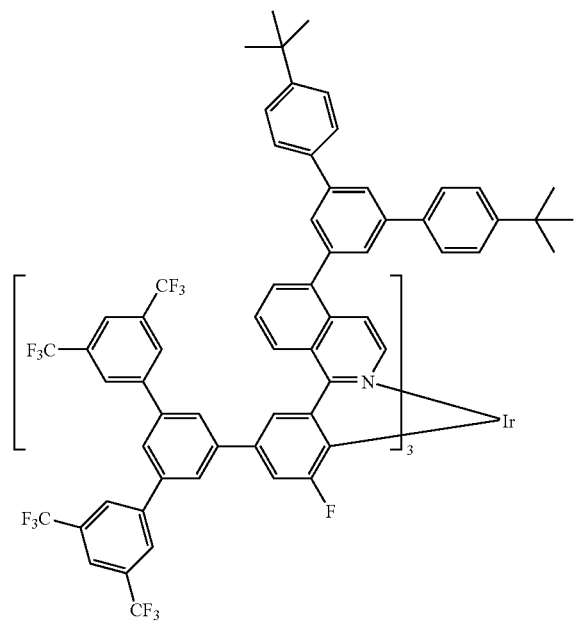
Exemplified Compound 1023
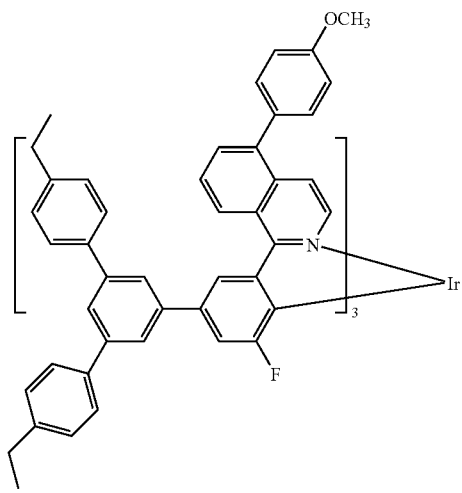
Exemplified Compound 1024
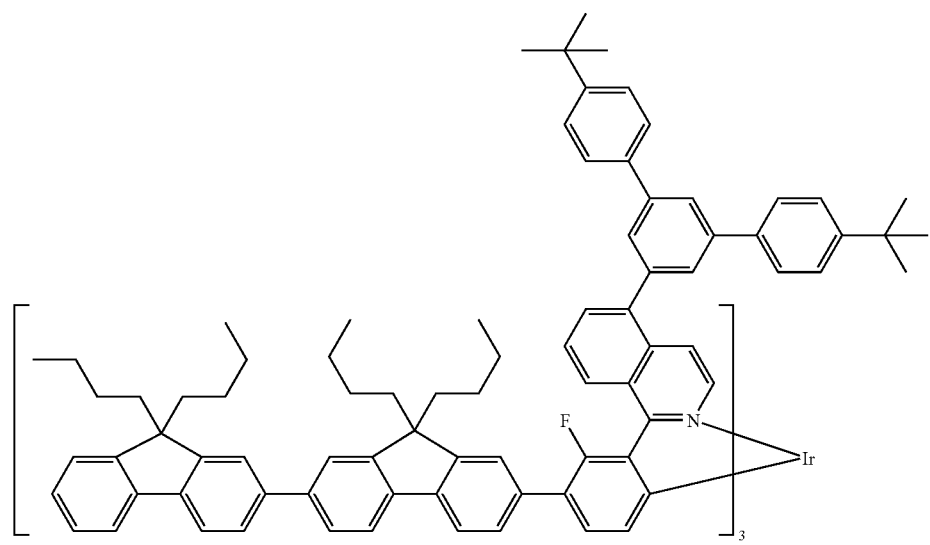

-continued
Exemplified Composition 1025
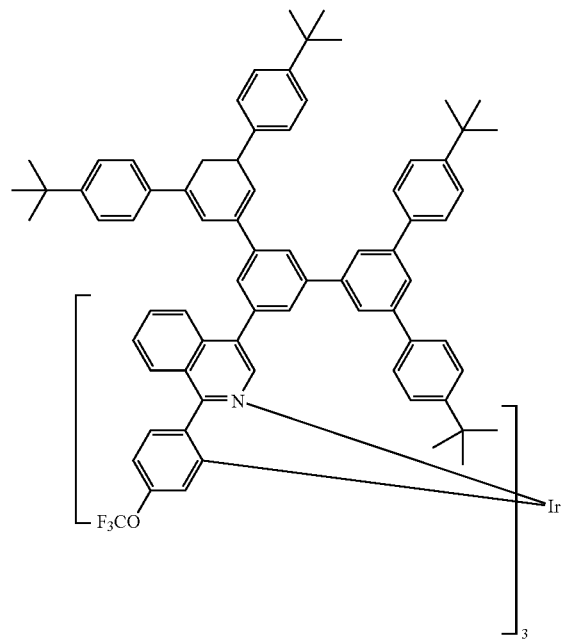
Exemplified Composition 1026
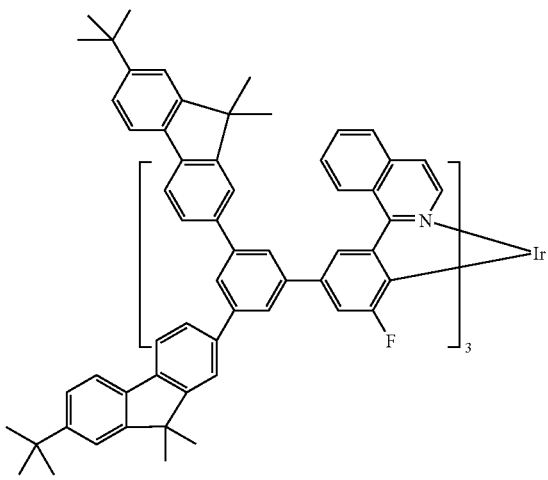
Exemplified Composition 1027
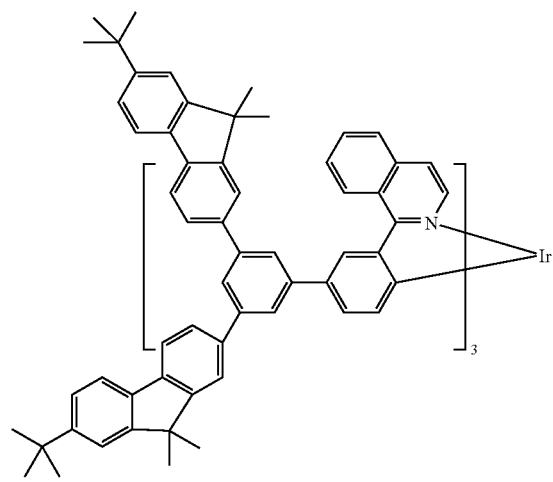
Exemplified Composition 1028
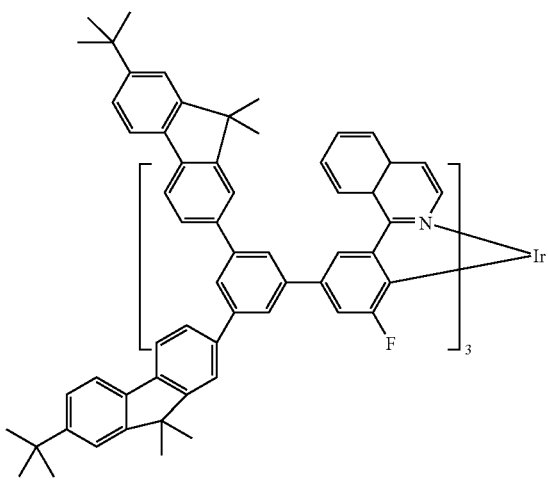

-continued
Exemplified Compound 1029
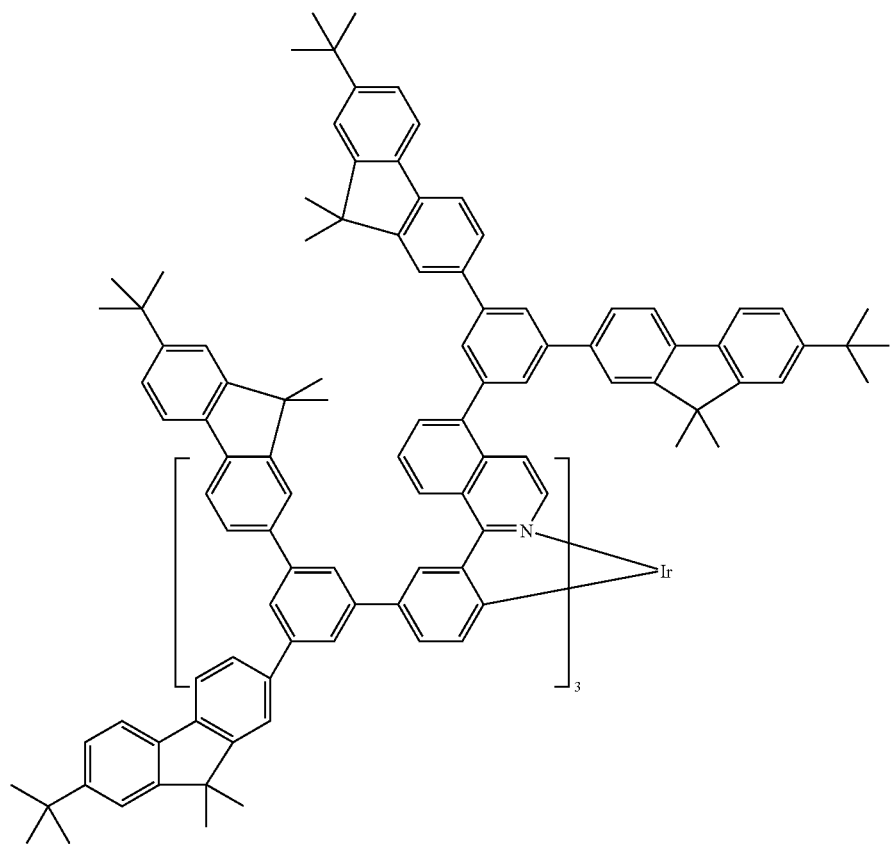
Exemplified Compound 1030
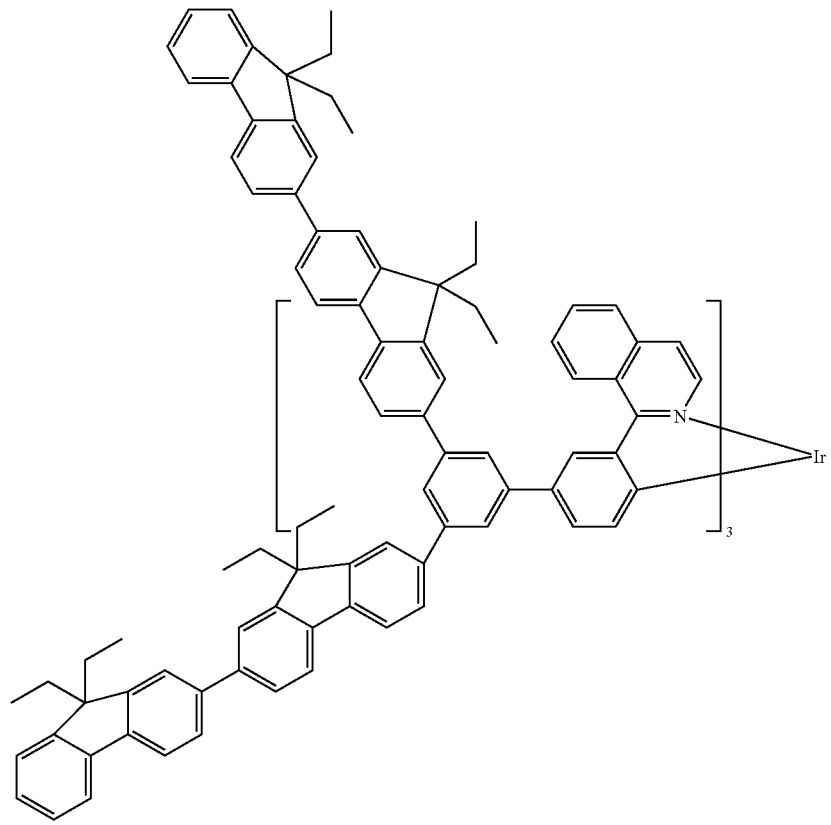

-continued
Exemplified Compound 1031
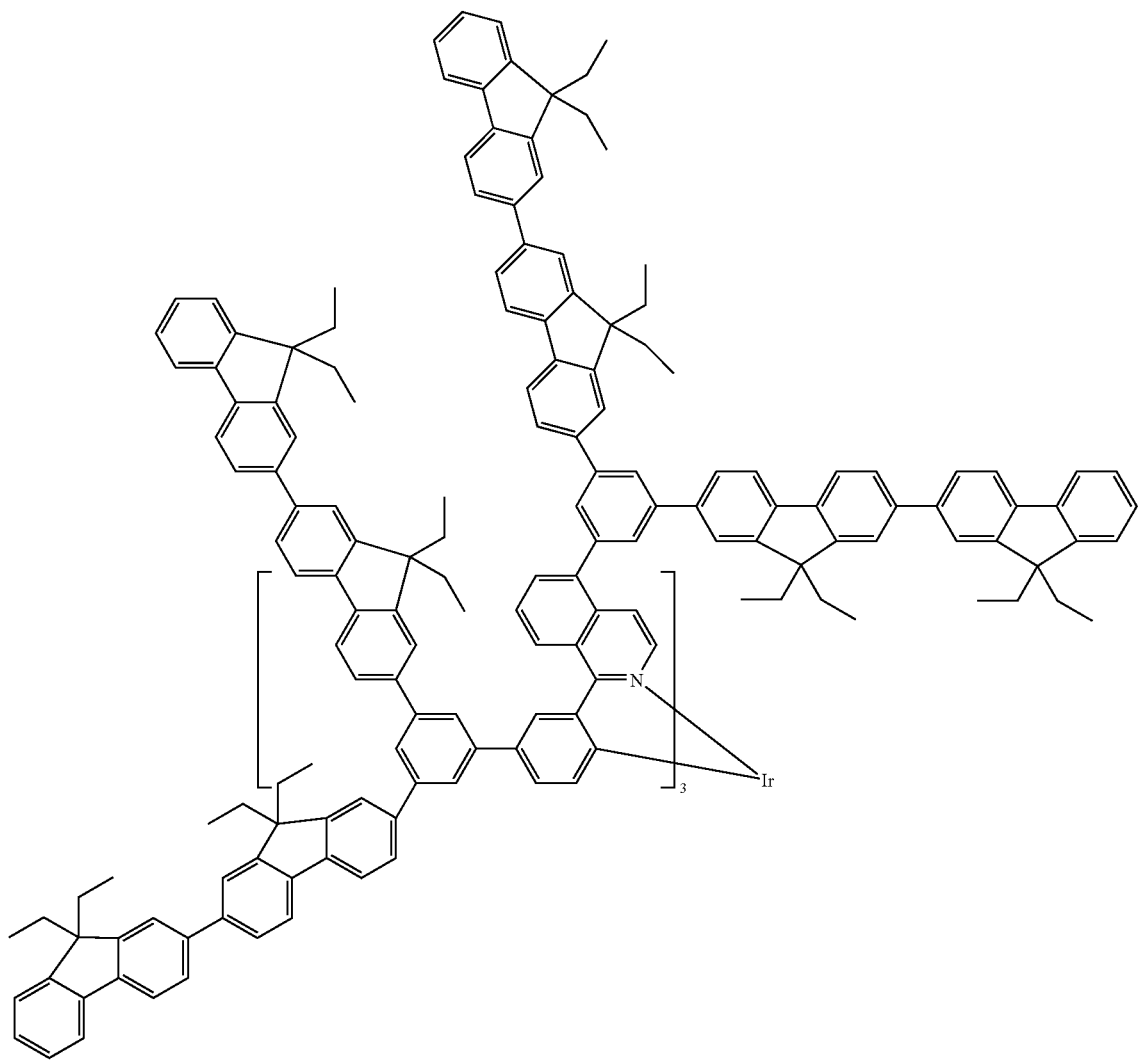

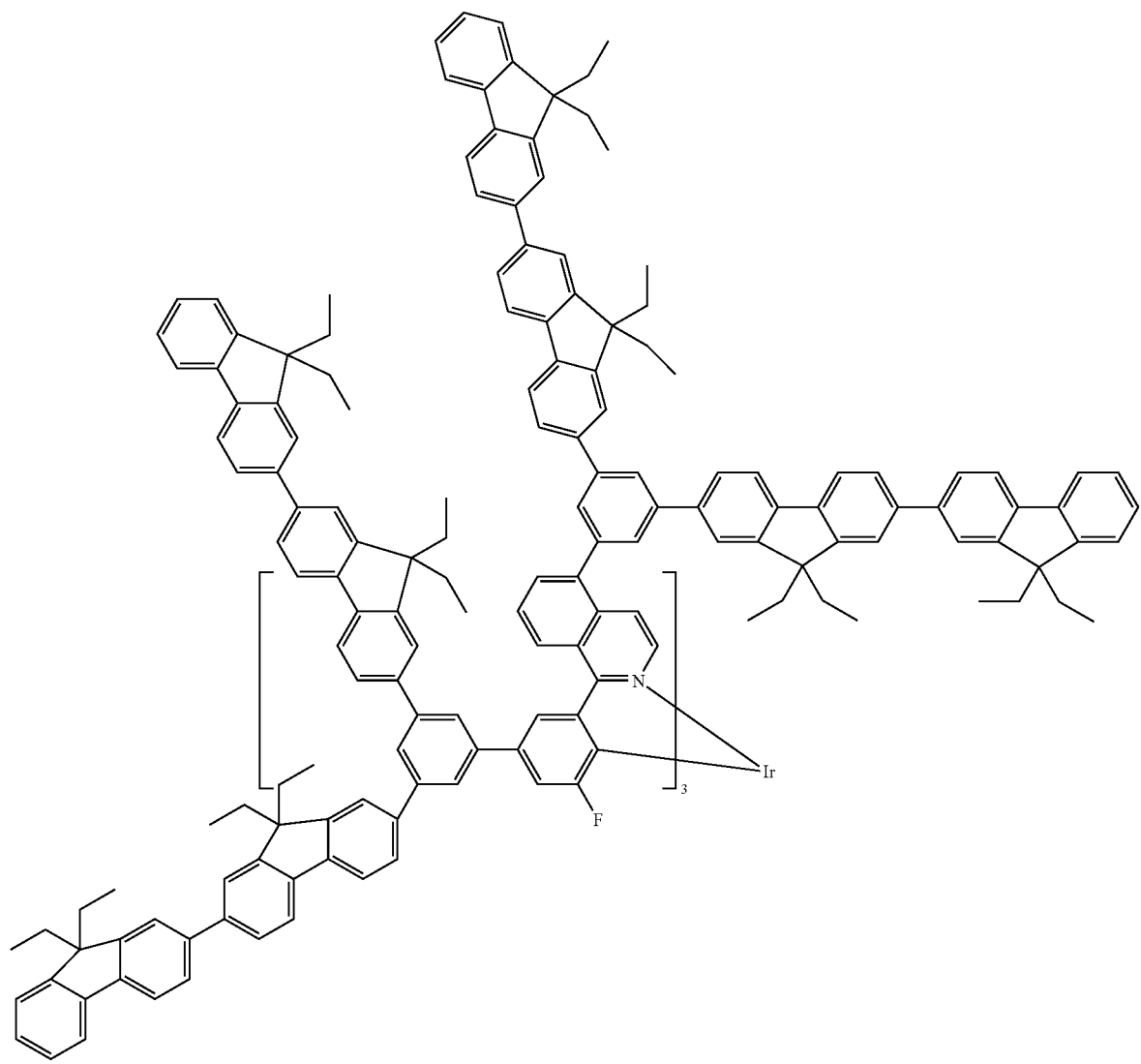
Exemplified Compound 1032

-continued
Exemplified Compound 1033
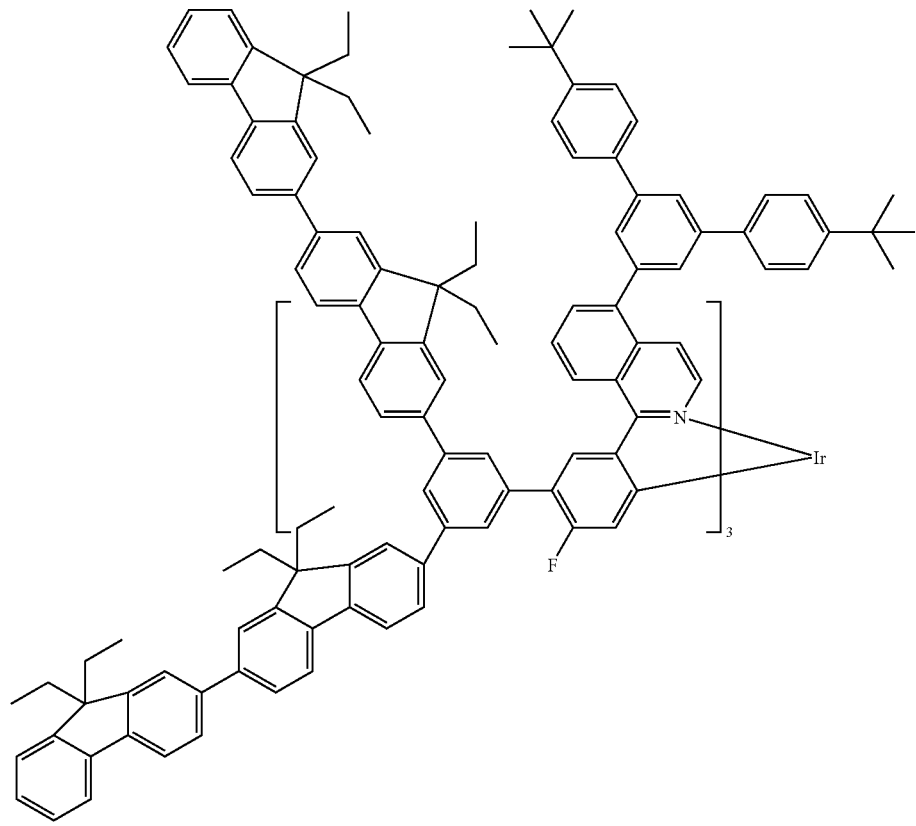
Exemplified Compound 1034
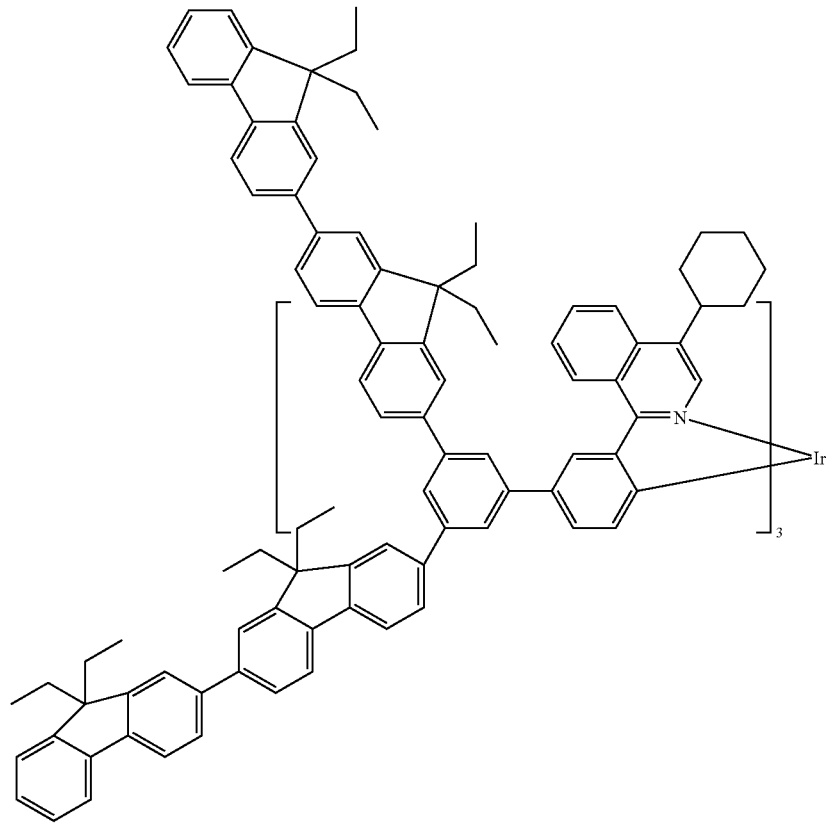

Exemplified Compound 1040
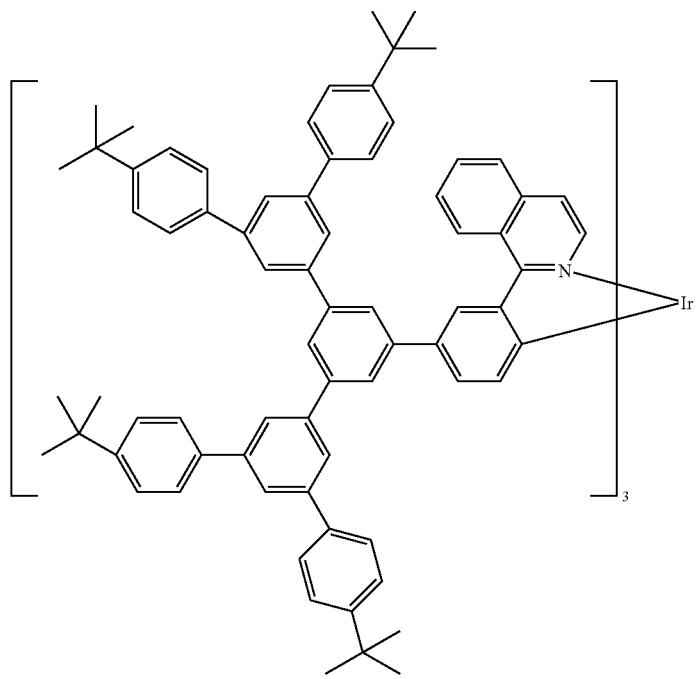
Exemplified Compound 1041
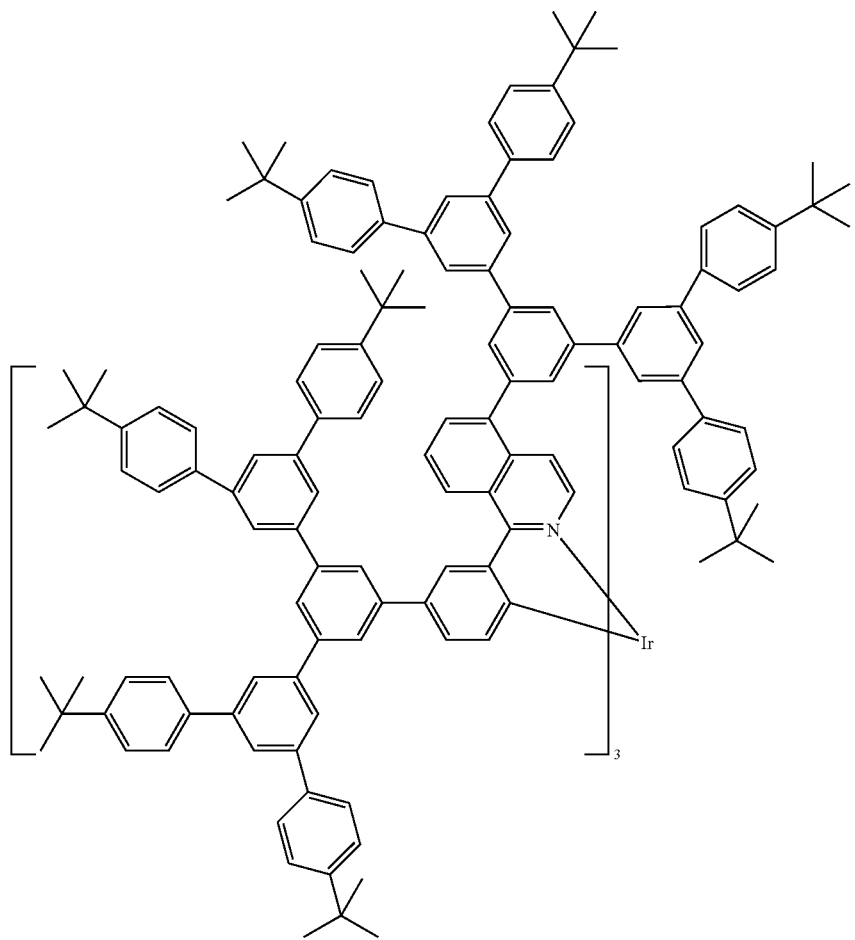

Exemplified Compound 1042
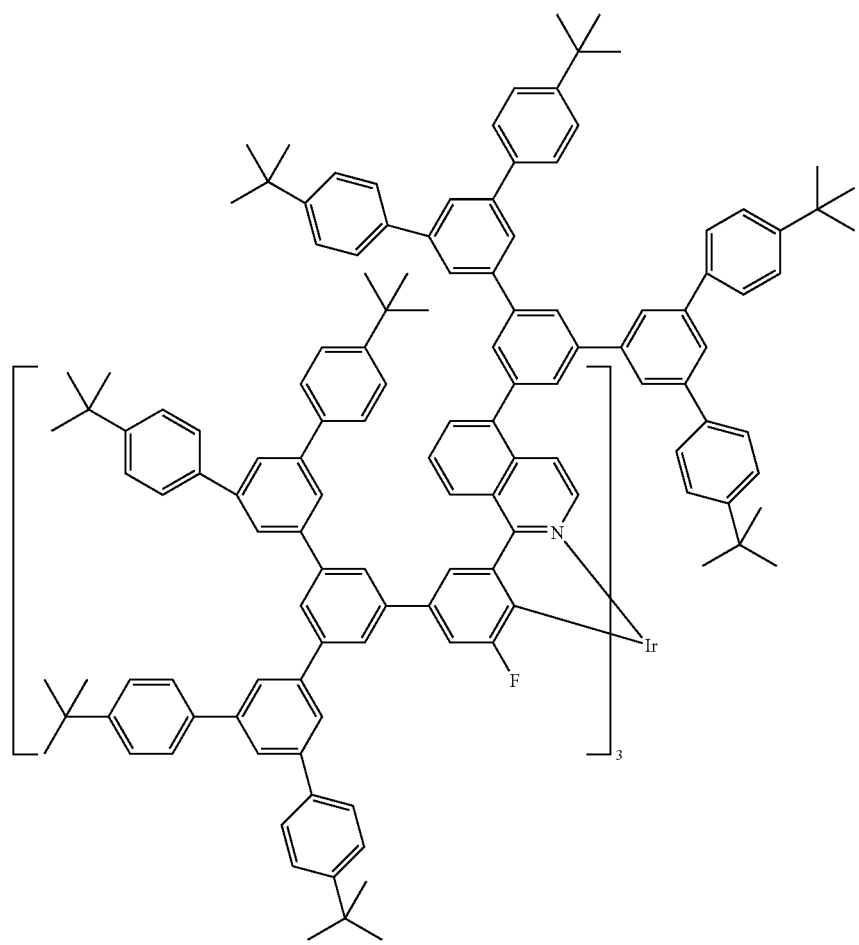
Exemplified Compound 1043
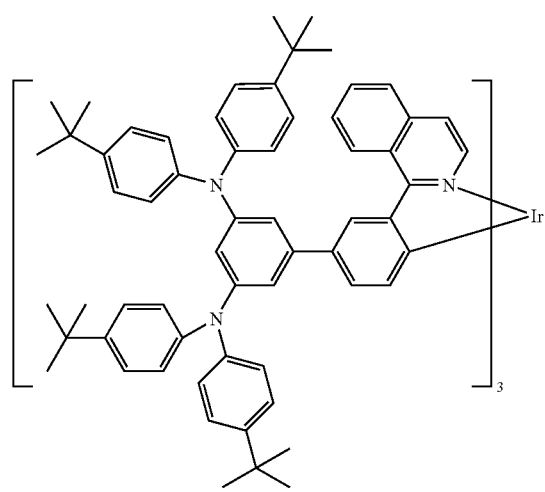
Exemplified Compound 1044
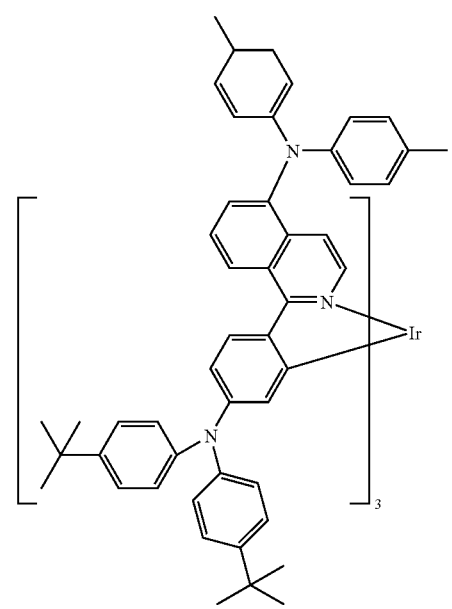

-continued
Exemplified Compound 1045
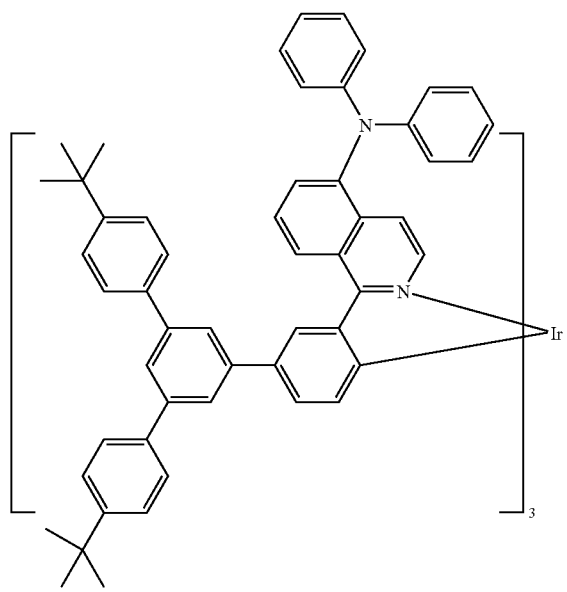
Exemplified Compound 1046
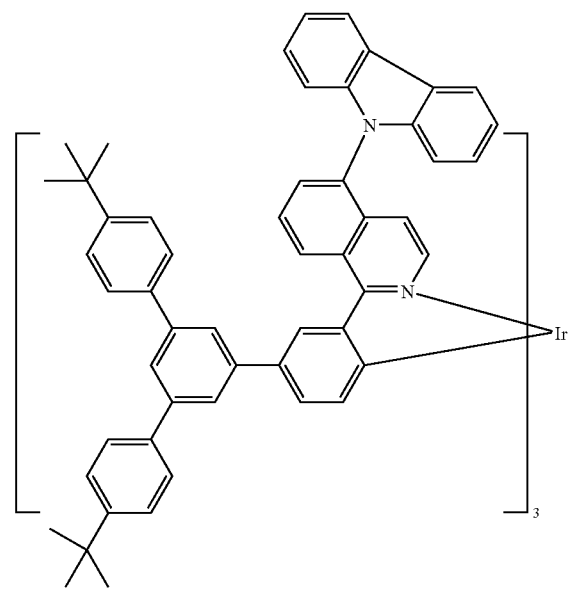
Exemplified Compound 1047
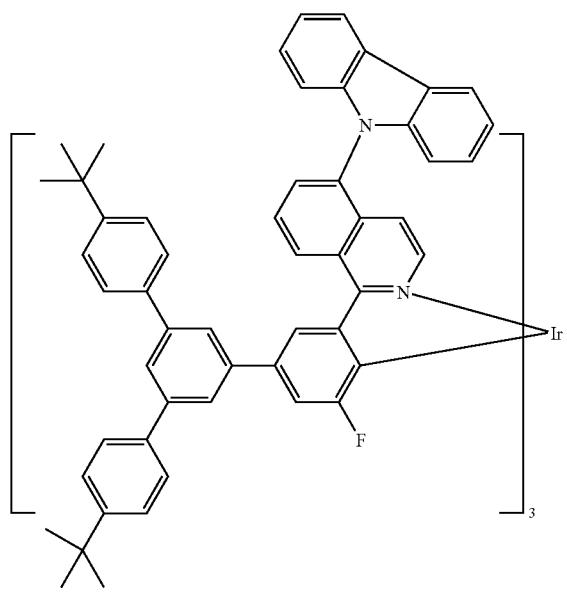
Exemplified Compound 1050
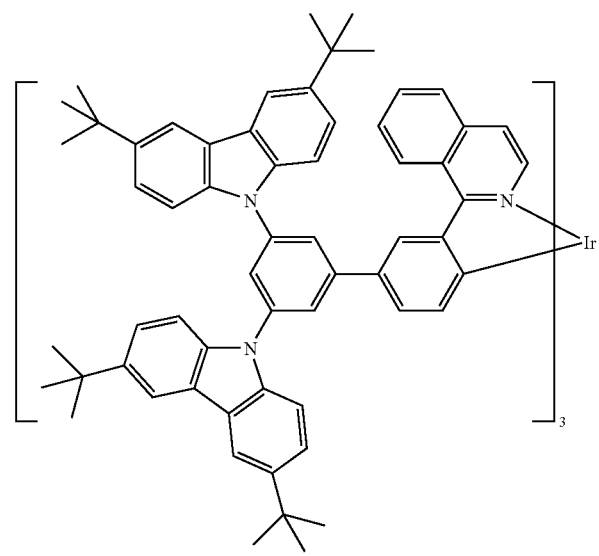

Exemplified Compound 1051
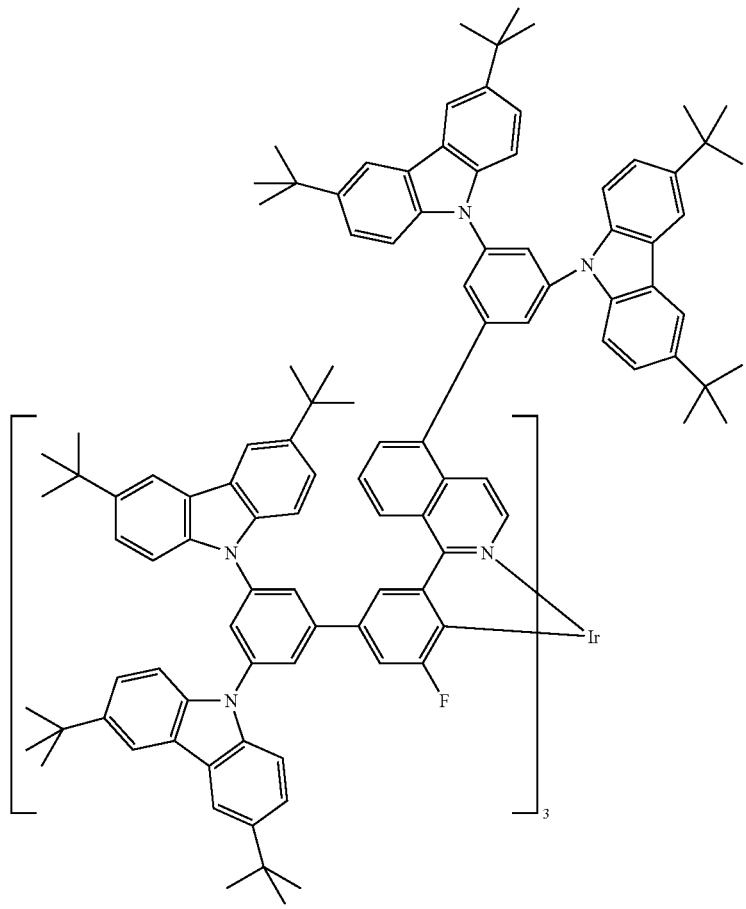
Exemplified Compound 1052
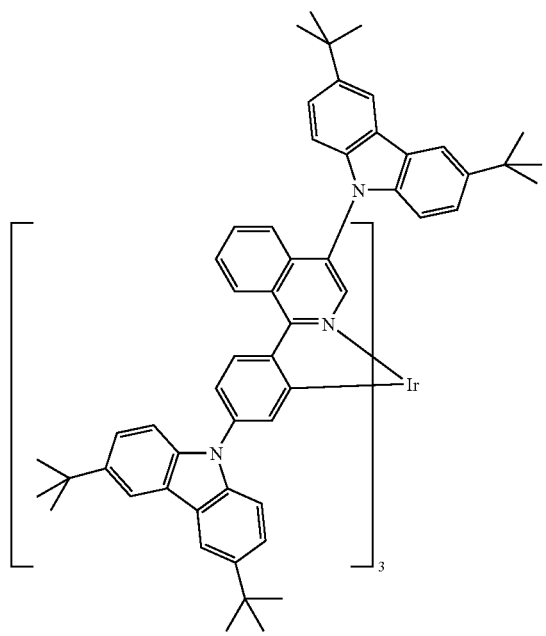
Exemplified Compound 1053
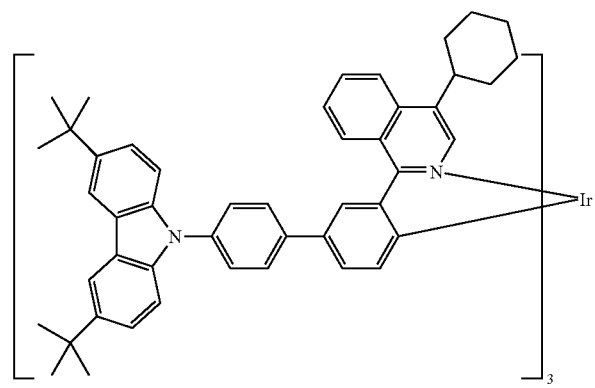

-continued

Exemplified Compound 1054

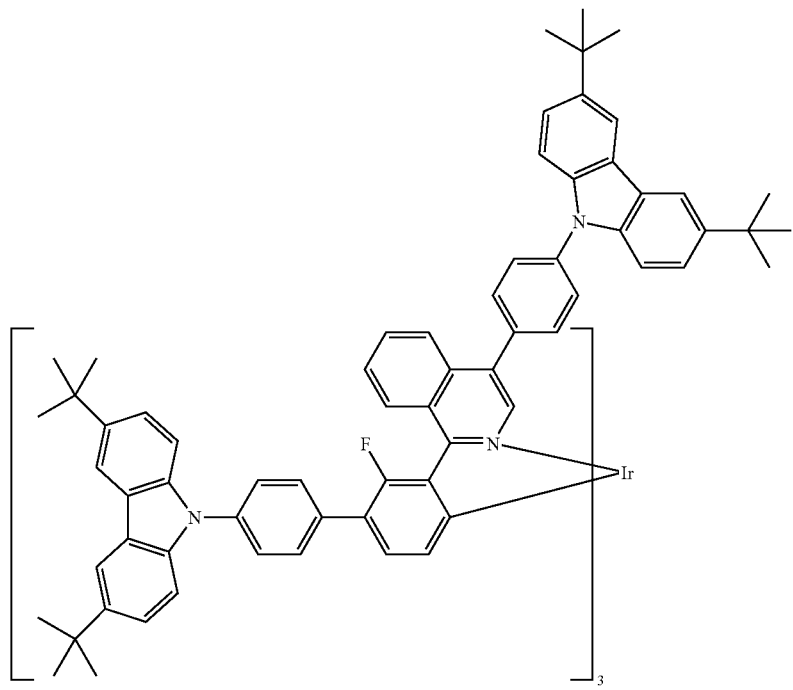

Further, examples of the light emitting material of the present invention are shown in the following tables. In the following tables, the name of a substituent including a fluorenyl group is represented by combining an abbreviated name shown in any one of 1FL1 to 1FL6, 2FL1 to 2FL7, 3FL1 to 3FL6, 4FL1 to 4FL6, 5FL1 to 5FL6 and 10FL1 to 20FL6 and the abbreviated name of a linking group shown in C1 to C11. In addition, the abbreviated name of an addition ligand represents a structure shown in acac to pic.

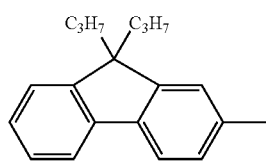

1FL1

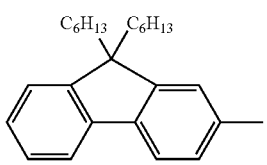

1FL2

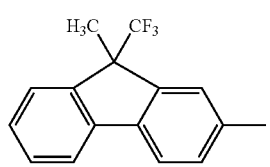

1FL3

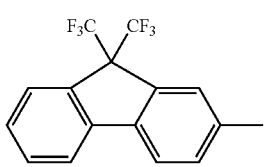

1FL4

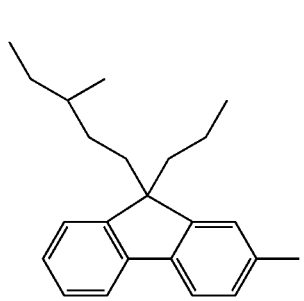

1FL5

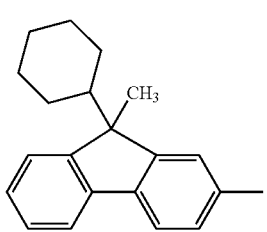

1FL6

-continued
2FL1
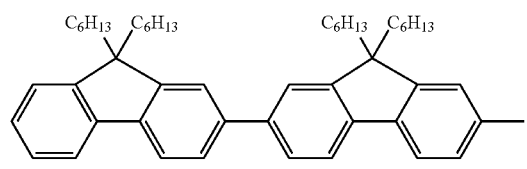
2FL2
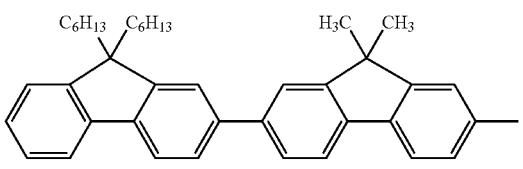
2FL3
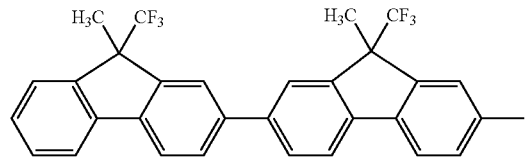
2FL4
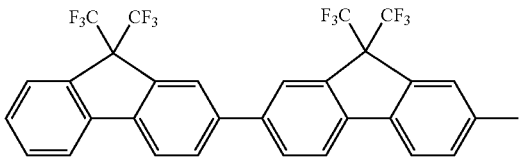
2FL5
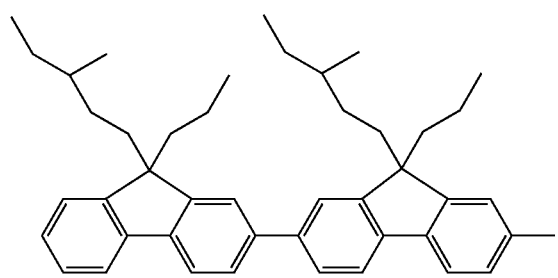
2FL6
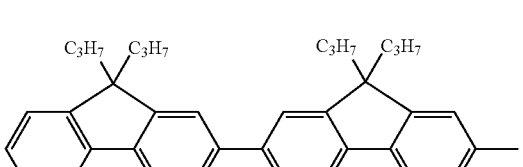
2FL7
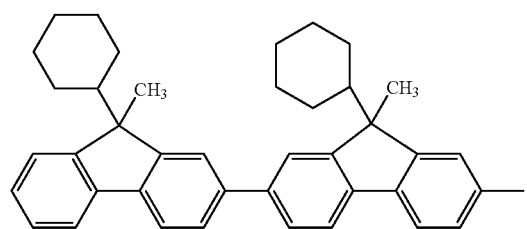
3FL1
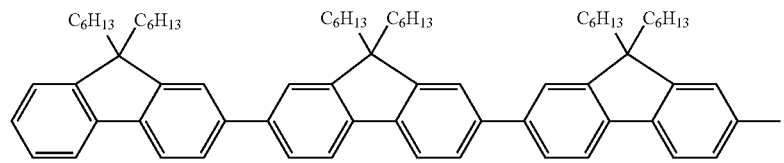
3FL2
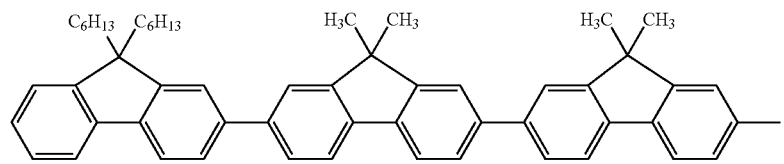
3FL3
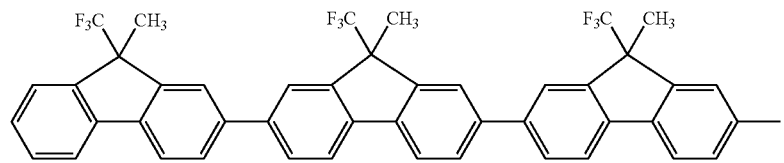
3FL4
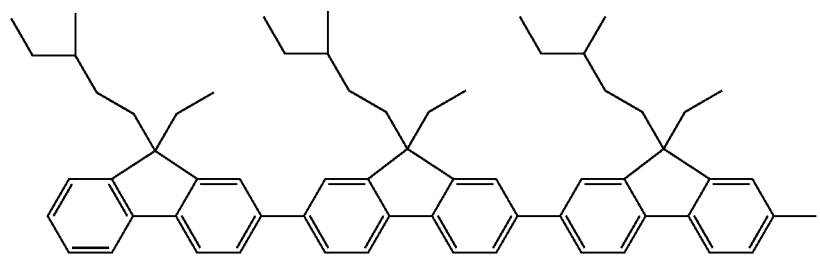

-continued
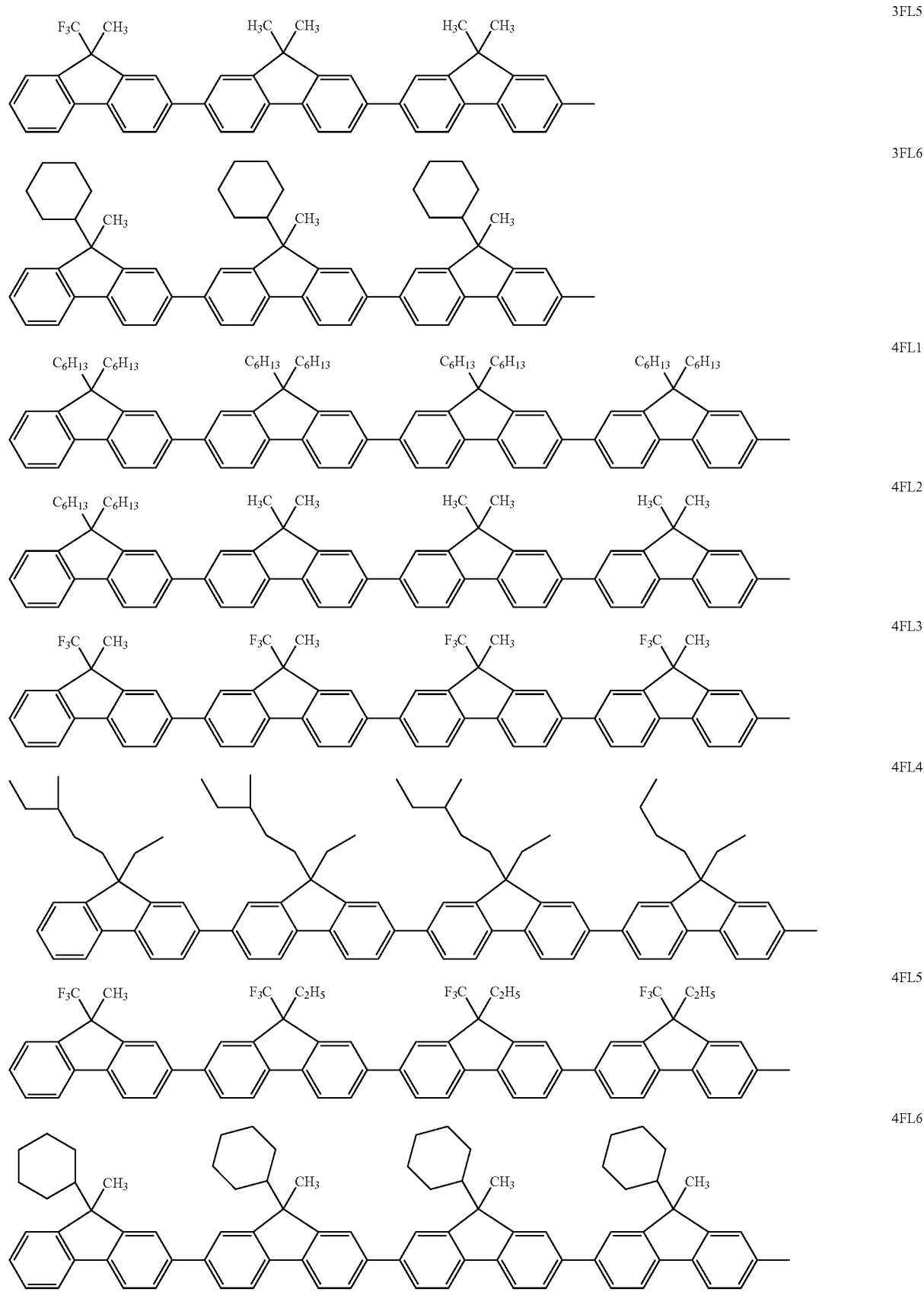

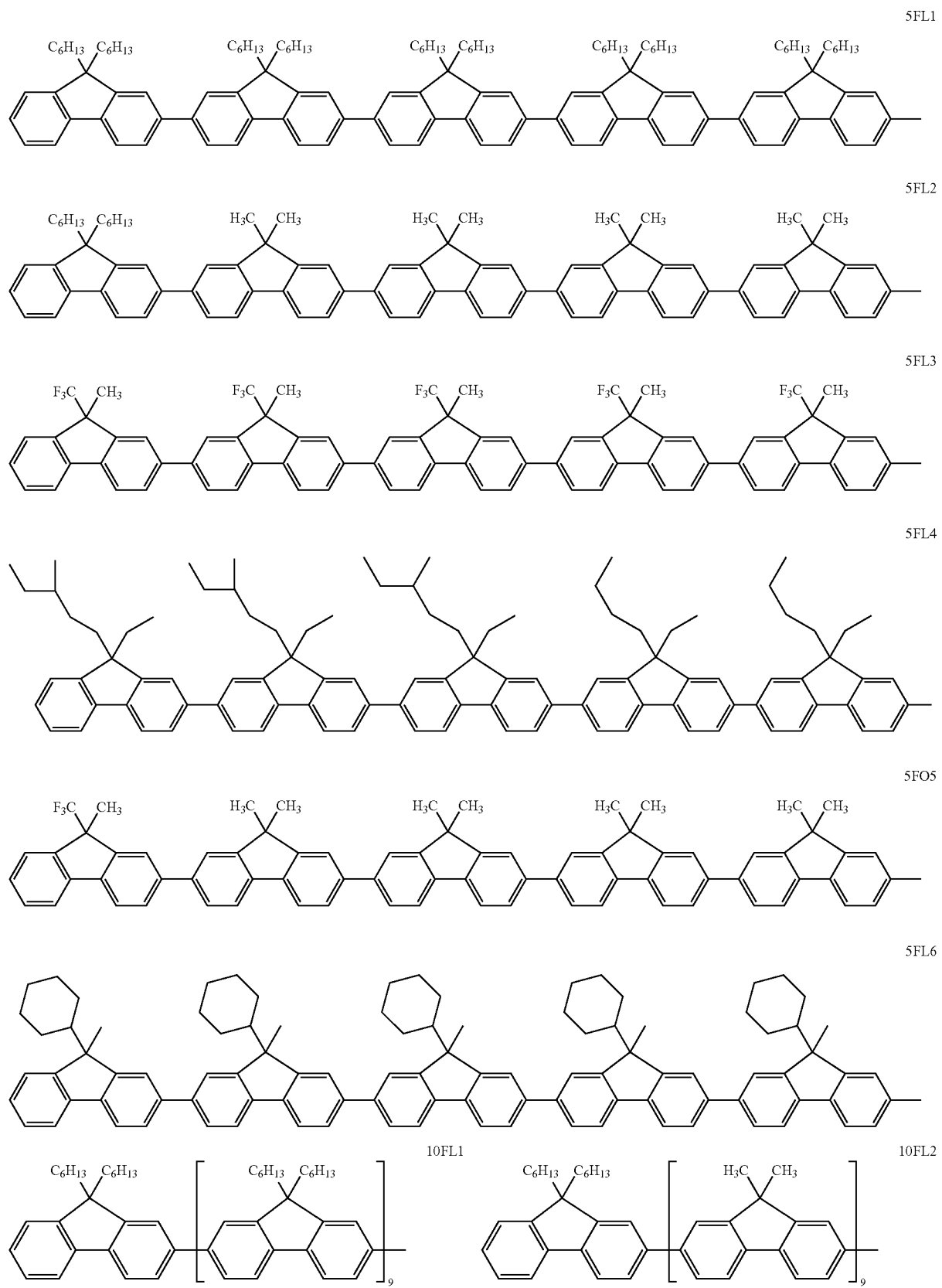

-continued
10FL3
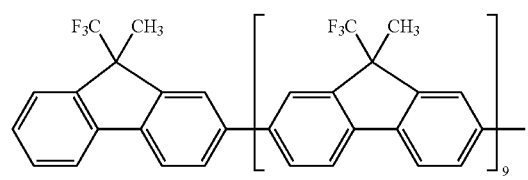
10FL4
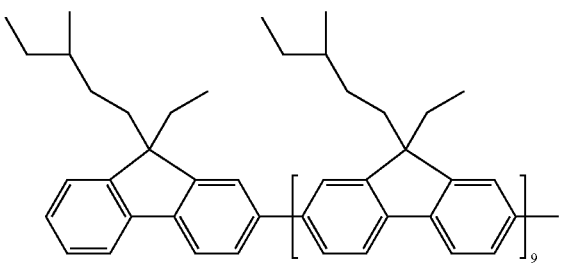
10FL5
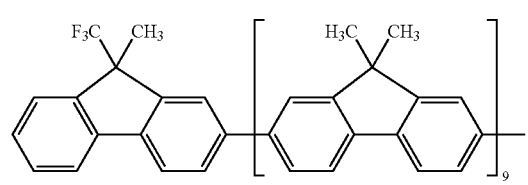
10FL6
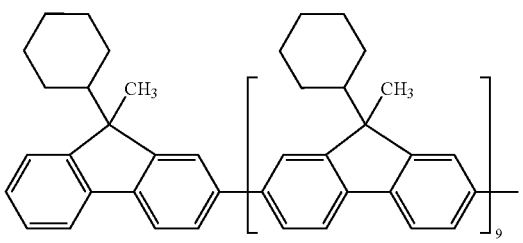
20FL1
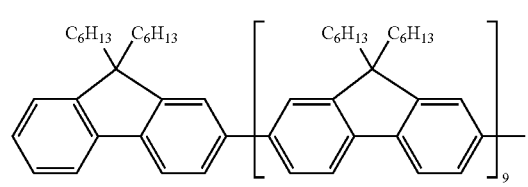
20FL2
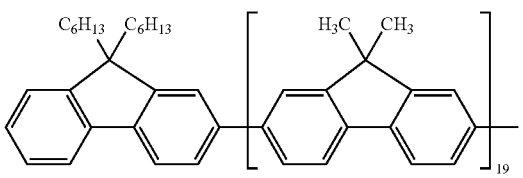
20FL3
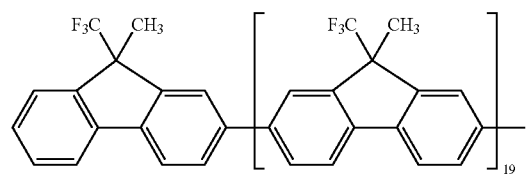
20FL4
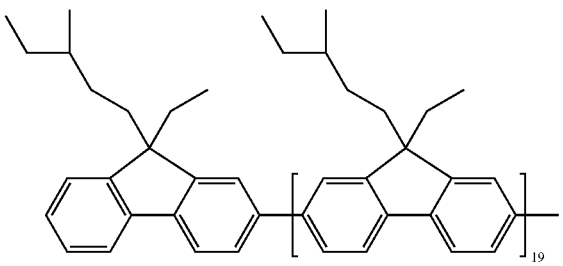
20FL5
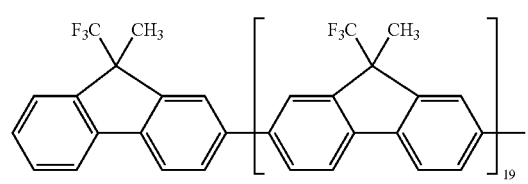
20FL6
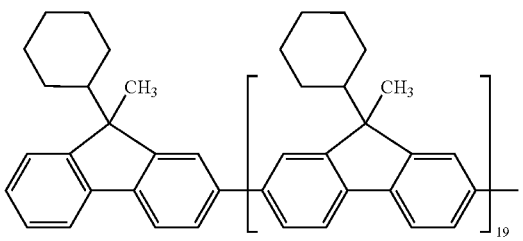
C1
nFL
C2
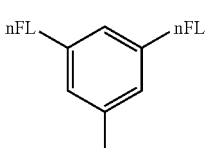
C3
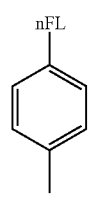
C4
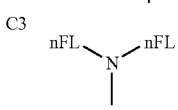

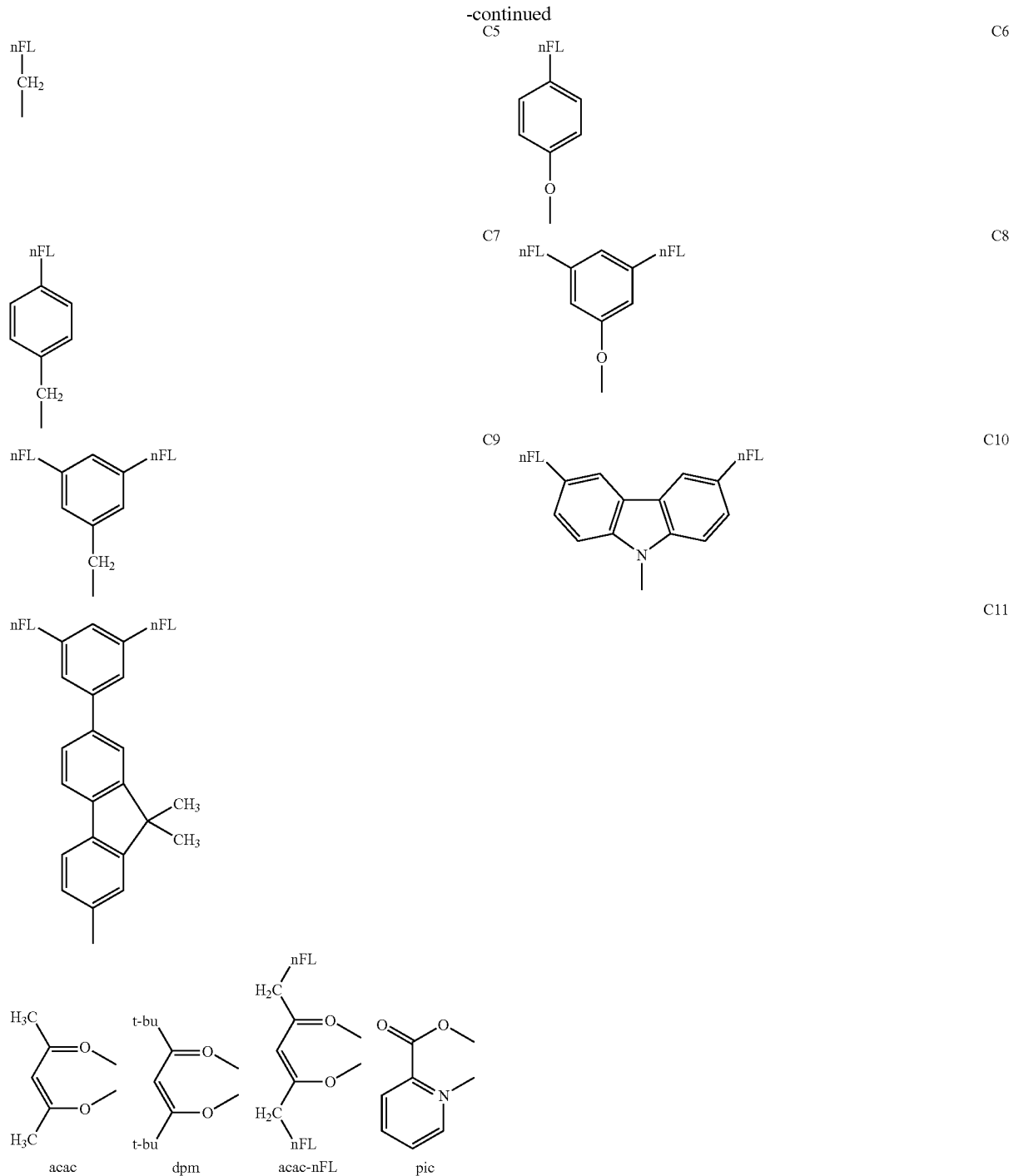

The symbol "nFL" above represents an abbreviated name shown in any one of 1FL1 to 1FL6, 2FL1 to 2FL7, 3FL1 to 3FL6 and 4FL1 to 4FL6. That is, in the case of, for example, any one of the above exemplified compounds, the abbreviated name of a substituent including a fluorenyl group is as described below.

Exemplified Compound 1001: C1-3FL2
Exemplified Compound 1002: C2-3FL2
Exemplified Compound 1003: C8-3FL3
Exemplified Compound 1004: C1-4FL2
Exemplified Compound 1005: C1-4FL1
Exemplified Compound 1006: C1-3FL2
Exemplified Compound 1007: C10-3FL2

Therefore, the structures of those exemplified compounds are as shown in the following Table 1. It should be noted that, when the column of any one of $R_1$ to $R_{10}$ in the following table is blank, the one of $R_1$ to $R_{10}$ represents a hydrogen atom.

Other examples of the light emitting material of the present invention are shown in Tables 2 to 14.

TABLE 1

| Exemplified Compound No. | n | R1 | R2 | R3 | R4 | R5 | R6 | R7 | R8 | R9 | R10 | Addition ligand |
|---|---|---|---|---|---|---|---|---|---|---|---|---|
| 1001 | 3 | | | C1-3FL2 | | | | | | | | |
| 1002 | 3 | | | C2-3FL2 | | | | | | | | |
| 1003 | 3 | | | C8-3FL3 | | | | | | | | |
| 1004 | 3 | | | C1-4FL2 | | | | | | Cyclohexyl | | |
| 1005 | 3 | | | C1-4FL1 | | | | | | $C_6H_{13}-$ | | |
| 1006 | 2 | | $CH_3O-$ | C1-3FL2 | | | | | | | | acac |
| 1007 | 3 | | | C10-3FL2 | | | | | | | | |

TABLE 2

| Exemplified Compound No. | n | R1 | R2 | R3 | R4 | R5 | R6 | R7 | R8 | R9 | R10 | Addition ligand |
|---|---|---|---|---|---|---|---|---|---|---|---|---|
| 2001 | 3 | | C1-1FL1 | | | | | | C1-1FL1 | | | |
| 2002 | 3 | | C1-1FL2 | | | | | | C1-1FL2 | | | |
| 2003 | 3 | | C1-1FL3 | | | | | | C1-1FL3 | | | |
| 2004 | 3 | | C1-1FL4 | | | | | | C1-1FL4 | | | |
| 2005 | 3 | | C1-1FL5 | | | | | | C1-1FL5 | | | |
| 2006 | 3 | | C1-1FL6 | | | | | | C1-1FL6 | | | |
| 2007 | 3 | | C2-1FL1 | | | | | | C2-1FL1 | | | |
| 2008 | 3 | | C3-1FL1 | | | | | | C3-1FL1 | | | |
| 2009 | 3 | | C4-1FL1 | | | | | | C4-1FL1 | | | |
| 2010 | 3 | | C5-1FL1 | | | | | | C5-1FL1 | | | |
| 2011 | 3 | | C6-1FL1 | | | | | | C6-1FL1 | | | |
| 2012 | 3 | | C7-1FL1 | | | | | | C7-1FL1 | | | |
| 2013 | 3 | | C8-1FL1 | | | | | | C8-1FL1 | | | |
| 2014 | 3 | | C9-1FL1 | | | | | | C9-1FL1 | | | |
| 2015 | 3 | | C10-1FL1 | | | | | | C10-1FL1 | | | |
| 2016 | 3 | | C11-1FL1 | | | | | | C11-1FL1 | | | |
| 2017 | 3 | | | C1-1FL1 | | | | | C1-1FL1 | | | |
| 2018 | 3 | | | C1-1FL2 | | | | | C1-1FL2 | | | |
| 2019 | 3 | | | C1-1FL3 | | | | | C1-1FL3 | | | |
| 2020 | 3 | | | C1-1FL4 | | | | | C1-1FL4 | | | |
| 2021 | 3 | | | C1-1FL5 | | | | | C1-1FL5 | | | |
| 2022 | 3 | | | C1-1FL6 | | | | | C1-1FL6 | | | |
| 2023 | 3 | | | C2-1FL1 | | | | | C2-1FL1 | | | |
| 2024 | 3 | | | C3-1FL1 | | | | | C3-1FL1 | | | |
| 2025 | 3 | | | C4-1FL1 | | | | | C4-1FL1 | | | |
| 2026 | 3 | | | C5-1FL1 | | | | | C5-1FL1 | | | |
| 2027 | 3 | | | C6-1FL1 | | | | | C6-1FL1 | | | |
| 2028 | 3 | | | C7-1FL1 | | | | | C7-1FL1 | | | |
| 2029 | 3 | | | C8-1FL1 | | | | | C8-1FL1 | | | |
| 2030 | 3 | | | C9-1FL1 | | | | | C9-1FL1 | | | |
| 2031 | 3 | | | C10-1FL1 | | | | | C10-1FL1 | | | |
| 2032 | 3 | | | C11-1FL1 | | | | | C11-1FL1 | | | |
| 2033 | 3 | | | C1-1FL1 | | | | | | C1-1FL1 | | |
| 2034 | 3 | | | C1-1FL2 | | | | | | C1-1FL2 | | |
| 2035 | 3 | | | C1-1FL3 | | | | | | C1-1FL3 | | |
| 2036 | 3 | | | C1-1FL4 | | | | | | C1-1FL4 | | |
| 2037 | 3 | | | C1-1FL5 | | | | | | C1-1FL5 | | |
| 2038 | 3 | | | C1-1FL6 | | | | | | C1-1FL6 | | |
| 2039 | 3 | | | C2-1FL1 | | | | | | C2-1FL1 | | |
| 2040 | 3 | | | C3-1FL1 | | | | | | C3-1FL1 | | |
| 2041 | 3 | | | C4-1FL1 | | | | | | C4-1FL1 | | |
| 2042 | 3 | | | C5-1FL1 | | | | | | C5-1FL1 | | |
| 2043 | 3 | | | C6-1FL1 | | | | | | C6-1FL1 | | |
| 2044 | 3 | | | C7-1FL1 | | | | | | C7-1FL1 | | |
| 2045 | 3 | | | C8-1FL1 | | | | | | C8-1FL1 | | |
| 2046 | 3 | | | C9-1FL1 | | | | | | C9-1FL1 | | |
| 2047 | 3 | | | C10-1FL1 | | | | | | C10-1FL1 | | |
| 2048 | 3 | | | C11-1FL1 | | | | | | C11-1FL1 | | |
| 2049 | 2 | | | C1-1FL1 | | | | | C1-1FL1 | | | acac |
| 2050 | 2 | | | C1-1FL2 | | | | | C1-1FL2 | | | acac |
| 2051 | 2 | | | C1-1FL3 | | | | | C1-1FL3 | | | acac |
| 2052 | 2 | | | C1-1FL4 | | | | | C1-1FL4 | | | acac |
| 2053 | 2 | | | C1-1FL5 | | | | | C1-1FL5 | | | acac |
| 2054 | 2 | | | C1-1FL6 | | | | | C1-1FL6 | | | acac |
| 2055 | 2 | | | C2-1FL1 | | | | | C2-1FL1 | | | acac |
| 2056 | 2 | | | C3-1FL1 | | | | | C3-1FL1 | | | acac |
| 2057 | 2 | | | C4-1FL1 | | | | | C4-1FL1 | | | acac |
| 2058 | 2 | | | C5-1FL1 | | | | | C5-1FL1 | | | acac |
| 2059 | 2 | | | C6-1FL1 | | | | | C6-1FL1 | | | acac |
| 2060 | 2 | | | C7-1FL1 | | | | | C7-1FL1 | | | acac |

TABLE 2-continued

| Exemplified Compound No. | n | R1 | R2 | R3 | R4 | R5 | R6 | R7 | R8 | R9 | R10 | Addition ligand |
|---|---|---|---|---|---|---|---|---|---|---|---|---|
| 2061 | 2 | | | C8-1FL1 | | | | | C8-1FL1 | | | acac |
| 2062 | 2 | | | C9-1FL1 | | | | | C9-1FL1 | | | acac |
| 2063 | 2 | | | C10-1FL1 | | | | | C10-1FL1 | | | acac |
| 2064 | 2 | | | C11-1FL1 | | | | | C11-1FL1 | | | acac |
| 2065 | 3 | | F | C1-1FL1 | | | | | C1-1FL1 | | | |
| 2066 | 3 | | CH$_3$O | C1-1FL1 | | | | | C1-1FL1 | | | |
| 2067 | 3 | | F | C2-1FL1 | | | | | C2-1FL1 | | | |
| 2068 | 3 | | CH$_3$O | C2-1FL1 | | | | | C2-1FL1 | | | |

TABLE 3

| Exemplified Compound No. | n | R1 | R2 | R3 | R4 | R5 | R6 | R7 | R8 | R9 | R10 | Addition ligand |
|---|---|---|---|---|---|---|---|---|---|---|---|---|
| 3001 | 3 | | C1-2FL1 | | | | | | | | | |
| 3002 | 3 | | C1-2FL2 | | | | | | | | | |
| 3003 | 3 | | C1-2FL3 | | | | | | | | | |
| 3004 | 3 | | C1-2FL4 | | | | | | | | | |
| 3005 | 3 | | C1-2FL5 | | | | | | | | | |
| 3006 | 3 | | C1-2FL6 | | | | | | | | | |
| 3007 | 3 | | C1-2FL7 | | | | | | | | | |
| 3008 | 3 | | C2-2FL1 | | | | | | | | | |
| 3009 | 3 | | C3-2FL1 | | | | | | | | | |
| 3010 | 3 | | C4-2FL1 | | | | | | | | | |
| 3011 | 3 | | C5-2FL1 | | | | | | | | | |
| 3012 | 3 | | C6-2FL1 | | | | | | | | | |
| 3013 | 3 | | C7-2FL1 | | | | | | | | | |
| 3014 | 3 | | C8-2FL1 | | | | | | | | | |
| 3015 | 3 | | C9-2FL1 | | | | | | | | | |
| 3016 | 3 | | C10-2FL1 | | | | | | | | | |
| 3017 | 3 | | C11-2FL1 | | | | | | | | | |
| 3018 | 3 | | | C1-2FL1 | | | | | | | | |
| 3019 | 3 | | | C1-2FL2 | | | | | | | | |
| 3020 | 3 | | | C1-2FL3 | | | | | | | | |
| 3021 | 3 | | | C1-2FL4 | | | | | | | | |
| 3022 | 3 | | | C1-2FL5 | | | | | | | | |
| 3023 | 3 | | | C1-2FL6 | | | | | | | | |
| 3024 | | | | C1-2FL7 | | | | | | | | |
| 3025 | 3 | | | C2-2FL1 | | | | | | | | |
| 3026 | 3 | | | C3-2FL1 | | | | | | | | |
| 3027 | 3 | | | C4-2FL1 | | | | | | | | |
| 3028 | 3 | | | C5-2FL1 | | | | | | | | |
| 3029 | 3 | | | C6-2FL1 | | | | | | | | |
| 3030 | 3 | | | C7-2FL1 | | | | | | | | |
| 3031 | 3 | | | C8-2FL1 | | | | | | | | |
| 3032 | 3 | | | C9-2FL1 | | | | | | | | |
| 3033 | 3 | | | C10-2FL1 | | | | | | | | |
| 3034 | 3 | | | C11-2FL1 | | | | | | | | |
| 3035 | 3 | | | | | | | | C1-2FL1 | | | |
| 3036 | 3 | | | | | | | | C1-2FL2 | | | |
| 3037 | 3 | | | | | | | | C1-2FL3 | | | |

TABLE 4

| Exemplified Compound No. | n | R1 | R2 | R3 | R4 | R5 | R6 | R7 | R8 | R9 | R10 | Addition ligand |
|---|---|---|---|---|---|---|---|---|---|---|---|---|
| 3038 | 3 | | | | | | | | C1-2FL4 | | | |
| 3039 | 3 | | | | | | | | C1-2FL5 | | | |
| 3040 | 3 | | | | | | | | C1-2FL6 | | | |
| 3041 | 3 | | | | | | | | C1-2FL7 | | | |
| 3042 | 3 | | | | | | | | C2-2FL1 | | | |
| 3043 | 3 | | | | | | | | C3-2FL1 | | | |
| 3044 | 3 | | | | | | | | C4-2FL1 | | | |
| 3045 | 3 | | | | | | | | C5-2FL1 | | | |
| 3046 | 3 | | | | | | | | C6-2FL1 | | | |
| 3047 | 3 | | | | | | | | C7-2FL1 | | | |
| 3048 | 3 | | | | | | | | C8-2FL1 | | | |
| 3049 | 3 | | | | | | | | C9-2FL1 | | | |
| 3050 | 3 | | | | | | | | C10-2FL1 | | | |
| 3051 | 3 | | | | | | | | C11-2FL1 | | | |

TABLE 4-continued

| Exemplified Compound No. | n | R1 | R2 | R3 | R4 | R5 | R6 | R7 | R8 | R9 | R10 | Addition ligand |
|---|---|---|---|---|---|---|---|---|---|---|---|---|
| 3052 | 2 | | | C1-2FL1 | | | | | | | | acac |
| 3053 | 2 | | | C1-2FL2 | | | | | | | | acac |
| 3054 | 2 | | | C1-2FL3 | | | | | | | | acac |
| 3055 | 2 | | | C1-2FL4 | | | | | | | | acac |
| 3056 | 2 | | | C1-2FL5 | | | | | | | | acac |
| 3057 | 2 | | | C1-2FL6 | | | | | | | | acac |
| 3058 | 2 | | | C1-2FL7 | | | | | | | | acac |
| 3059 | 2 | | | C2-2FL1 | | | | | | | | acac |
| 3060 | 2 | | | C3-2FL1 | | | | | | | | acac |
| 3061 | 2 | | | C4-2FL1 | | | | | | | | acac |
| 3062 | 2 | | | C5-2FL1 | | | | | | | | acac |
| 3063 | 2 | | | C6-2FL1 | | | | | | | | acac |
| 3064 | 2 | | | C7-2FL1 | | | | | | | | acac |
| 3065 | 2 | | | C8-2FL1 | | | | | | | | acac |
| 3066 | 2 | | | C9-2FL1 | | | | | | | | acac |
| 3067 | 2 | | | C10-2FL1 | | | | | | | | acac |
| 3068 | 2 | | | C11-2FL1 | | | | | | | | acac |
| 3069 | 3 | | F | C2-2FL1 | | | | | | | | |
| 3070 | 3 | | CH$_3$O | C2-2FL1 | | | | | | | | |
| 3071 | 3 | | F | C2-1FL1 | | | | | | | | |
| 3072 | 3 | | CH$_3$O | C2-1FL1 | | | | | | | | |
| 3073 | 3 | | | C2-2FL1 | | | | | | F | | |
| 3074 | 3 | | | C2-2FL1 | | | | | | Cyclohexyl | | |
| 3075 | 3 | | | C2-1FL1 | | | | | | F | | |
| 3076 | 3 | | | C2-1FL1 | | | | | | Cyclohexyl | | |

TABLE 5

| Exemplified Compound No. | n | R1 | R2 | R3 | R4 | R5 | R6 | R7 | R8 | R9 | R10 | Addition ligand |
|---|---|---|---|---|---|---|---|---|---|---|---|---|
| 4001 | 3 | | C1-3FL1 | | | | | | | | | |
| 4002 | 3 | | C1-3FL2 | | | | | | | | | |
| 4003 | 3 | | C1-3FL3 | | | | | | | | | |
| 4004 | 3 | | C1-3FL4 | | | | | | | | | |
| 4005 | 3 | | C1-3FL5 | | | | | | | | | |
| 4006 | 3 | | C1-3FL6 | | | | | | | | | |
| 4007 | 3 | | C2-3FL1 | | | | | | | | | |
| 4008 | 3 | | C2-3FL2 | | | | | | | | | |
| 4009 | 3 | | C2-3FL3 | | | | | | | | | |
| 4010 | 3 | | C2-3FL4 | | | | | | | | | |
| 4011 | 3 | | C2-3FL5 | | | | | | | | | |
| 4012 | 3 | | C2-3FL6 | | | | | | | | | |
| 4013 | 3 | | C3-3FL1 | | | | | | | | | |
| 4014 | 3 | | C3-3FL2 | | | | | | | | | |
| 4015 | 3 | | C3-3FL3 | | | | | | | | | |
| 4016 | 3 | | C3-3FL4 | | | | | | | | | |
| 4017 | 3 | | C3-3FL5 | | | | | | | | | |
| 4018 | 3 | | C3-3FL6 | | | | | | | | | |
| 4019 | 3 | | C3-3FL1 | | | | | | | | | |
| 4020 | 3 | | C3-3FL2 | | | | | | | | | |
| 4021 | 3 | | C3-3FL3 | | | | | | | | | |
| 4022 | 3 | | C3-3FL4 | | | | | | | | | |
| 4023 | 3 | | C3-3FL5 | | | | | | | | | |
| 4024 | 3 | | C3-3FL6 | | | | | | | | | |
| 4025 | 3 | | C8-3FL1 | | | | | | | | | |
| 4026 | 3 | | C8-3FL2 | | | | | | | | | |
| 4027 | 3 | | C8-3FL3 | | | | | | | | | |
| 4028 | 3 | | C8-3FL4 | | | | | | | | | |
| 4029 | 3 | | C8-3FL5 | | | | | | | | | |
| 4030 | 3 | | C8-3FL6 | | | | | | | | | |
| 4031 | 3 | | C10-3FL1 | | | | | | | | | |
| 4032 | 3 | | C10-3FL2 | | | | | | | | | |
| 4033 | 3 | | C10-3FL3 | | | | | | | | | |
| 4034 | 3 | | C10-3FL4 | | | | | | | | | |
| 4035 | 3 | | C10-3FL5 | | | | | | | | | |
| 4036 | 3 | | C10-3FL6 | | | | | | | | | |
| 4037 | 3 | | | C1-3FL1 | | | | | | | | |
| 4038 | 3 | | | C1-3FL2 | | | | | | | | |
| 4039 | 3 | | | C1-3FL3 | | | | | | | | |
| 4040 | 3 | | | C1-3FL4 | | | | | | | | |
| 4041 | 3 | | | C1-3FL5 | | | | | | | | |
| 4042 | 3 | | | C1-3FL6 | | | | | | | | |

TABLE 5-continued

| Exemplified Compound No. | n | R1 | R2 | R3 | R4 | R5 | R6 | R7 | R8 | R9 | R10 | Addition ligand |
|---|---|---|---|---|---|---|---|---|---|---|---|---|
| 4043 | 3 | | | C2-3FL1 | | | | | | | | |
| 4044 | 3 | | | C2-3FL2 | | | | | | | | |
| 4045 | 3 | | | C2-3FL3 | | | | | | | | |
| 4046 | 3 | | | C2-3FL4 | | | | | | | | |
| 4047 | 3 | | | C2-3FL5 | | | | | | | | |
| 4048 | 3 | | | C2-3FL6 | | | | | | | | |
| 4049 | 3 | | | C3-3FL1 | | | | | | | | |
| 4050 | 3 | | | C3-3FL2 | | | | | | | | |
| 4051 | 3 | | | C3-3FL3 | | | | | | | | |
| 4052 | 3 | | | C3-3FL4 | | | | | | | | |
| 4053 | 3 | | | C3-3FL5 | | | | | | | | |
| 4054 | 3 | | | C3-3FL6 | | | | | | | | |
| 4055 | 3 | | | C3-3FL1 | | | | | | | | |
| 4056 | 3 | | | C3-3FL2 | | | | | | | | |
| 4057 | 3 | | | C3-3FL3 | | | | | | | | |
| 4058 | 3 | | | C3-3FL4 | | | | | | | | |
| 4059 | 3 | | | C3-3FL5 | | | | | | | | |
| 4060 | 3 | | | C3-3FL6 | | | | | | | | |

TABLE 6

| Exemplified Compound No. | n | R1 | R2 | R3 | R4 | R5 | R6 | R7 | R8 | R9 | R10 | Addition ligand |
|---|---|---|---|---|---|---|---|---|---|---|---|---|
| 4061 | 3 | | | C8-3FL1 | | | | | | | | |
| 4062 | 3 | | | C8-3FL2 | | | | | | | | |
| 4063 | 3 | | | C8-3FL3 | | | | | | | | |
| 4064 | 3 | | | C8-3FL4 | | | | | | | | |
| 4065 | 3 | | | C8-3FL5 | | | | | | | | |
| 4066 | 3 | | | C8-3FL6 | | | | | | | | |
| 4067 | 3 | | | C10-3FL1 | | | | | | | | |
| 4068 | 3 | | | C10-3FL2 | | | | | | | | |
| 4069 | 3 | | | C10-3FL3 | | | | | | | | |
| 4070 | 3 | | | C10-3FL4 | | | | | | | | |
| 4071 | 3 | | | C10-3FL5 | | | | | | | | |
| 4072 | 3 | | | C10-3FL6 | | | | | | | | |
| 4073 | 3 | | C1-3FL1 | | | | | | | $C_6H_{13}$ | | |
| 4074 | 3 | | C1-3FL1 | | | | | | | $CH_3$ | | |
| 4075 | 3 | | C1-3FL1 | | | | | | | $CH_3O$ | | |
| 4076 | 3 | | C1-3FL1 | | | | | | | F | | |
| 4077 | 3 | | C1-3FL1 | | | | | | | Cyclohexyl | | |
| 4078 | 3 | | C1-3FL1 | F | | | | | | | | |
| 4079 | 3 | | C1-3FL1 | $CH_3$ | | | | | | | | |
| 4080 | 3 | | C1-3FL1 | $OCH_3$ | | | | | | | | |
| 4081 | 3 | | C1-3FL2 | | | | | | | $C_6H_{13}$ | | |
| 4082 | 3 | | C1-3FL2 | | | | | | | $CH_3$ | | |
| 4083 | 3 | | C1-3FL2 | | | | | | | $CH_3O$ | | |
| 4084 | 3 | | C1-3FL2 | | | | | | | F | | |
| 4085 | 3 | | C1-3FL2 | | | | | | | Cyclohexyl | | |
| 4086 | 3 | | C1-3FL2 | F | | | | | | | | |
| 4087 | 3 | | C1-3FL2 | $CH_3$ | | | | | | | | |
| 4088 | 3 | | C1-3FL2 | $OCH_3$ | | | | | | | | |
| 4089 | 3 | | C2-3FL1 | | | | | | | $C_6H_{13}$ | | |
| 4090 | 3 | | C2-3FL1 | | | | | | | $CH_3$ | | |
| 4091 | 3 | | C2-3FL1 | | | | | | | $CH_3O$ | | |
| 4092 | 3 | | C2-3FL1 | | | | | | | F | | |
| 4093 | 3 | | C2-3FL1 | | | | | | | Cyclohexyl | | |
| 4094 | 3 | | C2-3FL1 | F | | | | | | | | |
| 4095 | 3 | | C2-3FL1 | $CH_3$ | | | | | | | | |
| 4096 | 3 | | C2-3FL1 | $OCH_3$ | | | | | | | | |
| 4097 | 3 | | C2-3FL2 | | | | | | | $C_6H_{13}$ | | |
| 4098 | 3 | | C2-3FL2 | | | | | | | $CH_3$ | | |
| 4099 | 3 | | C2-3FL2 | | | | | | | $CH_3O$ | | |
| 4100 | 3 | | C2-3FL2 | | | | | | | F | | |
| 4101 | 3 | | C2-3FL2 | | | | | | | Cyclohexyl | | |
| 4102 | 3 | | C2-3FL2 | F | | | | | | | | |
| 4103 | 3 | | C2-3FL2 | $CH_3$ | | | | | | | | |
| 4104 | 3 | | C2-3FL2 | $OCH_3$ | | | | | | | | |
| 4105 | 3 | | C10-3FL1 | | | | | | | $C_6H_{13}$ | | |
| 4106 | 3 | | C10-3FL1 | | | | | | | $CH_3$ | | |
| 4107 | 3 | | C10-3FL1 | | | | | | | $CH_3O$ | | |
| 4108 | 3 | | C10-3FL1 | | | | | | | F | | |
| 4109 | 3 | | C10-3FL1 | | | | | | | Cyclohexyl | | |

TABLE 6-continued

| Exemplified Compound No. | n | R1 | R2 | R3 | R4 | R5 | R6 | R7 | R8 | R9 | R10 | Addition ligand |
|---|---|---|---|---|---|---|---|---|---|---|---|---|
| 4110 | 3 | | C10-3FL1 | F | | | | | | | | |
| 4111 | 3 | | C10-3FL1 | CH$_3$ | | | | | | | | |
| 4112 | 3 | | C10-3FL1 | OCH$_3$ | | | | | | | | |
| 4113 | 3 | | C10-3FL2 | | | | | | | C$_6$H$_{13}$ | | |
| 4114 | 3 | | C10-3FL2 | | | | | | | CH$_3$ | | |
| 4115 | 3 | | C10-3FL2 | | | | | | | CH$_3$O | | |
| 4116 | 3 | | C10-3FL2 | | | | | | | F | | |
| 4117 | 3 | | C10-3FL2 | | | | | | | Cyclohexyl | | |
| 4118 | 3 | | C10-3FL2 | F | | | | | | | | |
| 4119 | 3 | | C10-3FL2 | CH$_3$ | | | | | | | | |
| 4120 | 3 | | C10-3FL2 | OCH$_3$ | | | | | | | | |

TABLE 7

| Exemplified Compound No. | n | R1 | R2 | R3 | R4 | R5 | R6 | R7 | R8 | R9 | R10 | Addition ligand |
|---|---|---|---|---|---|---|---|---|---|---|---|---|
| 4121 | 3 | | | C1-3FL1 | | | | | | C$_6$H$_{13}$ | | |
| 4122 | 3 | | | C1-3FL1 | | | | | | CH$_3$ | | |
| 4123 | 3 | | | C1-3FL1 | | | | | | CH$_3$O | | |
| 4124 | 3 | | | C1-3FL1 | | | | | | F | | |
| 4125 | 3 | | | C1-3FL1 | | | | | | Cyclohexyl | | |
| 4126 | 3 | | F | C1-3FL1 | | | | | | | | |
| 4127 | 3 | | CH$_3$ | C1-3FL1 | | | | | | | | |
| 4128 | 3 | | OCH$_3$ | C1-3FL1 | | | | | | | | |
| 4129 | 3 | | | C1-3FL2 | | | | | | C$_6$H$_{13}$ | | |
| 4130 | 3 | | | C1-3FL2 | | | | | | CH$_3$ | | |
| 4131 | 3 | | | C1-3FL2 | | | | | | CH$_3$O | | |
| 4132 | 3 | | | C1-3FL2 | | | | | | F | | |
| 4133 | 3 | | | C1-3FL2 | | | | | | Cyclohexyl | | |
| 4134 | 3 | | F | C1-3FL2 | | | | | | | | |
| 4135 | 3 | | CH$_3$ | C1-3FL2 | | | | | | | | |
| 4136 | 3 | | OCH$_3$ | C1-3FL2 | | | | | | | | |
| 4137 | 3 | | | C2-3FL1 | | | | | | C$_6$H$_{13}$ | | |
| 4138 | 3 | | | C2-3FL1 | | | | | | CH$_3$ | | |
| 4139 | 3 | | | C2-3FL1 | | | | | | CH$_3$O | | |
| 4140 | 3 | | | C2-3FL1 | | | | | | F | | |
| 4141 | 3 | | | C2-3FL1 | | | | | | Cyclohexyl | | |
| 4142 | 3 | | F | C2-3FL1 | | | | | | | | |
| 4143 | 3 | | CH$_3$ | C2-3FL1 | | | | | | | | |
| 4144 | 3 | | OCH$_3$ | C2-3FL1 | | | | | | | | |
| 4145 | 3 | | | C2-3FL2 | | | | | | C$_6$H$_{13}$ | | |
| 4146 | 3 | | | C2-3FL2 | | | | | | CH$_3$ | | |
| 4147 | 3 | | | C2-3FL2 | | | | | | CH$_3$O | | |
| 4148 | 3 | | | C2-3FL2 | | | | | | F | | |
| 4149 | 3 | | | C2-3FL2 | | | | | | Cyclohexyl | | |
| 4150 | 3 | | F | C2-3FL2 | | | | | | | | |
| 4151 | 3 | | CH$_3$ | C2-3FL2 | | | | | | | | |
| 4152 | 3 | | OCH$_3$ | C2-3FL2 | | | | | | | | |
| 4153 | 3 | | | C10-3FL1 | | | | | | C$_6$H$_{13}$ | | |
| 4154 | 3 | | | C10-3FL1 | | | | | | CH$_3$ | | |
| 4155 | 3 | | | C10-3FL1 | | | | | | CH$_3$O | | |
| 4156 | 3 | | | C10-3FL1 | | | | | | F | | |
| 4157 | 3 | | | C10-3FL1 | | | | | | Cyclohexyl | | |
| 4158 | 3 | | F | C10-3FL1 | | | | | | | | |
| 4159 | 3 | | CH$_3$ | C10-3FL1 | | | | | | | | |
| 4160 | 3 | | OCH$_3$ | C10-3FL1 | | | | | | | | |
| 4161 | 3 | | | C10-3FL2 | | | | | | C$_6$H$_{13}$ | | |
| 4162 | 3 | | | C10-3FL2 | | | | | | CH$_3$ | | |
| 4163 | 3 | | | C10-3FL2 | | | | | | CH$_3$O | | |
| 4164 | 3 | | | C10-3FL2 | | | | | | F | | |
| 4165 | 3 | | | C10-3FL2 | | | | | | Cyclohexyl | | |
| 4166 | 3 | | F | C10-3FL2 | | | | | | | | |
| 4167 | 3 | | CH$_3$ | C10-3FL2 | | | | | | | | |
| 4168 | 3 | | OCH$_3$ | C10-3FL2 | | | | | | | | |
| 4169 | 2 | | C1-3FL1 | | | | | | | | | acac |
| 4170 | 2 | | C1-3FL2 | | | | | | | | | acac |
| 4171 | 2 | | C1-3FL3 | | | | | | | | | acac |
| 4172 | 2 | | C1-3FL4 | | | | | | | | | acac |
| 4173 | 2 | | C1-3FL5 | | | | | | | | | acac |
| 4174 | 2 | | C1-3FL6 | | | | | | | | | acac |
| 4175 | 2 | | C2-3FL1 | | | | | | | | | acac |
| 4176 | 2 | | C2-3FL2 | | | | | | | | | acac |

TABLE 7-continued

| Exemplified Compound No. | n | R1 | R2 | R3 | R4 | R5 | R6 | R7 | R8 | R9 | R10 | Addition ligand |
|---|---|---|---|---|---|---|---|---|---|---|---|---|
| 4177 | 2 |  | C2-3FL3 |  |  |  |  |  |  |  |  | acac |
| 4178 | 2 |  | C2-3FL4 |  |  |  |  |  |  |  |  | acac |
| 4179 | 2 |  | C2-3FL5 |  |  |  |  |  |  |  |  | acac |
| 4180 | 2 |  | C2-3FL6 |  |  |  |  |  |  |  |  | acac |

TABLE 8

| Exemplified Compound No. | n | R1 | R2 | R3 | R4 | R5 | R6 | R7 | R8 | R9 | R10 | Addition ligand |
|---|---|---|---|---|---|---|---|---|---|---|---|---|
| 4181 | 2 |  | C3-3FL1 |  |  |  |  |  |  |  |  | acac |
| 4182 | 2 |  | C3-3FL2 |  |  |  |  |  |  |  |  | acac |
| 4183 | 2 |  | C3-3FL3 |  |  |  |  |  |  |  |  | acac |
| 4184 | 2 |  | C3-3FL4 |  |  |  |  |  |  |  |  | acac |
| 4185 | 2 |  | C3-3FL5 |  |  |  |  |  |  |  |  | acac |
| 4186 | 2 |  | C3-3FL6 |  |  |  |  |  |  |  |  | acac |
| 4187 | 2 |  | C3-3FL1 |  |  |  |  |  |  |  |  | pic |
| 4188 | 2 |  | C3-3FL2 |  |  |  |  |  |  |  |  | pic |
| 4189 | 2 |  | C3-3FL3 |  |  |  |  |  |  |  |  | pic |
| 4190 | 2 |  | C3-3FL4 |  |  |  |  |  |  |  |  | pic |
| 4191 | 2 |  | C3-3FL5 |  |  |  |  |  |  |  |  | pic |
| 4192 | 2 |  | C3-3FL6 |  |  |  |  |  |  |  |  | pic |
| 4193 | 2 |  | C8-3FL1 |  |  |  |  |  |  |  |  | pic |
| 4194 | 2 |  | C8-3FL2 |  |  |  |  |  |  |  |  | pic |
| 4195 | 2 |  | C8-3FL3 |  |  |  |  |  |  |  |  | pic |
| 4196 | 2 |  | C8-3FL4 |  |  |  |  |  |  |  |  | pic |
| 4197 | 2 |  | C8-3FL5 |  |  |  |  |  |  |  |  | pic |
| 4198 | 2 |  | C8-3FL6 |  |  |  |  |  |  |  |  | pic |
| 4199 | 2 |  | C10-3FL1 |  |  |  |  |  |  |  |  | pic |
| 4200 | 2 |  | C10-3FL2 |  |  |  |  |  |  |  |  | pic |
| 4201 | 2 |  | C10-3FL3 |  |  |  |  |  |  |  |  | pic |
| 4202 | 2 |  | C10-3FL4 |  |  |  |  |  |  |  |  | pic |
| 4203 | 2 |  | C10-3FL5 |  |  |  |  |  |  |  |  | pic |
| 4204 | 2 |  | C10-3FL6 |  |  |  |  |  |  |  |  | pic |
| 4205 | 2 |  | C1-3FL1 |  |  |  |  |  |  |  |  | dpm |
| 4206 | 2 |  | C1-3FL1 |  |  |  |  |  |  |  |  | acac-3FL1 |
| 4207 | 2 |  | C1-3FL1 |  |  |  |  |  |  |  |  | acac-4FL1 |
| 4208 | 2 |  | C1-3FL1 |  |  |  |  |  |  |  |  | dpm |
| 4209 | 2 |  | C1-3FL1 |  |  |  |  |  |  |  |  | dpm |
| 4210 | 2 |  |  | C1-3FL1 |  |  |  |  |  | $C_6H_{13}$ |  | acac |
| 4211 | 2 |  |  | C1-3FL1 |  |  |  |  |  | $CH_3$ |  | acac |
| 4212 | 2 |  |  | C1-3FL1 |  |  |  |  |  | $CH_3O$ |  | acac |
| 4213 | 2 |  |  | C1-3FL1 |  |  |  |  |  | F |  | acac |
| 4214 | 2 |  |  | C1-3FL1 |  |  |  |  |  | Cyclohexyl |  | acac |
| 4215 | 2 |  | F | C1-3FL1 |  |  |  |  |  |  |  | acac |
| 4216 | 2 |  | $CH_3$ | C1-3FL1 |  |  |  |  |  |  |  | acac |
| 4217 | 2 |  | $OCH_3$ | C1-3FL1 |  |  |  |  |  |  |  | acac |
| 4218 | 2 |  |  | C1-3FL2 |  |  |  |  |  | $C_6H_{13}$ |  | acac |
| 4219 | 2 |  |  | C1-3FL2 |  |  |  |  |  | $CH_3$ |  | acac |
| 4220 | 2 |  |  | C1-3FL2 |  |  |  |  |  | $CH_3O$ |  | acac |
| 4221 | 2 |  |  | C1-3FL2 |  |  |  |  |  | F |  | acac |
| 4222 | 2 |  |  | C1-3FL2 |  |  |  |  |  | Cyclohexyl |  | acac |
| 4223 | 2 |  | F | C1-3FL2 |  |  |  |  |  |  |  | acac |
| 4224 | 2 |  | $CH_3$ | C1-3FL2 |  |  |  |  |  |  |  | acac |
| 4225 | 2 |  | $OCH_3$ | C1-3FL2 |  |  |  |  |  |  |  | acac |
| 4226 | 3 |  |  |  |  |  |  |  |  | C1-3FL1 |  |  |
| 4227 | 3 |  |  |  |  |  |  |  |  | C1-3FL2 |  |  |
| 4228 | 3 |  |  |  |  |  |  |  |  | C1-3FL3 |  |  |
| 4229 | 3 |  |  |  |  |  |  |  |  | C1-3FL4 |  |  |
| 4230 | 3 |  |  |  |  |  |  |  |  | C1-3FL5 |  |  |
| 4231 | 3 |  |  |  |  |  |  |  |  | C1-3FL6 |  |  |
| 4232 | 3 |  |  |  |  |  |  |  |  | C2-3FL1 |  |  |
| 4233 | 3 |  |  |  |  |  |  |  |  | C2-3FL2 |  |  |
| 4234 | 3 |  |  |  |  |  |  |  |  | C2-3FL3 |  |  |
| 4235 | 3 |  |  |  |  |  |  |  |  | C2-3FL4 |  |  |
| 4236 | 3 |  |  |  |  |  |  |  |  | C2-3FL5 |  |  |
| 4237 | 3 |  |  |  |  |  |  |  |  | C2-3FL6 |  |  |

TABLE 9

| Exemplified Compound No. | n | R1 | R2 | R3 | R4 | R5 | R6 | R7 | R8 | R9 | R10 | Addition ligand |
|---|---|---|---|---|---|---|---|---|---|---|---|---|
| 5001 | 3 | | C1-4FL1 | | | | | | | | | |
| 5002 | 3 | | C1-4FL2 | | | | | | | | | |
| 5003 | 3 | | C1-4FL3 | | | | | | | | | |
| 5004 | 3 | | C1-4FL4 | | | | | | | | | |
| 5005 | 3 | | C1-4FL5 | | | | | | | | | |
| 5006 | 3 | | C1-4FL6 | | | | | | | | | |
| 5007 | 3 | | C2-4FL1 | | | | | | | | | |
| 5008 | 3 | | C2-4FL2 | | | | | | | | | |
| 5009 | 3 | | C2-4FL3 | | | | | | | | | |
| 5010 | 3 | | C2-4FL4 | | | | | | | | | |
| 5011 | 3 | | C2-4FL5 | | | | | | | | | |
| 5012 | 3 | | C2-4FL6 | | | | | | | | | |
| 5013 | 3 | | C3-4FL1 | | | | | | | | | |
| 5014 | 3 | | C3-4FL2 | | | | | | | | | |
| 5015 | 3 | | C3-4FL3 | | | | | | | | | |
| 5016 | 3 | | C3-4FL4 | | | | | | | | | |
| 5017 | 3 | | C3-4FL5 | | | | | | | | | |
| 5018 | 3 | | C3-4FL6 | | | | | | | | | |
| 5019 | 3 | | C3-4FL1 | | | | | | | | | |
| 5020 | 3 | | C3-4FL2 | | | | | | | | | |
| 5021 | 3 | | C3-4FL3 | | | | | | | | | |
| 5022 | 3 | | C3-4FL4 | | | | | | | | | |
| 5023 | 3 | | C3-4FL5 | | | | | | | | | |
| 5024 | 3 | | C3-4FL6 | | | | | | | | | |
| 5025 | 3 | | C8-4FL1 | | | | | | | | | |
| 5026 | 3 | | C8-4FL2 | | | | | | | | | |
| 5027 | 3 | | C8-4FL3 | | | | | | | | | |
| 5028 | 3 | | C8-4FL4 | | | | | | | | | |
| 5029 | 3 | | C8-4FL5 | | | | | | | | | |
| 5030 | 3 | | C8-4FL6 | | | | | | | | | |
| 5031 | 3 | | C10-4FL1 | | | | | | | | | |
| 5032 | 3 | | C10-4FL2 | | | | | | | | | |
| 5033 | 3 | | C10-4FL3 | | | | | | | | | |
| 5034 | 3 | | C10-4FL4 | | | | | | | | | |
| 5035 | 3 | | C10-4FL5 | | | | | | | | | |
| 5036 | 3 | | C10-4FL6 | | | | | | | | | |
| 5037 | 3 | | | C1-4FL1 | | | | | | | | |
| 5038 | 3 | | | C1-4FL2 | | | | | | | | |
| 5039 | 3 | | | C1-4FL3 | | | | | | | | |
| 5040 | 3 | | | C1-4FL4 | | | | | | | | |
| 5041 | 3 | | | C1-4FL5 | | | | | | | | |
| 5042 | 3 | | | C1-4FL6 | | | | | | | | |
| 5043 | 3 | | | C2-4FL1 | | | | | | | | |
| 5044 | 3 | | | C2-4FL2 | | | | | | | | |
| 5045 | 3 | | | C2-4FL3 | | | | | | | | |
| 5046 | 3 | | | C2-4FL4 | | | | | | | | |
| 5047 | 3 | | | C2-4FL5 | | | | | | | | |
| 5048 | 3 | | | C2-4FL6 | | | | | | | | |
| 5049 | 3 | | | C3-4FL1 | | | | | | | | |
| 5050 | 3 | | | C3-4FL2 | | | | | | | | |
| 5051 | 3 | | | C3-4FL3 | | | | | | | | |
| 5052 | 3 | | | C3-4FL4 | | | | | | | | |
| 5053 | 3 | | | C3-4FL5 | | | | | | | | |
| 5054 | 3 | | | C3-4FL6 | | | | | | | | |
| 5055 | 3 | | | C3-4FL1 | | | | | | | | |
| 5056 | 3 | | | C3-4FL2 | | | | | | | | |
| 5057 | 3 | | | C3-4FL3 | | | | | | | | |
| 5058 | 3 | | | C3-4FL4 | | | | | | | | |
| 5059 | 3 | | | C3-4FL5 | | | | | | | | |
| 5060 | 3 | | | C3-4FL6 | | | | | | | | |

TABLE 10

| Exemplified Compound No. | n | R1 | R2 | R3 | R4 | R5 | R6 | R7 | R8 | R9 | R10 | Addition ligand |
|---|---|---|---|---|---|---|---|---|---|---|---|---|
| 5061 | 3 | | | C8-4FL1 | | | | | | | | |
| 5062 | 3 | | | C8-4FL2 | | | | | | | | |
| 5063 | 3 | | | C8-4FL3 | | | | | | | | |
| 5064 | 3 | | | C8-4FL4 | | | | | | | | |
| 5065 | 3 | | | C8-4FL5 | | | | | | | | |
| 5066 | 3 | | | C8-4FL6 | | | | | | | | |
| 5067 | 3 | | | C10-4FL1 | | | | | | | | |

TABLE 10-continued

| Exemplified Compound No. | n | R1 | R2 | R3 | R4 | R5 | R6 | R7 | R8 | R9 | R10 | Addition ligand |
|---|---|---|---|---|---|---|---|---|---|---|---|---|
| 5068 | 3 | | | C10-4FL2 | | | | | | | | |
| 5069 | 3 | | | C10-4FL3 | | | | | | | | |
| 5070 | 3 | | | C10-4FL4 | | | | | | | | |
| 5071 | 3 | | | C10-4FL5 | | | | | | | | |
| 5072 | 3 | | | C10-4FL6 | | | | | | | | |
| 5073 | 3 | | C1-4FL1 | | | | | | | $C_6H_{13}$ | | |
| 5074 | 3 | | C1-4FL1 | | | | | | | $CH_3$ | | |
| 5075 | 3 | | C1-4FL1 | | | | | | | $CH_3O$ | | |
| 5076 | 3 | | C1-4FL1 | | | | | | | F | | |
| 5077 | 3 | | C1-4FL1 | | | | | | | Cyclohexyl | | |
| 5078 | 3 | | C1-4FL1 | F | | | | | | | | |
| 5079 | 3 | | C1-4FL1 | $CH_3$ | | | | | | | | |
| 5080 | 3 | | C1-4FL1 | $OCH_3$ | | | | | | | | |
| 5081 | 3 | | C1-4FL2 | | | | | | | $C_6H_{13}$ | | |
| 5082 | 3 | | C1-4FL2 | | | | | | | $CH_3$ | | |
| 5083 | 3 | | C1-4FL2 | | | | | | | $CH_3O$ | | |
| 5084 | 3 | | C1-4FL2 | | | | | | | F | | |
| 5085 | 3 | | C1-4FL2 | | | | | | | Cyclohexyl | | |
| 5086 | 3 | | C1-4FL2 | F | | | | | | | | |
| 5087 | 3 | | C1-4FL2 | $CH_3$ | | | | | | | | |
| 5088 | 3 | | C1-4FL2 | $OCH_3$ | | | | | | | | |
| 5089 | 3 | | C2-4FL1 | | | | | | | $C_6H_{13}$ | | |
| 5090 | 3 | | C2-4FL1 | | | | | | | $CH_3$ | | |
| 5091 | 3 | | C2-4FL1 | | | | | | | $CH_3O$ | | |
| 5092 | 3 | | C2-4FL1 | | | | | | | F | | |
| 5093 | 3 | | C2-4FL1 | | | | | | | Cyclohexyl | | |
| 5094 | 3 | | C2-4FL1 | F | | | | | | | | |
| 5095 | 3 | | C2-4FL1 | $CH_3$ | | | | | | | | |
| 5096 | 3 | | C2-4FL1 | $OCH_3$ | | | | | | | | |
| 5097 | 3 | | C2-4FL2 | | | | | | | $C_6H_{13}$ | | |
| 5098 | 3 | | C2-4FL2 | | | | | | | $CH_3$ | | |
| 5099 | 3 | | C2-4FL2 | | | | | | | $CH_3O$ | | |
| 5100 | 3 | | C2-4FL2 | | | | | | | F | | |
| 5101 | 3 | | C2-4FL2 | | | | | | | Cyclohexyl | | |
| 5102 | 3 | | C2-4FL2 | F | | | | | | | | |
| 5103 | 3 | | C2-4FL2 | $CH_3$ | | | | | | | | |
| 5104 | 3 | | C2-4FL2 | $OCH_3$ | | | | | | | | |
| 5105 | 3 | | C10-4FL1 | | | | | | | $C_6H_{13}$ | | |
| 5106 | 3 | | C10-4FL1 | | | | | | | $CH_3$ | | |
| 5107 | 3 | | C10-4FL1 | | | | | | | $CH_3O$ | | |
| 5108 | 3 | | C10-4FL1 | | | | | | | F | | |
| 5109 | 3 | | C10-4FL1 | | | | | | | Cyclohexyl | | |
| 5110 | 3 | | C10-4FL1 | F | | | | | | | | |
| 5111 | 3 | | C10-4FL1 | $CH_3$ | | | | | | | | |
| 5112 | 3 | | C10-4FL1 | $OCH_3$ | | | | | | | | |
| 5113 | 3 | | C10-4FL2 | | | | | | | $C_6H_{13}$ | | |
| 5114 | 3 | | C10-4FL2 | | | | | | | $CH_3$ | | |
| 5115 | 3 | | C10-4FL2 | | | | | | | $CH_3O$ | | |
| 5116 | 3 | | C10-4FL2 | | | | | | | F | | |
| 5117 | 3 | | C10-4FL2 | | | | | | | Cyclohexyl | | |
| 5118 | 3 | | C10-4FL2 | F | | | | | | | | |
| 5119 | 3 | | C10-4FL2 | $CH_3$ | | | | | | | | |
| 5120 | 3 | | C10-4FL2 | $OCH_3$ | | | | | | | | |

TABLE 11

| Exemplified Compound No. | n | R1 | R2 | R3 | R4 | R5 | R6 | R7 | R8 | R9 | R10 | Addition ligand |
|---|---|---|---|---|---|---|---|---|---|---|---|---|
| 5121 | 3 | | | C1-4FL1 | | | | | | $C_6H_{13}$ | | |
| 5122 | 3 | | | C1-4FL1 | | | | | | $CH_3$ | | |
| 5123 | 3 | | | C1-4FL1 | | | | | | $CH_3O$ | | |
| 5124 | 3 | | | C1-4FL1 | | | | | | F | | |
| 5125 | 3 | | | C1-4FL1 | | | | | | Cyclohexyl | | |
| 5126 | 3 | | F | C1-4FL1 | | | | | | | | |
| 5127 | 3 | | $CH_3$ | C1-4FL1 | | | | | | | | |
| 5128 | 3 | | $OCH_3$ | C1-4FL1 | | | | | | | | |
| 5129 | 3 | | | C1-4FL2 | | | | | | $C_6H_{13}$ | | |
| 5130 | 3 | | | C1-4FL2 | | | | | | $CH_3$ | | |
| 5131 | 3 | | | C1-4FL2 | | | | | | $CH_3O$ | | |
| 5132 | 3 | | | C1-4FL2 | | | | | | F | | |
| 5133 | 3 | | | C1-4FL2 | | | | | | Cyclohexyl | | |
| 5134 | 3 | | F | C1-4FL2 | | | | | | | | |

TABLE 11-continued

| Exemplified Compound No. | n | R1 | R2 | R3 | R4 | R5 | R6 | R7 | R8 | R9 | R10 | Addition ligand |
|---|---|---|---|---|---|---|---|---|---|---|---|---|
| 5135 | 3 | | CH$_3$ | C1-4FL2 | | | | | | | | |
| 5136 | 3 | | OCH$_3$ | C1-4FL2 | | | | | | | | |
| 5137 | 3 | | | C2-4FL1 | | | | | | C$_6$H$_{13}$ | | |
| 5138 | 3 | | | C2-4FL1 | | | | | | CH$_3$ | | |
| 5139 | 3 | | | C2-4FL1 | | | | | | CH$_3$O | | |
| 5140 | 3 | | | C2-4FL1 | | | | | | F | | |
| 5141 | 3 | | | C2-4FL1 | | | | | | Cyclohexyl | | |
| 5142 | 3 | | F | C2-4FL1 | | | | | | | | |
| 5143 | 3 | | CH$_3$ | C2-4FL1 | | | | | | | | |
| 5144 | 3 | | OCH$_3$ | C2-4FL1 | | | | | | | | |
| 5145 | 3 | | | C2-4FL2 | | | | | | C$_6$H$_{13}$ | | |
| 5146 | 3 | | | C2-4FL2 | | | | | | CH$_3$ | | |
| 5147 | 3 | | | C2-4FL2 | | | | | | CH$_3$O | | |
| 5148 | 3 | | | C2-4FL2 | | | | | | F | | |
| 5149 | 3 | | | C2-4FL2 | | | | | | Cyclohexyl | | |
| 5150 | 3 | | F | C2-4FL2 | | | | | | | | |
| 5151 | 3 | | CH$_3$ | C2-4FL2 | | | | | | | | |
| 5152 | 3 | | OCH$_3$ | C2-4FL2 | | | | | | | | |
| 5153 | 3 | | | C10-4FL1 | | | | | | C$_6$H$_{13}$ | | |
| 5154 | 3 | | | C10-4FL1 | | | | | | CH$_3$ | | |
| 5155 | 3 | | | C10-4FL1 | | | | | | CH$_3$O | | |
| 5156 | 3 | | | C10-4FL1 | | | | | | F | | |
| 5157 | 3 | | | C10-4FL1 | | | | | | Cyclohexyl | | |
| 5158 | 3 | | F | C10-4FL1 | | | | | | | | |
| 5159 | 3 | | CH$_3$ | C10-4FL1 | | | | | | | | |
| 5160 | 3 | | OCH$_3$ | C10-4FL1 | | | | | | | | |
| 5161 | 3 | | | C10-4FL2 | | | | | | C$_6$H$_{13}$ | | |
| 5162 | 3 | | | C10-4FL2 | | | | | | CH$_3$ | | |
| 5163 | 3 | | | C10-4FL2 | | | | | | CH$_3$O | | |
| 5164 | 3 | | | C10-4FL2 | | | | | | F | | |
| 5165 | 3 | | | C10-4FL2 | | | | | | Cyclohexyl | | |
| 5166 | 3 | | F | C10-4FL2 | | | | | | | | |
| 5167 | 3 | | CH$_3$ | C10-4FL2 | | | | | | | | |
| 5168 | 3 | | OCH$_3$ | C10-4FL2 | | | | | | | | |
| 5169 | 2 | | | C1-4FL1 | | | | | | | | acac |
| 5170 | 2 | | | C1-4FL2 | | | | | | | | acac |
| 5171 | 2 | | | C1-4FL3 | | | | | | | | acac |
| 5172 | 2 | | | C1-4FL4 | | | | | | | | acac |
| 5173 | 2 | | | C1-4FL5 | | | | | | | | acac |
| 5174 | 2 | | | C1-4FL6 | | | | | | | | acac |
| 5175 | 2 | | | C2-4FL1 | | | | | | | | acac |
| 5176 | 2 | | | C2-4FL2 | | | | | | | | acac |
| 5177 | 2 | | | C2-4FL3 | | | | | | | | acac |
| 5178 | 2 | | | C2-4FL4 | | | | | | | | acac |
| 5179 | 2 | | | C2-4FL5 | | | | | | | | acac |
| 5180 | 2 | | | C2-4FL6 | | | | | | | | acac |

TABLE 12

| Exemplified Compound No. | n | R1 | R2 | R3 | R4 | R5 | R6 | R7 | R8 | R9 | R10 | Addition ligand |
|---|---|---|---|---|---|---|---|---|---|---|---|---|
| 5181 | 2 | | | C3-4FL1 | | | | | | | | acac |
| 5182 | 2 | | | C3-4FL2 | | | | | | | | acac |
| 5183 | 2 | | | C3-4FL3 | | | | | | | | acac |
| 5184 | 2 | | | C3-4FL4 | | | | | | | | acac |
| 5185 | 2 | | | C3-4FL5 | | | | | | | | acac |
| 5186 | 2 | | | C3-4FL6 | | | | | | | | acac |
| 5187 | 2 | | | C3-4FL1 | | | | | | | | pic |
| 5188 | 2 | | | C3-4FL2 | | | | | | | | pic |
| 5189 | 2 | | | C3-4FL3 | | | | | | | | pic |
| 5190 | 2 | | | C3-4FL4 | | | | | | | | pic |
| 5191 | 2 | | | C3-4FL5 | | | | | | | | pic |
| 5192 | 2 | | | C3-4FL6 | | | | | | | | pic |
| 5193 | 2 | | | C8-4FL1 | | | | | | | | pic |
| 5194 | 2 | | | C8-4FL2 | | | | | | | | pic |
| 5195 | 2 | | | C8-4FL3 | | | | | | | | pic |
| 5196 | 2 | | | C8-4FL4 | | | | | | | | pic |
| 5197 | 2 | | | C8-4FL5 | | | | | | | | pic |
| 5198 | 2 | | | C8-4FL6 | | | | | | | | pic |
| 5199 | 2 | | | C10-4FL1 | | | | | | | | pic |
| 5200 | 2 | | | C10-4FL2 | | | | | | | | pic |
| 5201 | 2 | | | C10-4FL3 | | | | | | | | pic |

TABLE 12-continued

| Exemplified Compound No. | n | R1 | R2 | R3 | R4 | R5 | R6 | R7 | R8 | R9 | R10 | Addition ligand |
|---|---|---|---|---|---|---|---|---|---|---|---|---|
| 5202 | 2 | | C10-4FL4 | | | | | | | | | pic |
| 5203 | 2 | | C10-4FL5 | | | | | | | | | pic |
| 5204 | 2 | | C10-4FL6 | | | | | | | | | pic |
| 5205 | 2 | | C1-4FL1 | | | | | | | | | dpm |
| 5206 | 2 | | C1-4FL1 | | | | | | | | | acac-3FL1 |
| 5207 | 2 | | C1-4FL1 | | | | | | | | | acac-4FL1 |
| 5208 | 2 | | C1-4FL1 | | | | | | | | | dpm |
| 5209 | 2 | | C1-4FL1 | | | | | | | | | dpm |
| 5210 | 2 | | | C1-4FL1 | | | | | | $C_6H_{13}$ | | acac |
| 5211 | 2 | | | C1-4FL1 | | | | | | $CH_3$ | | acac |
| 5212 | 2 | | | C1-4FL1 | | | | | | $CH_3O$ | | acac |
| 5213 | 2 | | | C1-4FL1 | | | | | | F | | acac |
| 5214 | 2 | | | C1-4FL1 | | | | | | Cyclohexyl | | acac |
| 5215 | 2 | | F | C1-4FL1 | | | | | | | | acac |
| 5216 | 2 | | $CH_3$ | C1-4FL1 | | | | | | | | acac |
| 5217 | 2 | | $OCH_3$ | C1-4FL1 | | | | | | | | acac |
| 5218 | 2 | | | C1-4FL2 | | | | | | $C_6H_{13}$ | | acac |
| 5219 | 2 | | | C1-4FL2 | | | | | | $CH_3$ | | acac |
| 5220 | 2 | | | C1-4FL2 | | | | | | $CH_3O$ | | acac |
| 5221 | 2 | | | C1-4FL2 | | | | | | F | | acac |
| 5222 | 2 | | | C1-4FL2 | | | | | | Cyclohexyl | | acac |
| 5223 | 2 | | F | C1-4FL2 | | | | | | | | acac |
| 5224 | 2 | | $CH_3$ | C1-4FL2 | | | | | | | | acac |
| 5225 | 2 | | $OCH_3$ | C1-4FL2 | | | | | | | | acac |
| 5226 | 2 | | | | | | | | | C1-4FL1 | | |
| 5227 | 3 | | | | | | | | | C1-4FL2 | | |
| 5228 | 3 | | | | | | | | | C1-4FL3 | | |
| 5229 | 3 | | | | | | | | | C1-4FL4 | | |
| 5230 | 3 | | | | | | | | | C1-4FL5 | | |
| 5231 | 3 | | | | | | | | | C1-4FL6 | | |
| 5232 | 3 | | | | | | | | | C2-4FL1 | | |
| 5233 | 3 | | | | | | | | | C2-4FL2 | | |
| 5234 | 3 | | | | | | | | | C2-4FL3 | | |
| 5235 | 3 | | | | | | | | | C2-4FL4 | | |
| 5236 | 3 | | | | | | | | | C2-4FL5 | | |
| 5237 | 3 | | | | | | | | | C2-4FL6 | | |

TABLE 13

| Exemplified Compound No. | n | R1 | R2 | R3 | R4 | R5 | R6 | R7 | R8 | R9 | R10 | Addition ligand |
|---|---|---|---|---|---|---|---|---|---|---|---|---|
| 6001 | 3 | | C1-5FL1 | | | | | | | | | |
| 6002 | 3 | | C1-5FL2 | | | | | | | | | |
| 6003 | 3 | | C1-5FL3 | | | | | | | | | |
| 6004 | 3 | | C1-5FL4 | | | | | | | | | |
| 6005 | 3 | | C1-5FL5 | | | | | | | | | |
| 6006 | 3 | | C1-5FL6 | | | | | | | | | |
| 6007 | 3 | | C2-5FL1 | | | | | | | | | |
| 6008 | 3 | | C3-5FL1 | | | | | | | | | |
| 6009 | 3 | | C4-5FL1 | | | | | | | | | |
| 6010 | 3 | | C5-5FL1 | | | | | | | | | |
| 6011 | 3 | | C6-5FL1 | | | | | | | | | |
| 6012 | 3 | | C7-5FL1 | | | | | | | | | |
| 6013 | 3 | | C8-5FL1 | | | | | | | | | |
| 6014 | 3 | | C9-5FL1 | | | | | | | | | |
| 6015 | 3 | | C10-5FL1 | | | | | | | | | |
| 6016 | 3 | | C11-5FL1 | | | | | | | | | |
| 6017 | 3 | | | C1-5FL1 | | | | | | | | |
| 6018 | 3 | | | C1-5FL2 | | | | | | | | |
| 6019 | 3 | | | C1-5FL3 | | | | | | | | |
| 6020 | 3 | | | C1-5FL4 | | | | | | | | |
| 6021 | 3 | | | C1-5FL5 | | | | | | | | |
| 6022 | 3 | | | C1-5FL6 | | | | | | | | |
| 6023 | 3 | | | C2-5FL1 | | | | | | | | |
| 6024 | 3 | | | C3-5FL1 | | | | | | | | |
| 6025 | 3 | | | C4-5FL1 | | | | | | | | |
| 6026 | 3 | | | C5-5FL1 | | | | | | | | |
| 6027 | 3 | | | C6-5FL1 | | | | | | | | |
| 6028 | 3 | | | C7-5FL1 | | | | | | | | |
| 6029 | 3 | | | C8-5FL1 | | | | | | | | |
| 6030 | 3 | | | C9-5FL1 | | | | | | | | |
| 6031 | 3 | | | C10-5FL1 | | | | | | | | |

TABLE 13-continued

| Exemplified Compound No. | n | R1 | R2 | R3 | R4 | R5 | R6 | R7 | R8 | R9 | R10 | Addition ligand |
|---|---|---|---|---|---|---|---|---|---|---|---|---|
| 6032 | 3 | | | C11-5FL1 | | | | | | | | |
| 6033 | 3 | | | | | | | | C1-5FL1 | | | |
| 6034 | 3 | | | | | | | | C1-5FL2 | | | |
| 6035 | 3 | | | | | | | | C1-5FL3 | | | |
| 6036 | 3 | | | | | | | | C1-5FL4 | | | |
| 6037 | 3 | | | | | | | | C1-5FL5 | | | |
| 6038 | 3 | | | | | | | | C1-5FL6 | | | |
| 6039 | 3 | | | | | | | | C2-5FL1 | | | |
| 6040 | 3 | | | | | | | | C3-5FL1 | | | |
| 6041 | 3 | | | | | | | | C4-5FL1 | | | |
| 6042 | 3 | | | | | | | | C5-5FL1 | | | |
| 6043 | 3 | | | | | | | | C6-5FL1 | | | |
| 6044 | 3 | | | | | | | | C7-5FL1 | | | |
| 6045 | 3 | | | | | | | | C8-5FL1 | | | |
| 6046 | 3 | | | | | | | | C9-5FL1 | | | |
| 6047 | 3 | | | | | | | | C10-5FL1 | | | |
| 6048 | 3 | | | | | | | | C11-5FL1 | | | |
| 6049 | 2 | | | C1-5FL1 | | | | | | | | acac |
| 6050 | 2 | | | C1-5FL2 | | | | | | | | acac |
| 6051 | 2 | | | C1-5FL3 | | | | | | | | acac |
| 6052 | 2 | | | C1-5FL4 | | | | | | | | acac |
| 6053 | 2 | | | C1-5FL5 | | | | | | | | acac |
| 6054 | 2 | | | C1-5FL6 | | | | | | | | acac |
| 6055 | 2 | | | C2-5FL1 | | | | | | | | acac |
| 6056 | 2 | | | C3-5FL1 | | | | | | | | acac |
| 6057 | 2 | | | C4-5FL1 | | | | | | | | acac |
| 6058 | 2 | | | C5-5FL1 | | | | | | | | acac |
| 6059 | 2 | | | C6-5FL1 | | | | | | | | acac |
| 6060 | 2 | | | C7-5FL1 | | | | | | | | acac |
| 6061 | 2 | | | C8-5FL1 | | | | | | | | acac |
| 6062 | 2 | | | C9-5FL1 | | | | | | | | acac |
| 6063 | 2 | | | C10-5FL1 | | | | | | | | acac |
| 6064 | 2 | | | C11-5FL1 | | | | | | | | acac |
| 6065 | 3 | | F | C1-5FL1 | | | | | | | | |
| 6066 | 3 | | CH$_3$O | C1-5FL1 | | | | | | | | |
| 6067 | 3 | | F | C2-5FL1 | | | | | | | | |
| 6068 | 3 | | CH3O | C2-5FL1 | | | | | | | | |

TABLE 14

| Exemplified Compound No. | n | R1 | R2 | R3 | R4 | R5 | R6 | R7 | R8 | R9 | R10 | Addition ligand |
|---|---|---|---|---|---|---|---|---|---|---|---|---|
| 7001 | 3 | | C1-6FL1 | | | | | | | | | |
| 7002 | 3 | | C1-6FL2 | | | | | | | | | |
| 7003 | 3 | | C1-6FL3 | | | | | | | | | |
| 7004 | 3 | | C1-6FL4 | | | | | | | | | |
| 7005 | 3 | | C1-6FL5 | | | | | | | | | |
| 7006 | 3 | | C1-6FL6 | | | | | | | | | |
| 7007 | 3 | | C2-6FL1 | | | | | | | | | |
| 7008 | 3 | | C3-6FL1 | | | | | | | | | |
| 7009 | 3 | | C4-6FL1 | | | | | | | | | |
| 7010 | 3 | | C5-6FL1 | | | | | | | | | |
| 7011 | 3 | | C6-6FL1 | | | | | | | | | |
| 7012 | 3 | | C7-6FL1 | | | | | | | | | |
| 7013 | 3 | | C8-6FL1 | | | | | | | | | |
| 7014 | 3 | | C9-6FL1 | | | | | | | | | |
| 7015 | 3 | | C10-6FL1 | | | | | | | | | |
| 7016 | 3 | | C11-6FL1 | | | | | | | | | |
| 7017 | 3 | | | C1-6FL1 | | | | | | | | |
| 7018 | 3 | | | C1-6FL2 | | | | | | | | |
| 7019 | 3 | | | C1-6FL3 | | | | | | | | |
| 7020 | 3 | | | C1-6FL4 | | | | | | | | |
| 7021 | 3 | | | C1-6FL5 | | | | | | | | |
| 7022 | 3 | | | C1-6FL6 | | | | | | | | |
| 7023 | 3 | | | C2-6FL1 | | | | | | | | |
| 7024 | 3 | | | C3-6FL1 | | | | | | | | |
| 7025 | 3 | | | C4-6FL1 | | | | | | | | |
| 7026 | 3 | | | C5-6FL1 | | | | | | | | |
| 7027 | 3 | | | C6-6FL1 | | | | | | | | |
| 7028 | 3 | | | C7-6FL1 | | | | | | | | |
| 7029 | 3 | | | C8-6FL1 | | | | | | | | |
| 7030 | 3 | | | C9-6FL1 | | | | | | | | |

TABLE 14-continued

| Exemplified Compound No. | n | R1 | R2 | R3 | R4 | R5 | R6 | R7 | R8 | R9 | R10 | Addition ligand |
|---|---|---|---|---|---|---|---|---|---|---|---|---|
| 7031 | 3 | | | C10-6FL1 | | | | | | | | |
| 7032 | 3 | | | C11-6FL1 | | | | | | | | |
| 7033 | 3 | | | | | | | | C1-6FL1 | | | |
| 7034 | 3 | | | | | | | | C1-6FL2 | | | |
| 7035 | 3 | | | | | | | | C1-6FL3 | | | |
| 7036 | 3 | | | | | | | | C1-6FL4 | | | |
| 7037 | 3 | | | | | | | | C1-6FL5 | | | |
| 7038 | 3 | | | | | | | | C1-6FL6 | | | |
| 7039 | 3 | | | | | | | | C2-6FL1 | | | |
| 7040 | 3 | | | | | | | | C3-6FL1 | | | |
| 7041 | 3 | | | | | | | | C4-6FL1 | | | |
| 7042 | 3 | | | | | | | | C5-6FL1 | | | |
| 7043 | 3 | | | | | | | | C6-6FL1 | | | |
| 7044 | 3 | | | | | | | | C7-6FL1 | | | |
| 7045 | 3 | | | | | | | | C8-6FL1 | | | |
| 7046 | 3 | | | | | | | | C9-6FL1 | | | |
| 7047 | 3 | | | | | | | | C10-6FL1 | | | |
| 7048 | 3 | | | | | | | | C11-6FL1 | | | |
| 7049 | 2 | | | C1-6FL1 | | | | | | | | acac |
| 7050 | 2 | | | C1-6FL2 | | | | | | | | acac |
| 7051 | 2 | | | C1-6FL3 | | | | | | | | acac |
| 7052 | 2 | | | C1-6FL4 | | | | | | | | acac |
| 7053 | 2 | | | C1-6FL5 | | | | | | | | acac |
| 7054 | 2 | | | C1-6FL6 | | | | | | | | acac |
| 7055 | 2 | | | C2-6FL1 | | | | | | | | acac |
| 7056 | 2 | | | C3-6FL1 | | | | | | | | acac |
| 7057 | 2 | | | C4-6FL1 | | | | | | | | acac |
| 7058 | 2 | | | C5-6FL1 | | | | | | | | acac |
| 7059 | 2 | | | C6-6FL1 | | | | | | | | acac |
| 7060 | 2 | | | C7-6FL1 | | | | | | | | acac |
| 7061 | 2 | | | C8-6FL1 | | | | | | | | acac |
| 7062 | 2 | | | C9-6FL1 | | | | | | | | acac |
| 7063 | 2 | | | C10-6FL1 | | | | | | | | acac |
| 7064 | 2 | | | C11-6FL1 | | | | | | | | acac |
| 7065 | 3 | F | | C1-6FL1 | | | | | | | | |
| 7066 | 3 | CH$_3$O | | C1-6FL1 | | | | | | | | |
| 7067 | 3 | F | | C2-6FL1 | | | | | | | | |
| 7068 | 3 | CH$_3$O | | C2-6FL1 | | | | | | | | |

The iridium coordination compound of the present invention is useful as a light emitting material for an organic EL device. Needless to say, the compound has high luminous efficiency. In addition, the compound is suitable for a spin coating process involving applying a solution of the compound, various printing methods, and an application mode involving the use of an ink-jet nozzle.

Next, a light emitting device of the present invention will be described.

A light emitting device includes at least two electrodes, and a light emitting layer interposed between the electrodes, in which the light emitting layer contains the light emitting material according to the present invention.

The light emitting layer may be a layer formed only of the light emitting material of the present invention, or may be a layer formed of the light emitting material of the present invention and a host compound. In the case of a layer formed of the light emitting material and the host compound, the content of the light emitting material of the present invention is not particularly limited; the content is preferably 0.1 wt % or more to 99 wt % or less, or more preferably 1 wt % or more to 70 wt % or less.

Examples of the host compound include an oligofluorene represented by the following structural formula (8) and a polyfluorene having a molecular weight of 10,000 or more to 100,000 or less represented by the following structural formula (9).

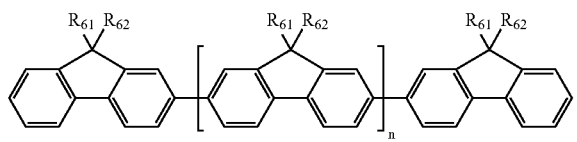

(8)

n represents 1 or more to 20 or less.

$R_{61}$ and $R_{62}$ are each independently selectable from functional groups in each fluorene group, and each represent a trifluoromethyl group, or a linear, branched, or cyclic alkyl or alkoxyl group having 2 or more carbon atoms a hydrogen atom of which may be substituted by a halogen atom.

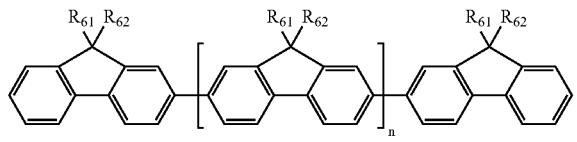

(9)

$R_{41}$ and $R_{42}$ are each independently selectable from functional groups in each fluorene group, and are each selected from a linear, branched, or cyclic alkyl group having 2 or more carbon atoms, and a trifluoromethyl group.

An oligofluorene or polyfluorene having a structure in which fluorene groups are continuously bonded to each other has the following properties.

(1) A charge transporting ability upon application of an electric field to the light emitting layer is high.

(2) The lowest triplet excitation energy (T1) level of the oligofluorene or polyfluorene is higher than the T1 level of the iridium coordination compound of the present invention, so excitation energy can be efficiently transferred to the iridium coordination compound of the present invention.

(3) The T1 level of the oligofluorene or polyfluorene is higher than the T1 level of the iridium coordination compound of the present invention, so the oligofluorene or polyfluorene does not absorb the excitation energy of the iridium coordination compound, and the iridium coordination compound can emit light with high efficiency.

(4) Compatibility between the iridium coordination compound of the present invention and the oligofluorene or polyfluorene is good, so a high-quality thin film of the materials can be formed upon production of the device.

Hereinafter, examples will be described.

EXAMPLES 1 TO 6

Hereinafter, a method of synthesizing each of Exemplified Compound 1001 (Example 1), Exemplified Compound 1002 (Example 2), Exemplified Compound 1003 (Example 3), Exemplified Compound 1004 (Example 4), Exemplified Compound 1007 (Example 5), and Exemplified Compound 1008 (Example 6) will be described.

The synthesis of each of those compounds follows a general synthesis method involving producing a C—C bond or C—N bond between aryl groups, and employs mainly a Suzuki coupling method based on a reaction between a halide and boric acid using a palladium catalyst.

First, the following scheme shows a method of synthesizing the intermediate of an oligofluorenyl group involving sequentially coupling fluorene groups by Suzuki coupling.

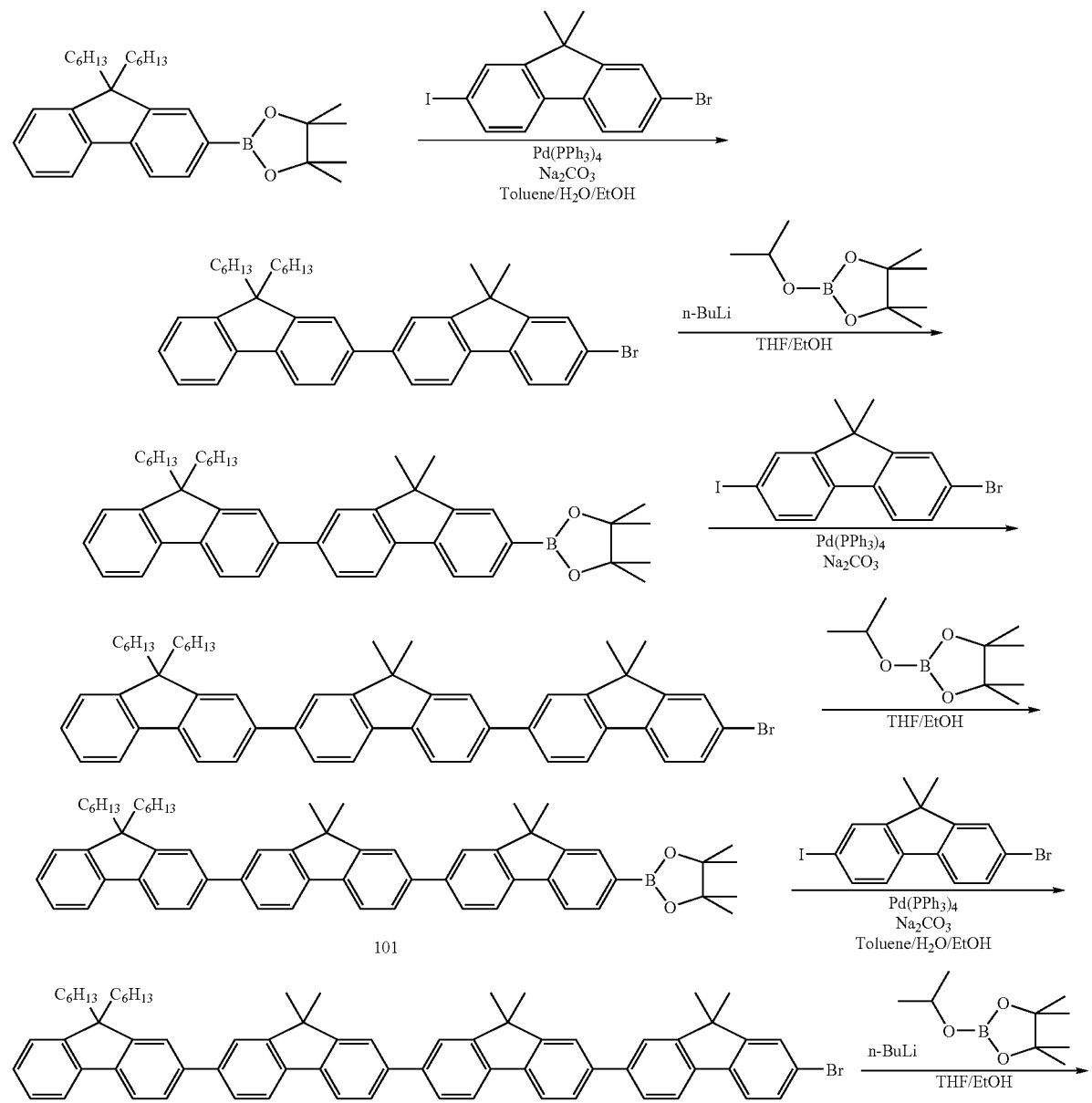

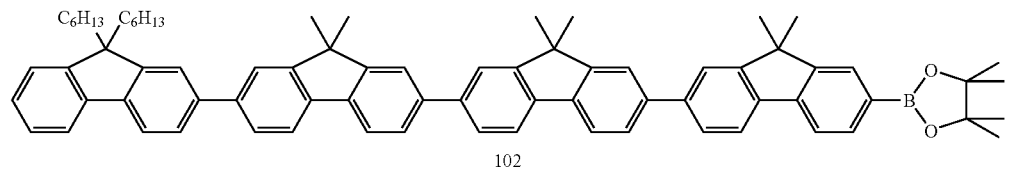

102

The following schemes each show a scheme in which a phenylisoquinoline skeleton and an oligofluorenyl group are bonded to each other. The ligands of Exemplified Compounds 1001 and 1004 can be synthesized by the schemes. ¹H-NMR is employed for the identification of a compound.

Similarly, the following schemes each show the synthesis of: the ligand of Exemplified Compound 1002; the ligand of Exemplified Compound 1003; the ligand of Exemplified Compound 1007; or the ligand of Exemplified Compound 1008. ¹H-NMR is employed for the identification of each compound.

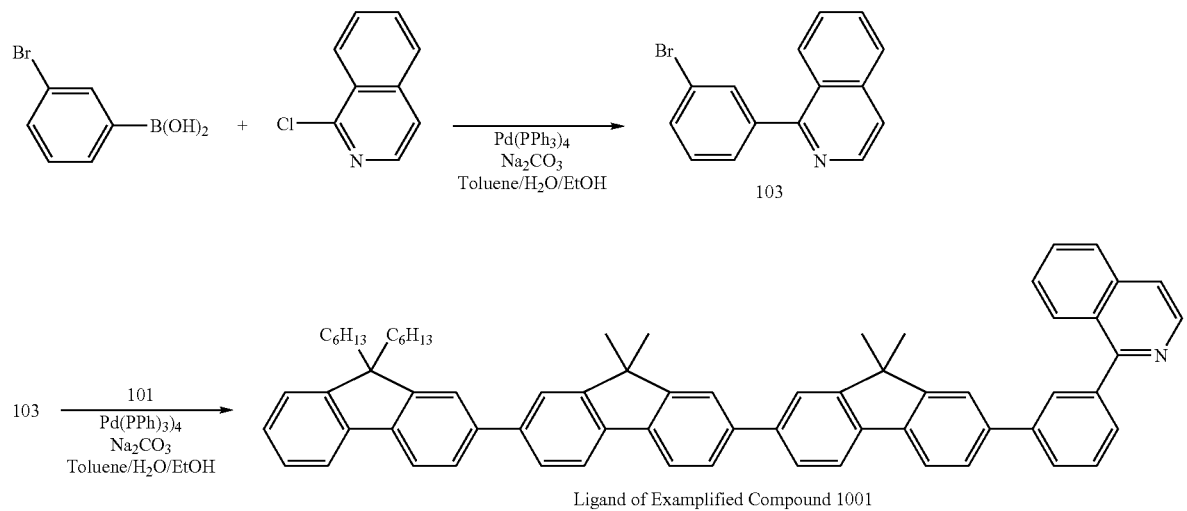

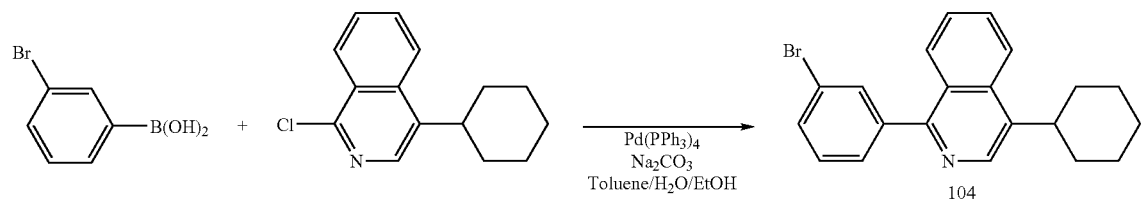

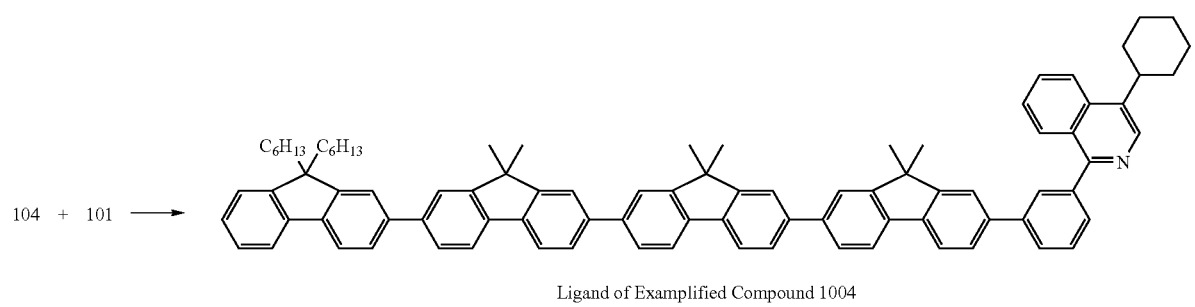

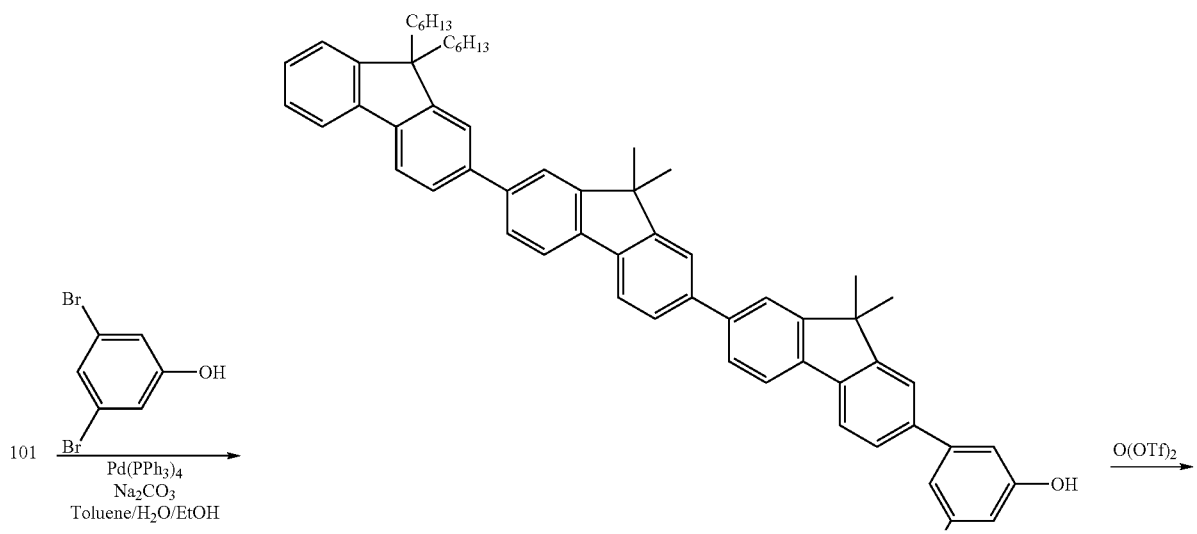
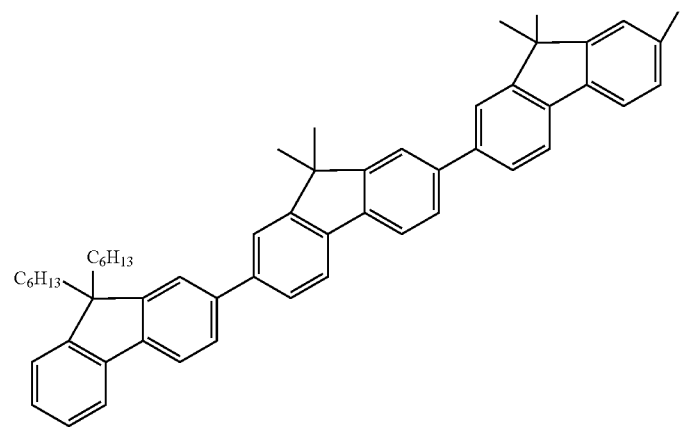
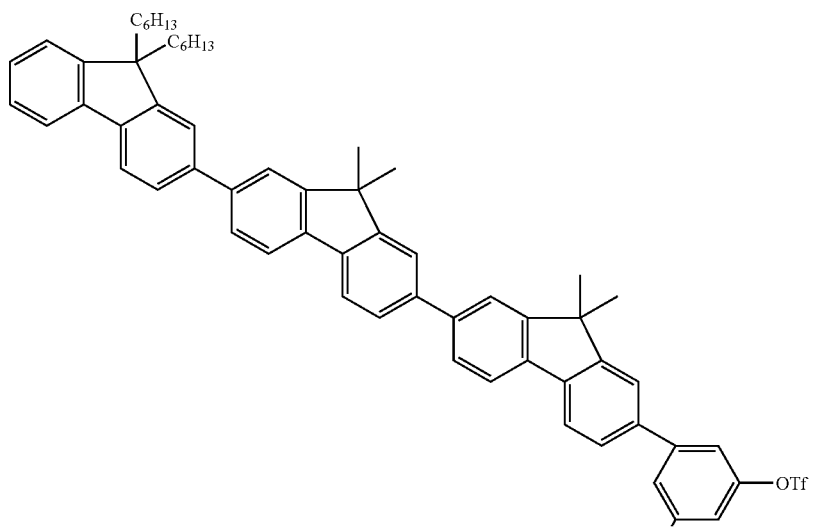

-continued
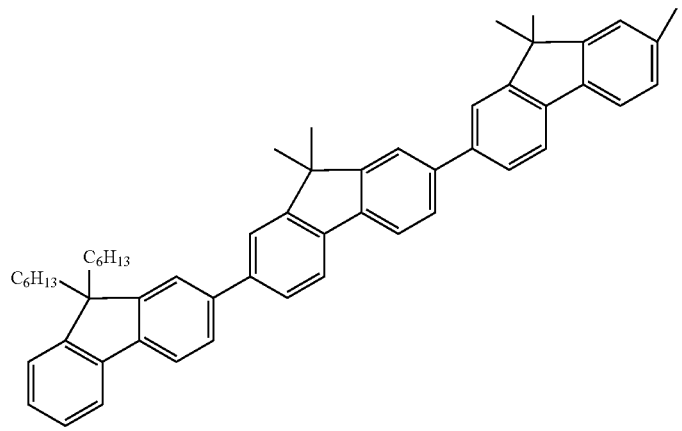
105
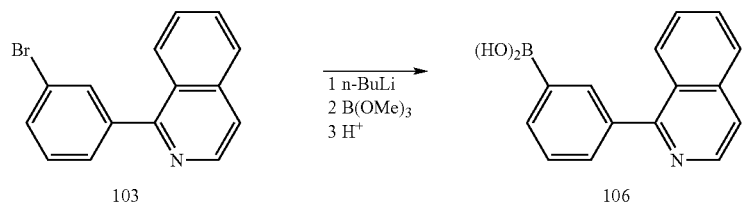
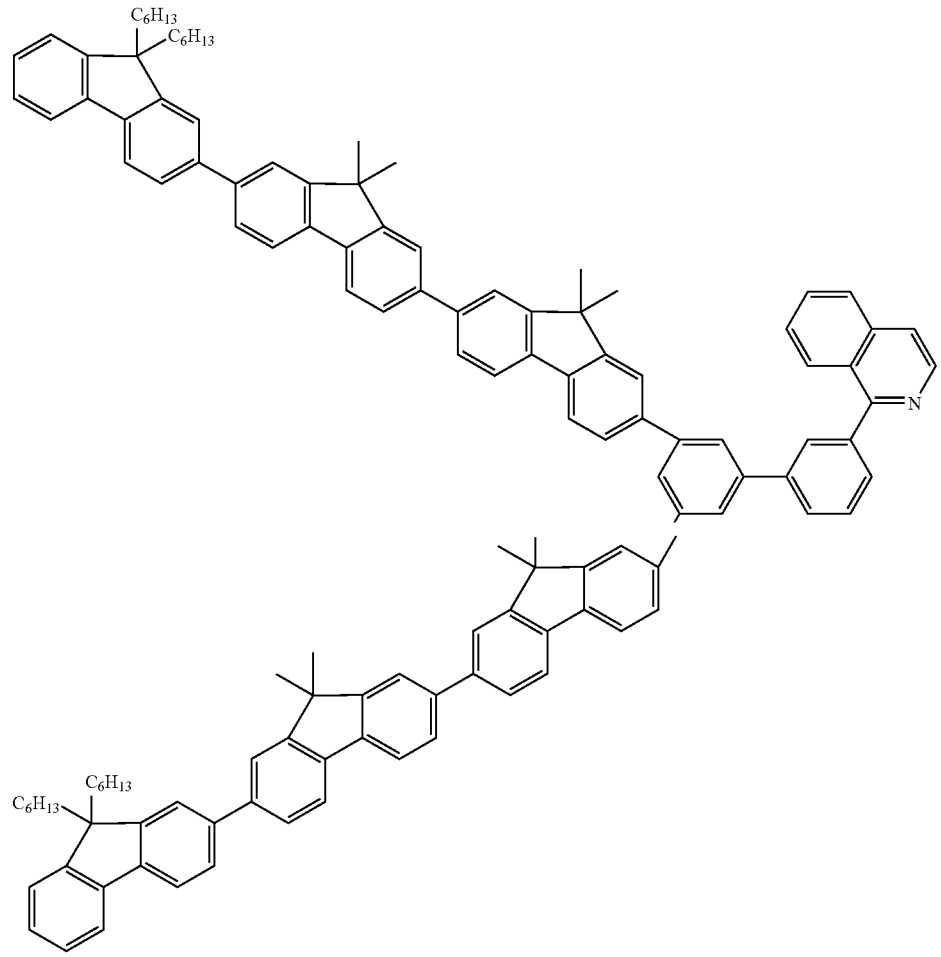
Ligand of Exemplified Compound 1002

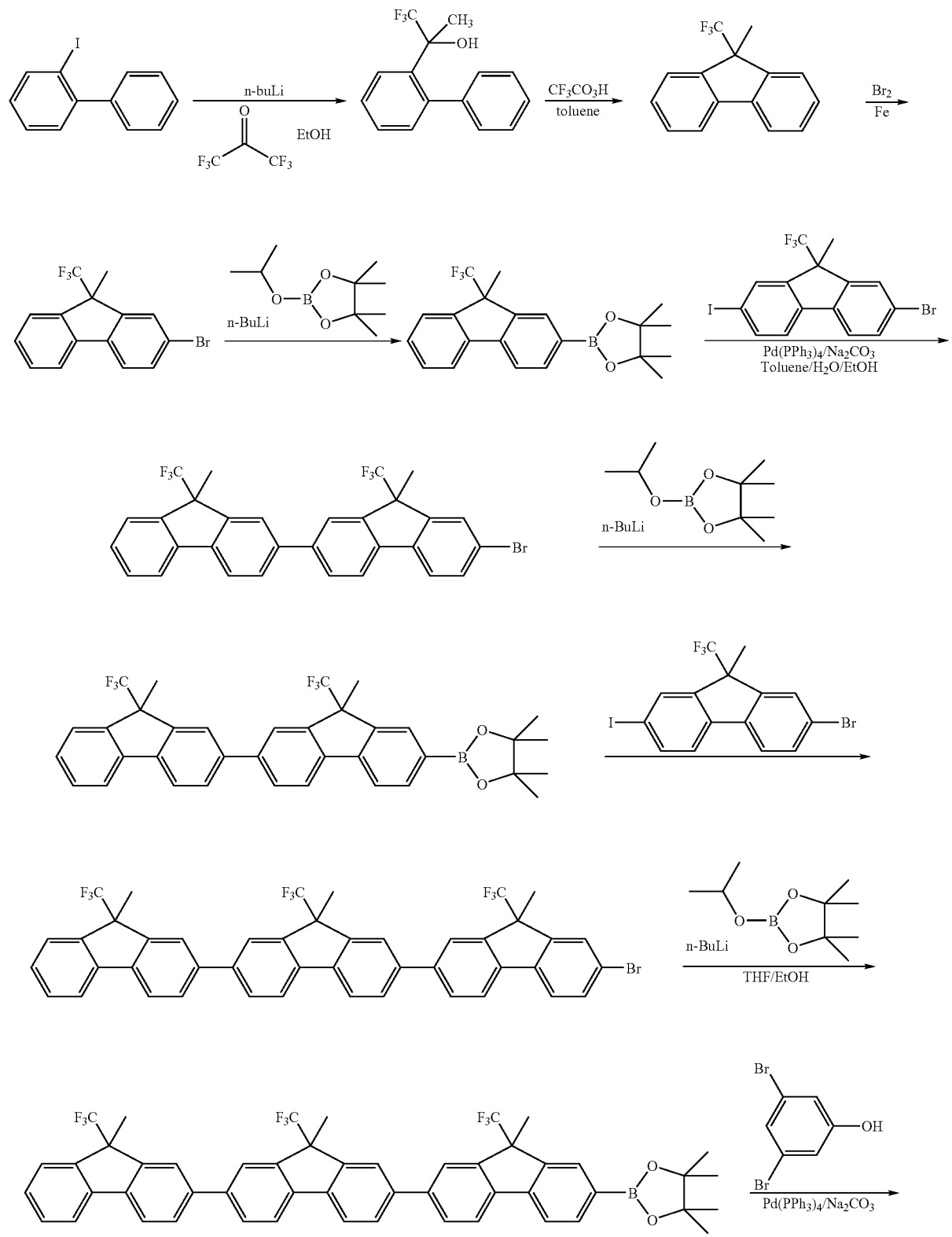

-continued
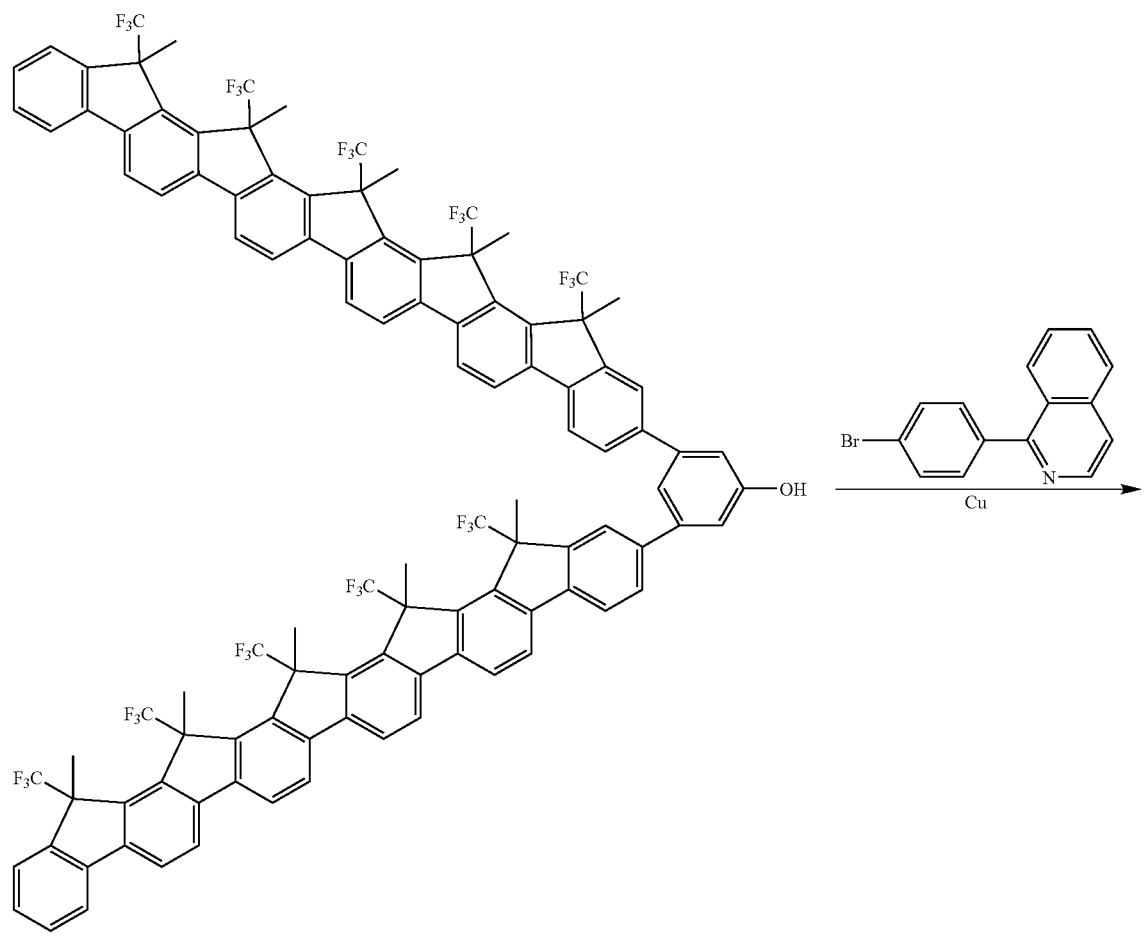

-continued
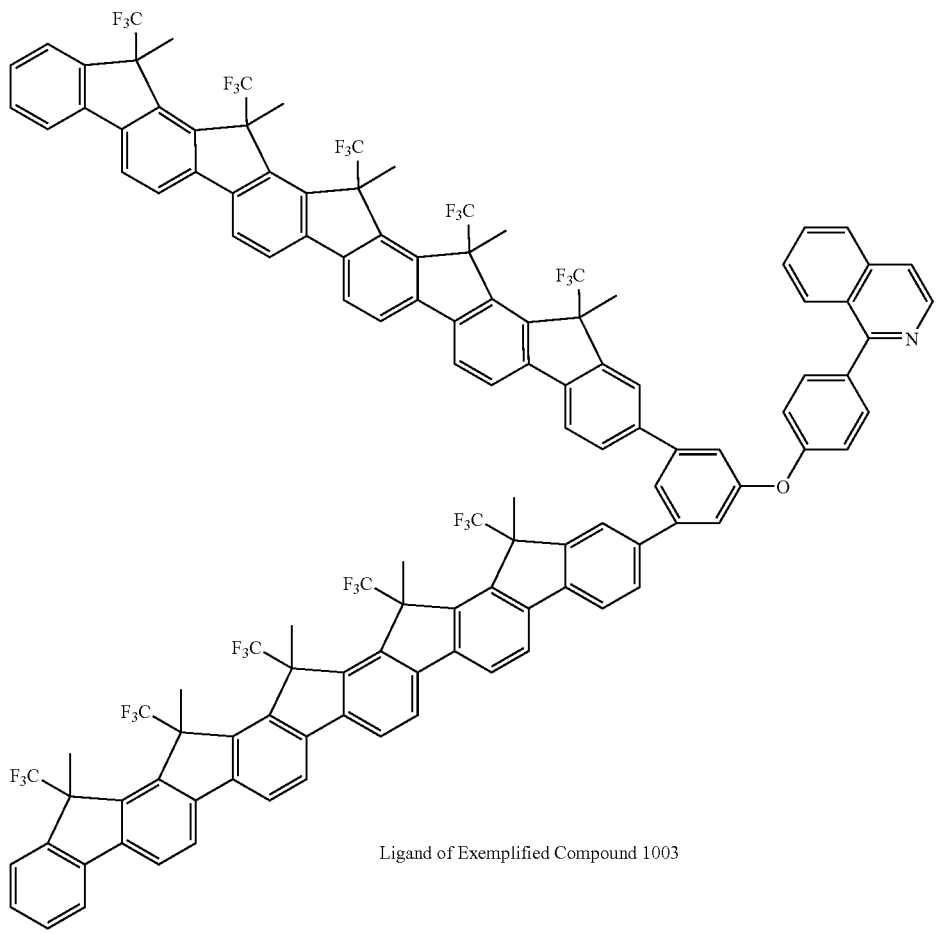
Ligand of Exemplified Compound 1003
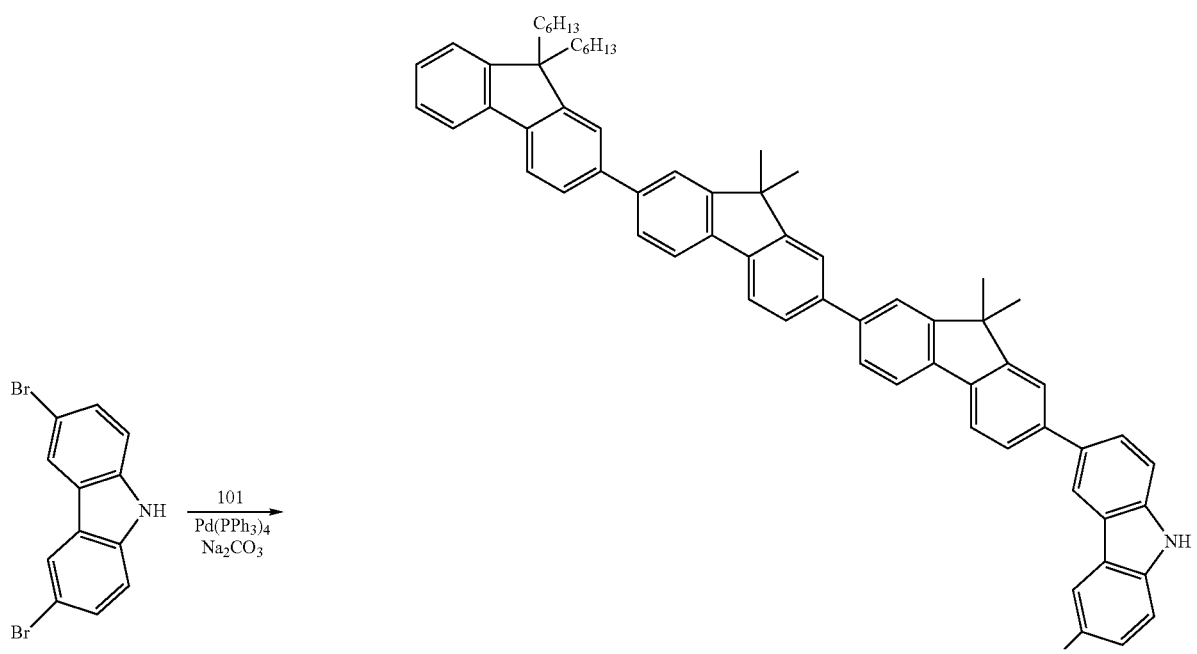

-continued
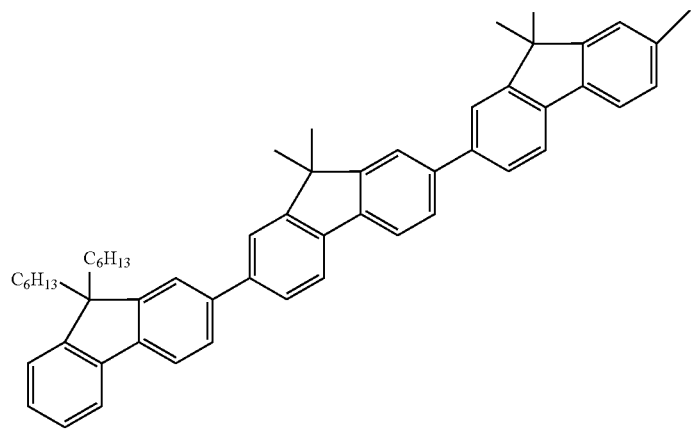
107
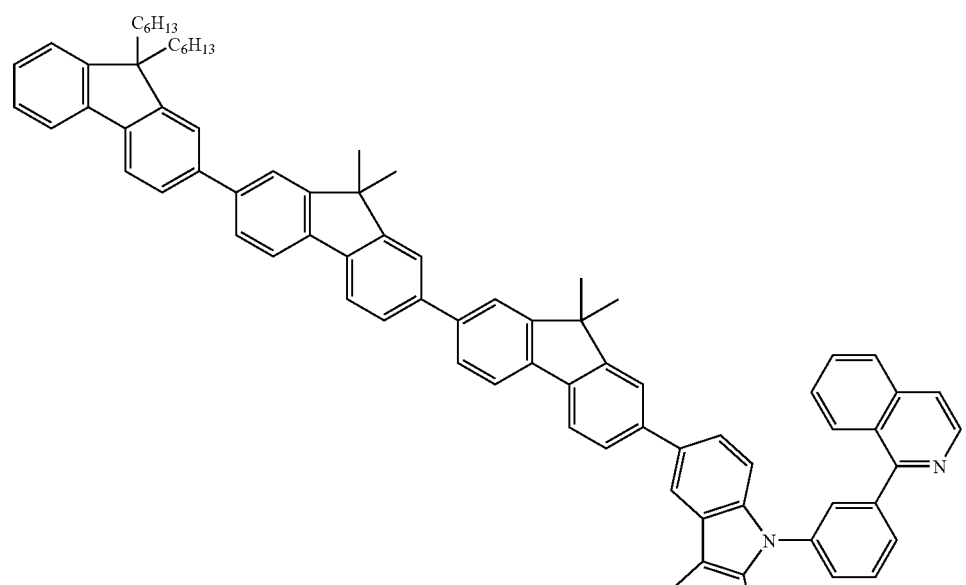
107 →(103, Pd(OAc)₂)
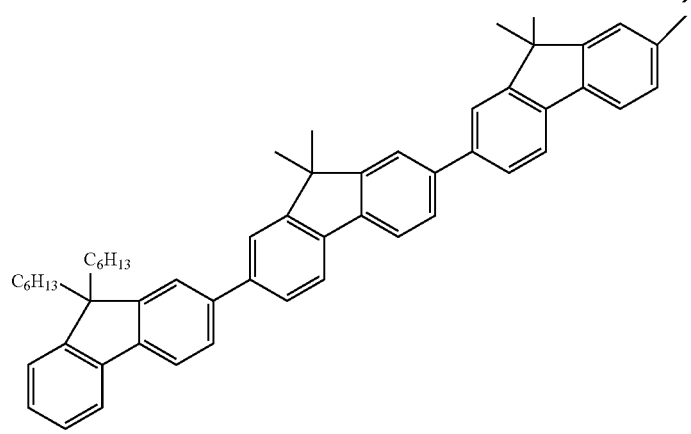
Ligand Exemplified Compound 1007

-continued

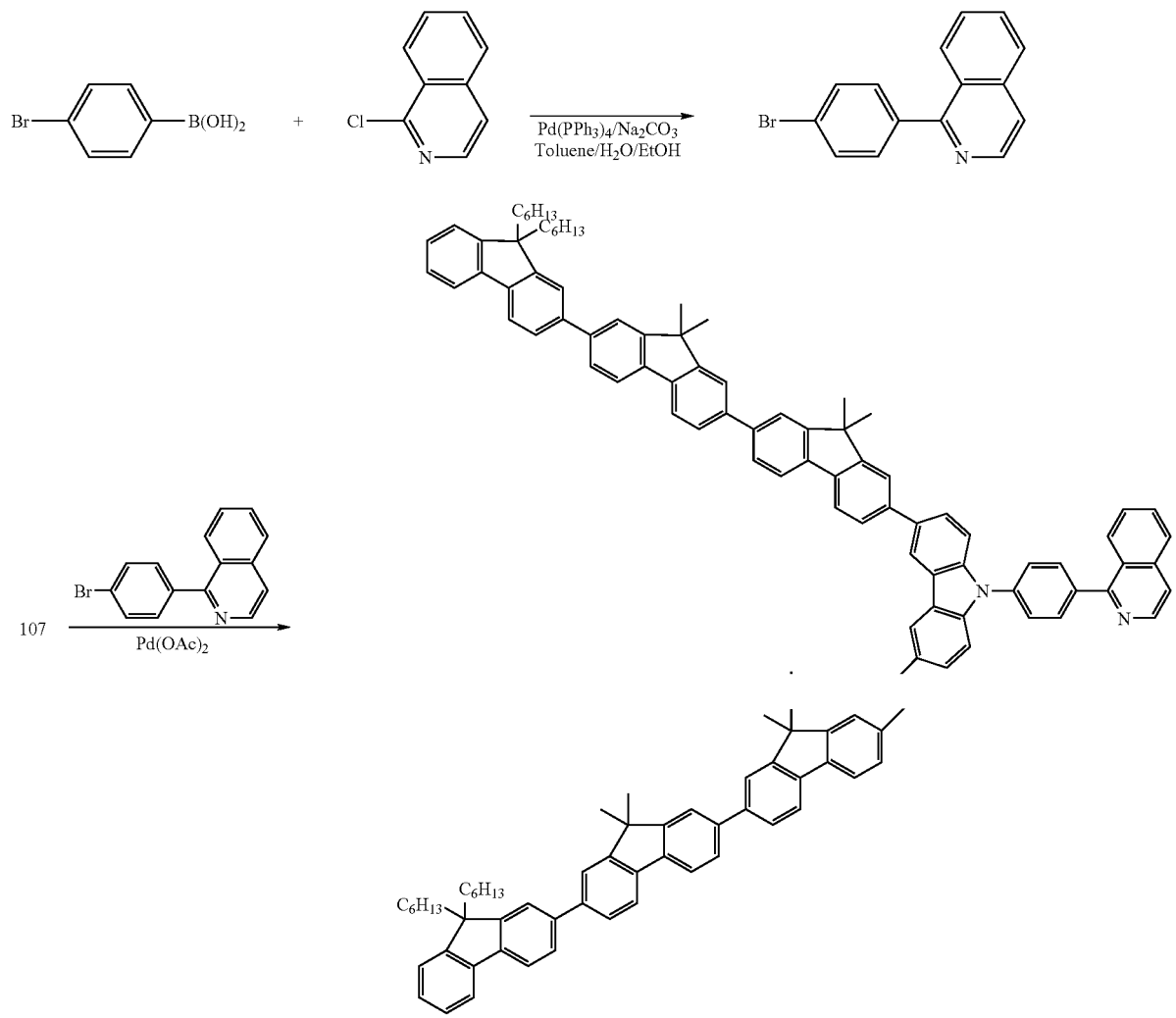

Ligand of Exemplified Compound 1008

The following scheme is a synthesis scheme for coordinating each of the ligands synthesized in the above schemes to iridium. In each of all exemplified compounds, iridium can be turned into a coordination compound by common steps. Each of an Ir(acac) body to be produced in a second step and Ir with three ligands to be produced in a third step can be used as a light emitting material; in each of these examples, Ir with three ligands to be produced in the third step is a target compound.

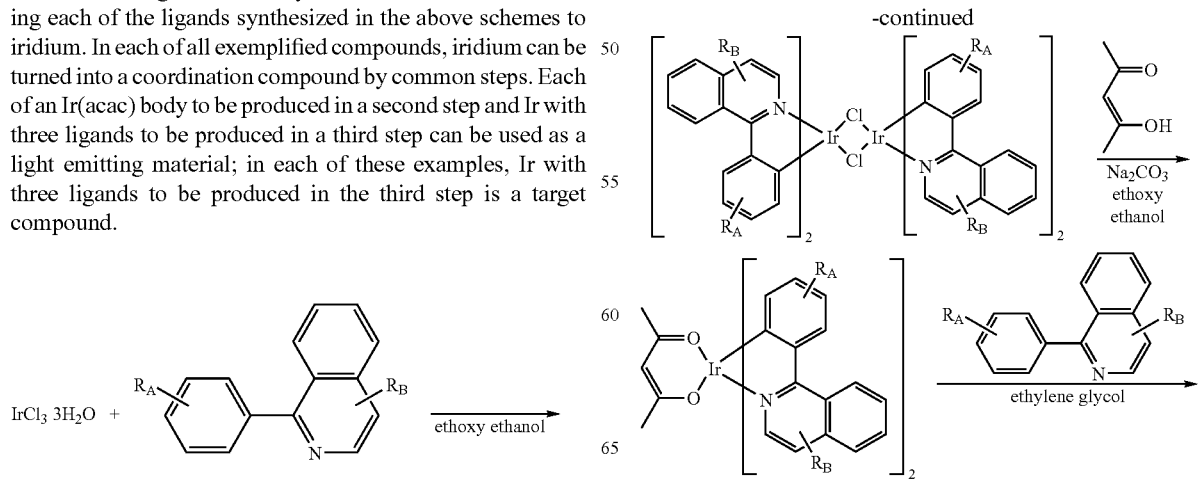

-continued

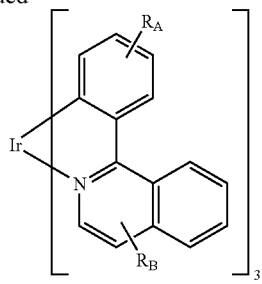

EXAMPLES 7 TO 9

These examples are synthesis examples of Exemplified Compound 1014 (Example 7), Exemplified Compound 1015 (Example 8), and Exemplified Compound 1016 (Example 9).

Procedures for synthesizing ligands were shown below. In each procedure, a ligand was synthesized by using a Suzuki coupling reaction, in which a palladium catalyst was used, plural times.

(A)

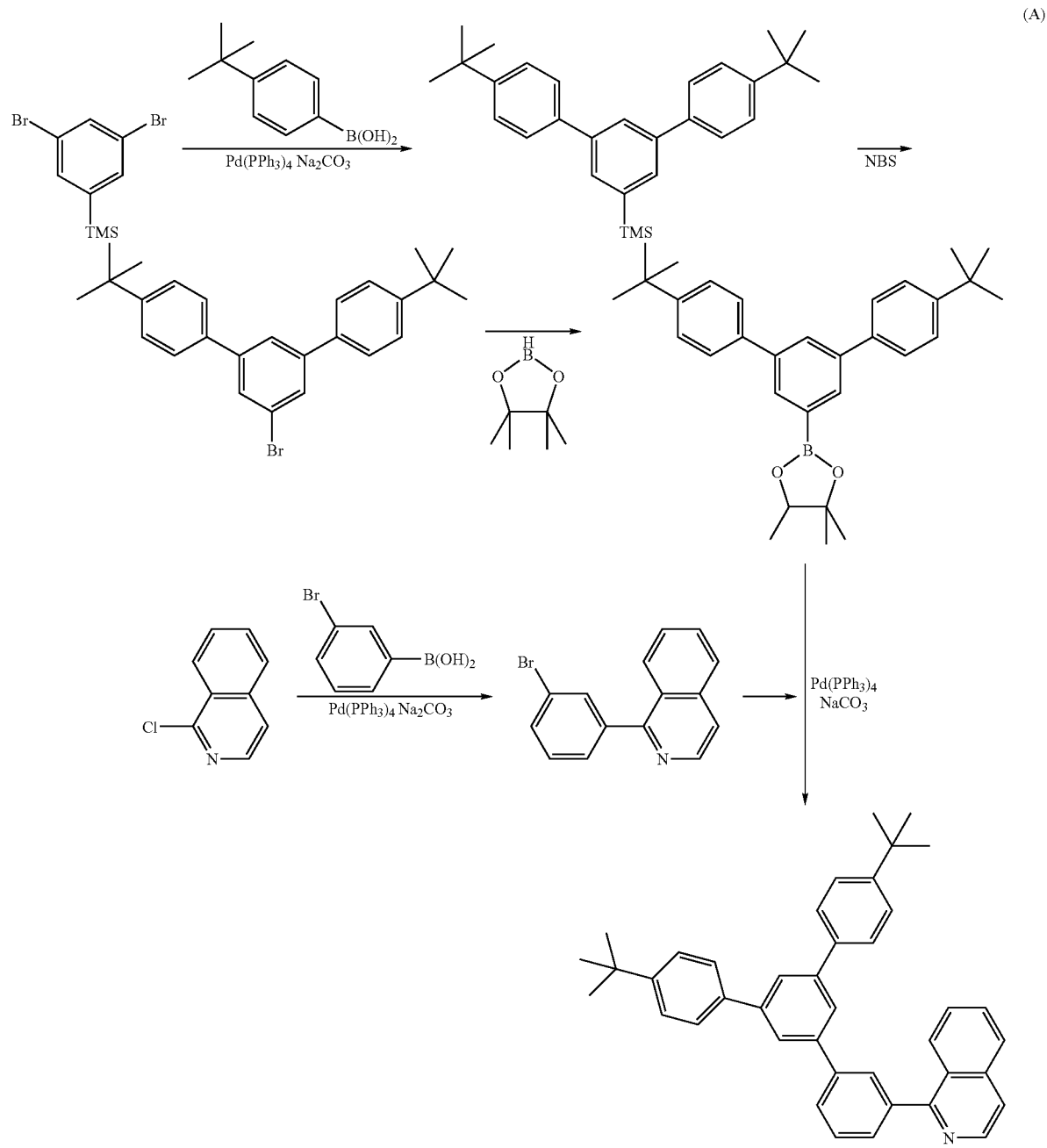

Ligand of Each Exemplified Compounds 1014 and 1015

-continued

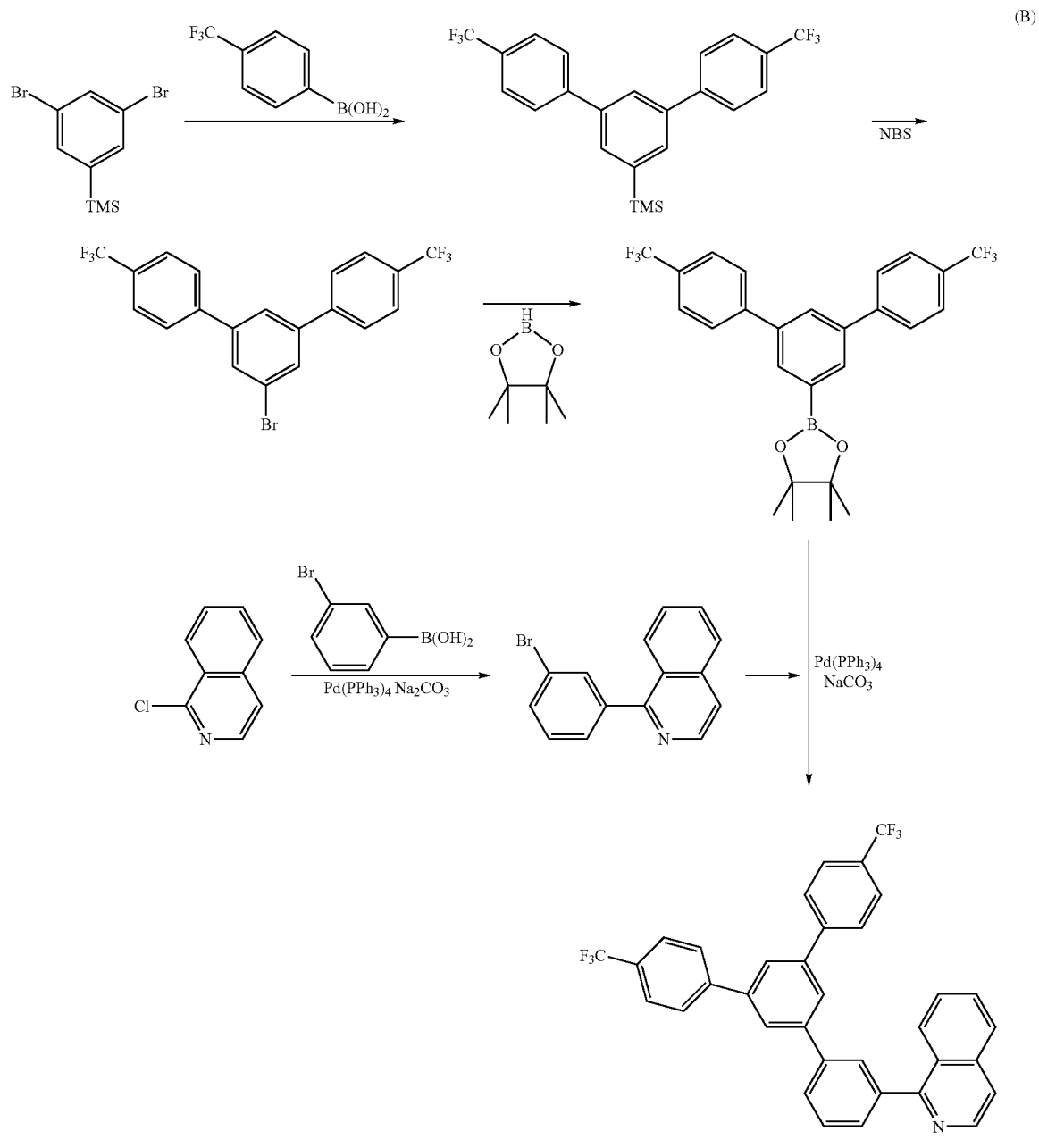

Ligand of Exemplified Compounds 1016

Iridium complexes were synthesized by using the ligands in accordance with procedures similar to those of Examples 1 to 6.

The compounds were identified by employing proton NMR and matrix assisted laser desorption/ionization time-of-flight mass spectrometry (MARDI-TOF-MASS) (Autoflex type manufactured by Bruker Daltonics Inc. (Germany)).

Figure 1B:
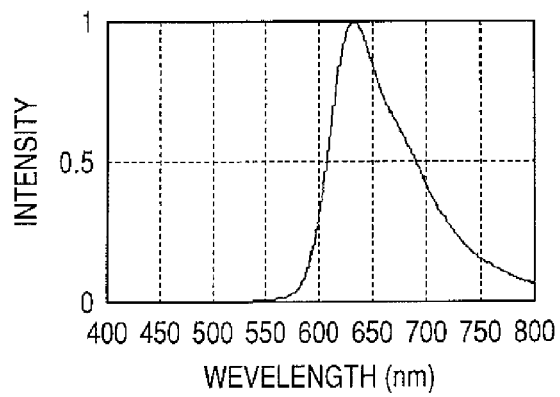
Figure 1C:
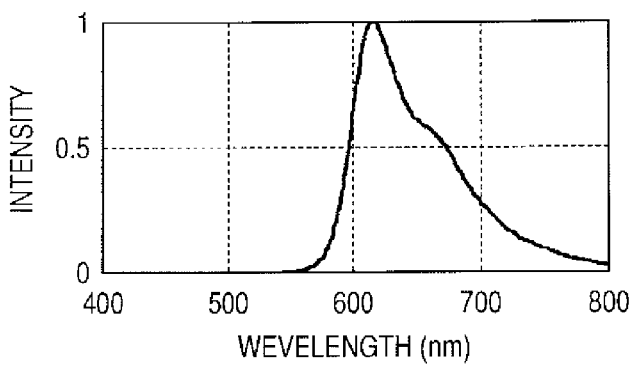

FIGS. 1A to 1C showed the emission spectra of solutions of Exemplified Compounds 1014 to 1016 in toluene. Exemplified Compounds 1014, 1015, and 1016 had light emission peak wavelengths of 620 nm, 633 nm, and 633 nm, respectively, and each emitted pure red light.

EXAMPLES 10 TO 12

Examples of organic LED devices each using Exemplified Compound 1014, 1015, or 1016 will be described. Each of those complexes can be dissolved well in a xylene solution, and is suitable for an organic EL device to be produced by a spin coating method.

A device having a constitution including three organic layers was produced. ITO having a thickness of 100 nm was patterned into a circular shape on a glass substrate so that an electrode area would be 3.14 mm$^2$.

PEDOT (for an organic EL) manufactured by Bayer was applied onto the ITO substrate by spin coating at 1,000 rpm (20 seconds) so as to form a film having a thickness of 40 nm. The resultant was dried in a vacuum chamber at 120° C. for 1 hour.

The upper portion of the resultant was coated with the following solution by spin coating under a nitrogen atmosphere at 2,000 rpm for 20 seconds, whereby an organic film having a thickness of 60 nm (light emitting layer) was formed. After the formation of the film, the resultant was dried under conditions identical to those at the time of the formation of the PEDOT film.

Xylene: 10 g/polyfluorene shown below (molecular weight 100,000): 70 mg/exemplified compound: 30 mg

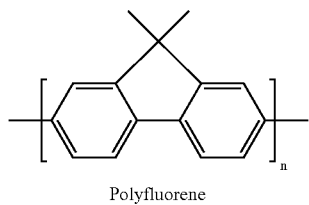

Polyfluorene

The substrate was mounted in a vacuum vapor deposition chamber, and Bphen shown below was deposited from the vapor in a vacuum to form a film having a thickness of 40 nm.

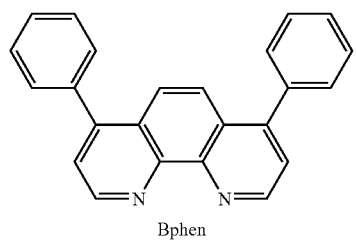

Bphen

The total thickness of the organic layers is 140 nm.

Next, a cathode having the following constitution was formed.

Metal electrode layer (10 nm): AlLi alloy (Li content 1.8 mass %)/metal electrode layer (100 nm): Al After the completion of the above film formation, the resultant device is taken out and evaluated.

Each device is evaluated for characteristics by applying a DC voltage while the cathode is defined as a negative electrode and ITO is defined as a positive electrode. The voltage-current characteristics of each device showed good rectifying property. The emission spectrum and emission luminance of each device were measured with spectrum measuring machines SR1 and BM7 manufactured by TOPCON CORPORATION. A current value at the time of the application of a voltage can be measured with a 4140Bd manufactured by Hewlett-Packard Company. Three devices in these examples each emitted good red light. The following table shows the EL luminous efficiency and current density of each device. EL light emission was good at 200 cd/m$^2$, and maintained its quality even after energization for 10 hours.

TABLE 15

| | Light emitting material | Luminous efficiency (at 200 cd/m$^2$) | Current density (at the time of application of 5 V) |
|---|---|---|---|
| Example 10 | Exemplified Compound 1014 | 4.5 cd/A | 15 mA/cm$^2$ |
| Example 11 | Exemplified Compound 1015 | 2.3 cd/A | 10 mA/cm$^2$ |
| Example 12 | Exemplified Compound 1016 | 6.0 cd/A | 28 mA/cm$^2$ |

The results of these examples showed that the compound of the present invention was effective for an organic EL device. In addition, the concentration of a light emitting material in a light emitting layer is typically about 1% or more to 10% or less in order that the concentration quenching of the light emitting material may be avoided; high luminous efficiency was attained even at a light emitting material concentration of 30% as in these examples. In addition, a problem such as phase separation from the host of a light emitting layer was not observed, and stable light emission was obtained.

EXAMPLES 13 AND 14

In each of these examples, only an exemplified compound is used in a light emitting layer.

Devices were each produced in the same manner as in each of Examples 7 to 9 except that a light emitting layer was produced by using the following solution.

Chlorobenzene: 10 g/exemplified compound: 90 mg

The efficiency and current value of a completed device are as shown in the following table.

TABLE 16

| | Light emitting material | Luminous efficiency (at 200 cd/m$^2$) | Current density |
|---|---|---|---|
| Example 13 | Exemplified Compound 1014 | 2.1 cd/A | 28 mA/cm$^2$ |
| Example 14 | Exemplified Compound 1016 | 2.3 cd/A | 40 mA/cm$^2$ |

Even when a light emitting layer was formed only of the iridium coordination compound of the present invention, that is, the content of the compound in the layer was 100%, the iridium coordination compound of the present invention functioned as a light emitting center in an EL device, and was able to provide stable, good luminous efficiency.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-187811, filed Jul. 7, 2006, which is hereby incorporated by reference herein in its entirety.

What is claimed is:

1. A light emitting material represented by the following structural formula:

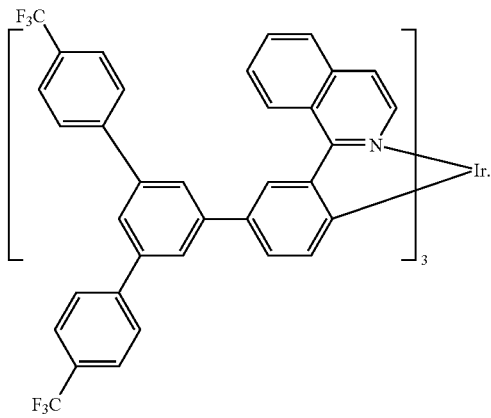

2. A light emitting device comprising:
two electrodes; and
a light emitting layer interposed between the electrodes, wherein the light emitting layer contains the light emitting material according to claim 1.

3. The light emitting device according to claim 2, wherein the light emitting layer contains, as a host compound, an oligofluorene represented by the following structural formula (8):

(8)

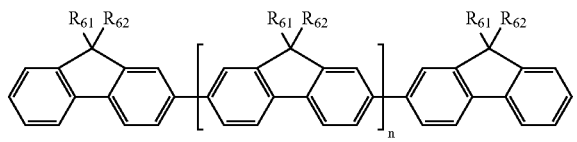

wherein:

n represents 1 to 20; and $R_{61}$ and $R_{62}$ are each independently selected from functional groups in each fluorene group, and each represent a trifluoromethyl group, or a linear, branched, or cyclic alkyl or alkoxyl group having 2 or more carbon atoms a hydrogen atom of which may be substituted by a halogen atom.

4. The light emitting device according to claim 2, wherein the light emitting layer contains, as a host compound, a polyfluorene having a molecular weight of 10,000 to 100,000 represented by the following structural formula (9):

(9)

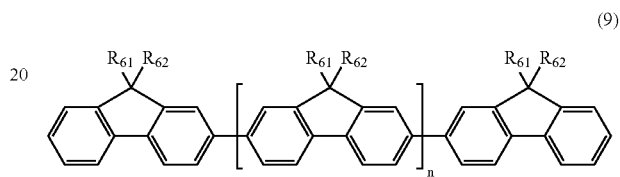

wherein $R_{61}$ and $R_{62}$ are each independently selected from functional groups in each fluorene group, and are each selected from a linear, branched, or cyclic alkyl group having 2 or more carbon atoms, or a trifluoromethyl group.

5. The light emitting device according to claim 2, wherein the light emitting layer comprises a part formed only of the light emitting material.

* * * * *